United States Patent
Han et al.

(10) Patent No.: US 8,679,648 B2
(45) Date of Patent: Mar. 25, 2014

(54) HETEROCYCLIC COMPOUND AND ORGANIC LIGHT-EMITTING DIODE INCLUDING THE SAME

(75) Inventors: Sang-Hyun Han, Yongin (KR); Seok-Hwan Hwang, Yongin (KR); Young-Kook Kim, Yongin (KR); Hye-Jin Jung, Yongin (KR); Jin-O Lim, Yongin (KR); Soo-Yon Kim, Yongin (KR); Il-Soo Oh, Yongin (KR); Jong-Hyuk Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 157 days.

(21) Appl. No.: 13/346,500

(22) Filed: Jan. 9, 2012

(65) Prior Publication Data

US 2013/0037782 A1  Feb. 14, 2013

(30) Foreign Application Priority Data

Aug. 11, 2011 (KR) .................. 10-2011-0080186

(51) Int. Cl.
  *H01L 51/54* (2006.01)
(52) U.S. Cl.
  USPC ........... 428/690; 428/917; 313/504; 313/505; 313/506; 257/40; 257/E51.05; 257/E51.026; 257/E51.032; 546/79; 546/81; 546/101; 548/418; 548/440; 564/26; 564/426; 564/434
(58) Field of Classification Search
  USPC .................. 428/690, 917; 313/504, 505, 506; 257/40, E51.05, E51.026, E51.032; 546/79, 81, 101; 548/418, 440; 564/26, 564/426, 434
See application file for complete search history.

(56) References Cited

U.S. PATENT DOCUMENTS

| | | | |
|---|---|---|---|
| 7,053,255 B2 | 5/2006 | Ikeda et al. | |
| 7,233,019 B2 | 6/2007 | Ionkin et al. | |
| 7,846,559 B2 | 12/2010 | Hwang et al. | |
| 7,875,368 B2 | 1/2011 | Ohrui et al. | |
| 2009/0233937 A1 | 9/2009 | Ishikawa et al. | |
| 2011/0031483 A1* | 2/2011 | Kwak et al. ............ | 257/40 |
| 2011/0049488 A1 | 3/2011 | Kim et al. | |
| 2011/0204295 A1 | 8/2011 | Kuwabara et al. | |

FOREIGN PATENT DOCUMENTS

| | | |
|---|---|---|
| KR | 10-2006-0006760 | 7/2005 |
| KR | 10-2006-0052312 | 7/2006 |
| KR | 10-2006-0113254 | 11/2006 |
| KR | 10-2008-0059082 | 2/2009 |
| KR | 10-2010-0108903 | 10/2010 |
| KR | 10-2011-0016031 | 2/2011 |

* cited by examiner

*Primary Examiner* — Gregory Clark
(74) *Attorney, Agent, or Firm* — Robert E. Bushnell, Esq.

(57) ABSTRACT

A heterocyclic compound represented by Formula 1 below and an organic light-emitting diode (OLED) including the same:

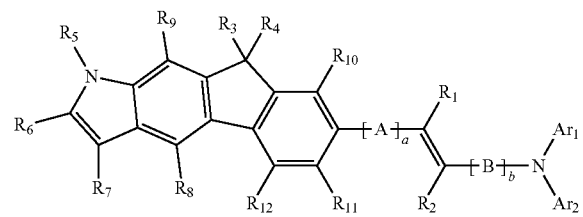

<Formula 1> wherein $R_1$ through $R_{12}$, $Ar_1$, $Ar_2$, A, B, a, and b are the same as defined above. An OLED including an organic layer including the heterocyclic compound has low driving voltage, high luminous efficiency, and a long lifetime.

20 Claims, 1 Drawing Sheet

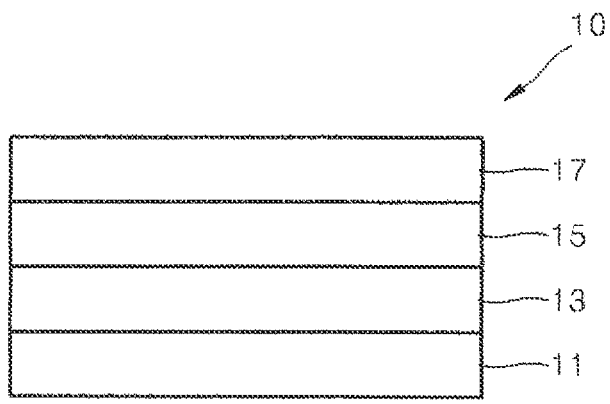

HETEROCYCLIC COMPOUND AND ORGANIC LIGHT-EMITTING DIODE INCLUDING THE SAME

CLAIM OF PRIORITY

This application makes reference to, incorporates the same herein, and claims all benefits accruing under 35 U.S.C. §119 from an application for HETEROCYCLIC COMPOUND AND ORGANIC LIGHT-EMITTING DIODE INCLUDING THE SAME earlier filed in the Korean Intellectual Property Office on 11 Aug. 2011 and there duly assigned Serial No. 10-2011-0080186.

BACKGROUND OF THE INVENTION

1. Field of the Invention

The present invention relates to a heterocyclic compound represented by Formula 1 and an organic light-emitting diode including the same.

2. Description of the Related Art

Organic light-emitting diodes (OLEDs), which are self-emitting devices, have advantages such as a wide viewing angle, excellent contrast, quick response, high brightness, and excellent driving voltage characteristics, and the ability to provide multicolored images.

A general OLED has a structure including a substrate, an anode, a hole transport layer (HTL), an emission layer (EML), an electron transport layer (ETL), and a cathode which are sequentially stacked on the substrate. In this regard, the HTL, the EML, and the ETL are organic layers formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a novel heterocyclic compound used for an organic light-emitting diode (OLED), such that the OLED has low driving voltage, high luminance; high efficiency, and a long lifetime.

The present invention also provides an OLED including an organic layer including the heterocyclic compound.

According to an aspect of the present invention, there is provided a heterocyclic compound represented by Formula 1 below:

Formula 1

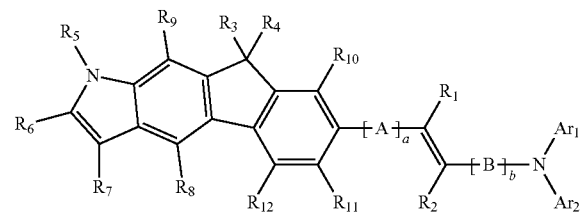

wherein $R_1$ through $R_{12}$ are each independently selected from the group consisting of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted alkoxy group, a substituted or unsubstituted. $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted heteroaryl group, a substituted or unsubstituted $C_5$-$C_{30}$ aryloxy group, a substituted or unsubstituted $C_5$-$C_{30}$ arylthio group, and an amino group substituted with a substituted or unsubstituted $C_5$-$C_{30}$ aryl group or a substituted or unsubstituted $C_3$-$C_{30}$ heteroaryl group; optionally, $R_3$ and $R_4$ may be linked to form a substituted or unsubstituted $C_5$-$C_{30}$ aryl group; $Ar_1$ and $Ar_2$ are each independently a substituted or unsubstituted $C_5$-$C_{30}$ aryl group and a substituted or unsubstituted $C_3$-$C_{30}$ heteroaryl group, and optionally, $Ar_1$ and $Ar_2$ are linked to each other to form a ring, thereby forming a substituted or unsubstituted $C_3$-$C_{30}$ heteroaryl group; A and B are divalent linking groups, and each independently a substituted or unsubstituted $C_5$-$C_{30}$ arylene group or a substituted or unsubstituted $C_3$-$C_{30}$ heteroarylene group; and a is an integer of 0 to 3, wherein when a is 2 or greater, at least two of A groups are the same as or different from each other; and b is an integer of 0 to 3, wherein when b is 2 or greater, at least two of B groups are the same as or different from each other.

According to another aspect of the present invention, there is provided an organic light-emitting diode including: a first electrode; a second electrode facing the first electrode; and an organic layer interposed between the first electrode and the second electrode, wherein the organic layer includes at least one layer and the heterocyclic compound represented by Formula 1 described above.

BRIEF DESCRIPTION OF THE DRAWING

A more complete appreciation of the present invention, and many of the attendant advantages thereof, will be readily apparent as the present invention becomes better understood by reference to the following detailed description when considered in conjunction with the accompanying drawing, in which like reference symbols indicate the same or similar components, wherein:

FIG. 1 is a schematic diagram of an organic light-emitting diode according to an embodiment of the present invention.

DETAILED DESCRIPTION OF THE INVENTION

The present invention will now be described more fully with reference to the accompanying drawing, in which exemplary embodiments of the present invention are shown. One or more embodiments of the present invention will now be described in detail.

According to an embodiment of the present invention, there is provided a heterocyclic compound represented by Formula 1 below:

Formula 1

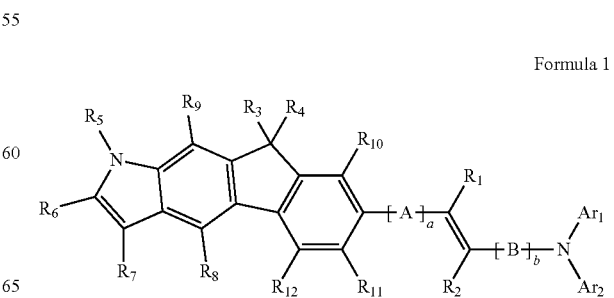

wherein $R_1$ through $R_{12}$ are each independently selected from the group consisting of a hydrogen atom, a deuterium atom, a halogen atom; a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, and an to amino group substituted with a substituted or unsubstituted $C_5$-$C_{30}$ aryl group or a substituted or unsubstituted $C_3$-$C_{30}$ heteroaryl group; optionally, $R_3$ and $R_4$ may be linked to form a substituted or unsubstituted $C_5$7$C_{30}$ aryl group; $Ar_1$ and $Ar_2$ are each independently a substituted or unsubstituted $C_5$-$C_{30}$ aryl group and a substituted or unsubstituted $C_3$-$C_{30}$ heteroaryl group, and optionally, $Ar_1$ and $Ar_2$ are linked to each other to form a ring, thereby forming a substituted or unsubstituted $C_3$-$C_{30}$ heteroaryl group; A and B, which are divalent linking groups, may be each independently a substituted or unsubstituted $C_5$-$C_{30}$ arylene group or a substituted or unsubstituted $C_3$-$C_{30}$ heteroarylene group; and a is an integer of 0 to 3 wherein when a is 2 or greater, at least two of A groups may be the same as or different from each other, and b is an integer of 0 to 3 wherein when b is 2 or greater, at least two of B groups may be the same as or different from each other.

In particular, each of $R_1$ through $R_{12}$ may be independently selected from the group consisting of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spiro-fluorenyl group, a substituted or unsubstituted carbozolyl group, a substituted or unsubstituted phenanthrenyl group, a substituted or unsubstituted pyranyl group, a substituted or unsubstituted pyridinyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolinyl group, a substituted or unsubstituted pyrazolyl group, a substituted or unsubstituted imidazopyridinyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolizinyl group, a substituted it or unsubstituted pyridoindolizinyl group, a substituted or unsubstituted indazolyl group, a substituted or unsubstituted carbazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, and a substituted or unsubstituted tetrazolyl group. Optionally, $R_3$ and $R_4$ may be linked to form a substituted or unsubstituted fluorenyl group.

For example, $R_1$ through $R_{12}$ may be each independently, but are not limited to being, selected from the group consisting of a hydrogen atom, a deuterium atom, a halogen atom, a substituted or unsubstituted methyl group, a substituted or unsubstituted ethyl group, a substituted or unsubstituted propyl group, a substituted or unsubstituted butyl group, and groups represented by Formulae 2A through 2H below.

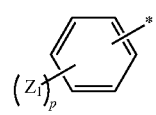

Formual 2A

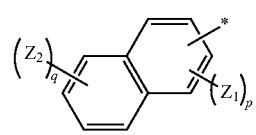

Formula 2B

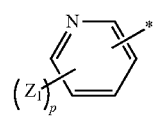

Formula 2C

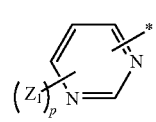

Formula 2D

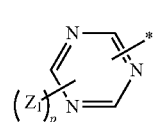

Formula 2E

Formula 2F

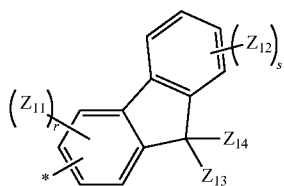

Formula 2G

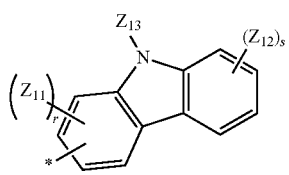

Formula 2H

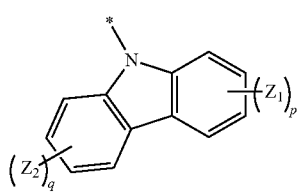

In Formulae 2A through 2H above, $Z_1$, $Z_2$, $Z_3$, and $Z_4$ may be each independently selected from the group consisting of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted carbazolyl group, and a substituted or unsubstituted quinolinyl group. A plurality of $Z_1$ groups and a plurality of $Z_2$ groups may be each independently the same as or different from each other, p may be an integer of 1 to 5, q may be an integer of 1 to 4, and * indicates a binding site.

For example, $R_1$ through $R_{12}$ may be each independently, but are not limited to being, selected from the group consisting of a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, and groups represented by Formulae 3A through 3K below:

Formula 3A

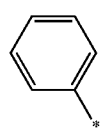

Formula 3B

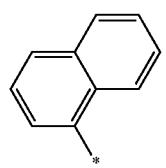

Formual 3C

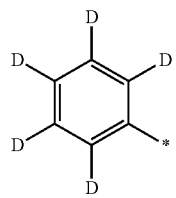

Formula 3D

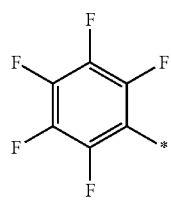

Formula 3E

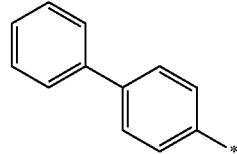

Formula 3F

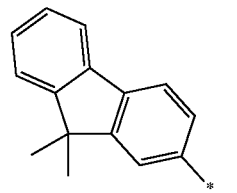

Formula 3G

Formula 3H

Formula 3I

-continued

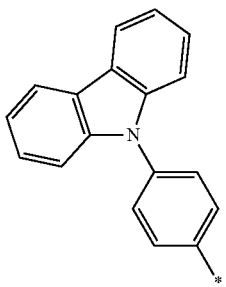
Formula 3J

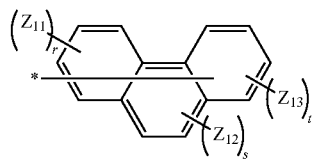
Formula 3K

In Formulae 3A through 3K above, * indicates a binding site and D is a deuterium atom.

In some embodiments of the present invention, $Ar_1$ and $Ar_2$ may be each independently selected from the group consisting of a substituted or unsubstituted phenyl group, a substituted or unsubstituted terphenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spiro-fluorenyl group, a substituted or unsubstituted dibenzothiophenyl group, a substituted or unsubstituted dibenzofuranyl group, a substituted or unsubstituted carbazolyl group, a substituted or unsubstituted pyridinyl group, a substituted or unsubstituted pyrimidinyl group, a substituted or unsubstituted triazinyl group, a substituted or unsubstituted chrysenyl group, a substituted or unsubstituted perylenyl group, and a substituted or unsubstituted oxadiazole group. Optionally, $Ar_1$ and $Ar_2$ may be linked to form a substituted or unsubstituted carbazolyl group.

In particular, each of $Ar_1$ and $Ar_2$ may be independently one of the groups represented by Formulae 4A through 4I below, but is not limited thereto:

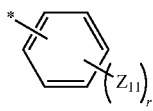
Formula 4A

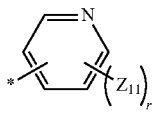
Formula 4B

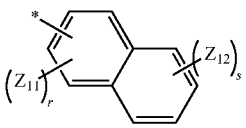
Formula 4C

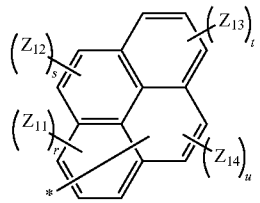
Formula 4D

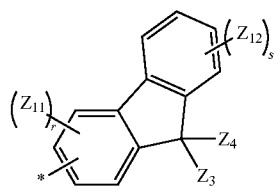
Formula 4E

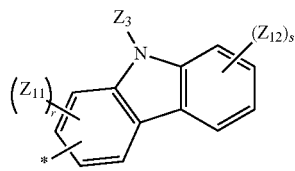
Formula 4F

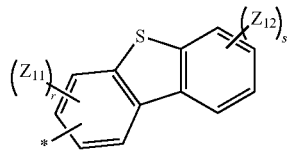
Formula 4G

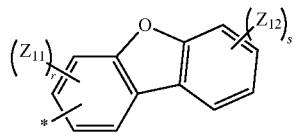
Formula 4H

Formula 4I

In Formulae 4A through 4I above, $Z_{11}$, $Z_{12}$, $Z_{13}$, and $Z_{14}$ may be each independently selected from the group consisting of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolinyl group. A plurality of $Z_{11}$, $Z_2$, $Z_{13}$, and $Z_{14}$ groups may be each independently the same as or different from each other, r and s may be each independently an integer of 1 to 5, t may be an integer of 1 to 4, u may be an integer of 1 or 2, and * indicates a binding site.

For example, each of $Ar_1$ and $Ar_2$ may be independently one of the groups represented by Formulae 5A through 5Q below:

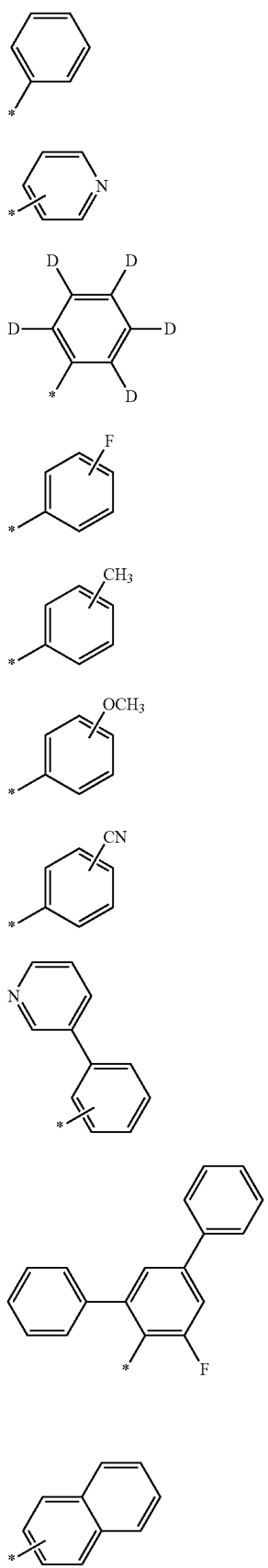
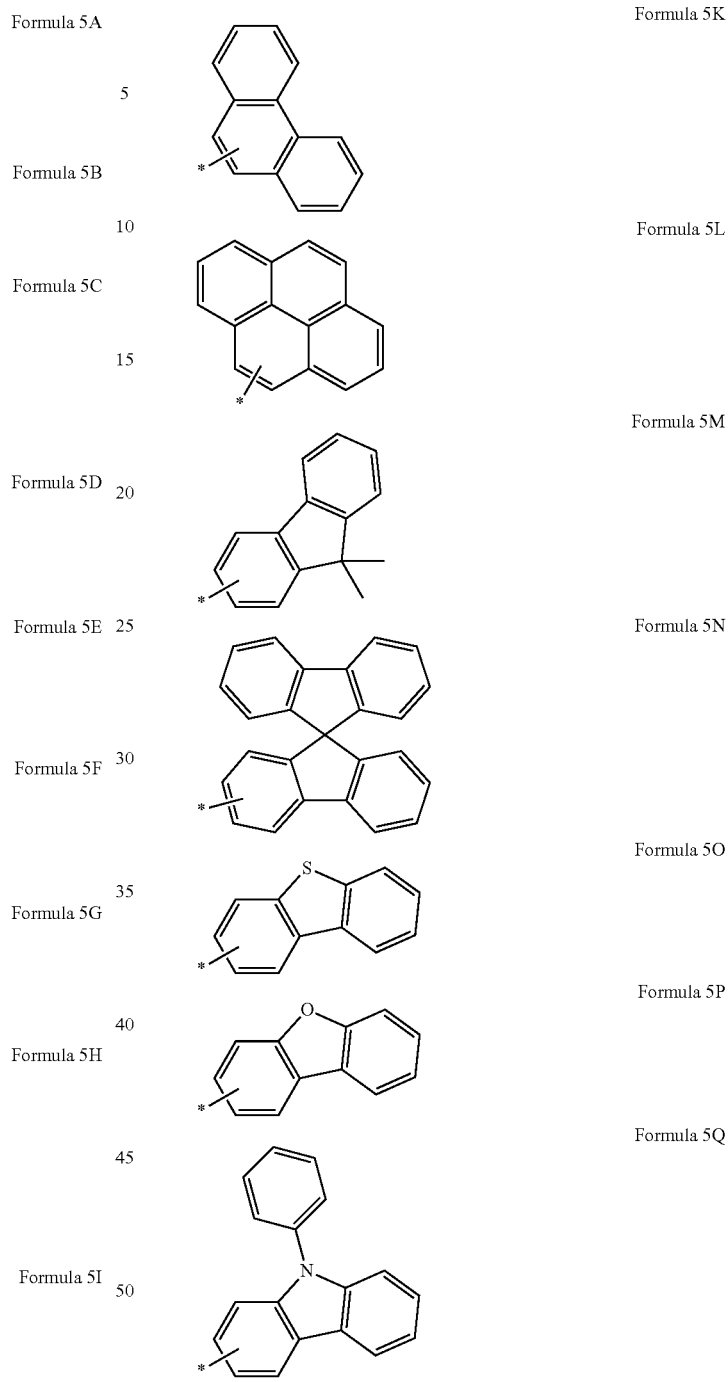

In Formulae 5A through 5Q above, * indicates a binding site and D is a deuterium atom.

In some embodiments of the present invention, A and B may be each independently selected from the group consisting of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group.

In particular, each of A and B may be independently one of the groups represented by Formulae 6A through 6K below:

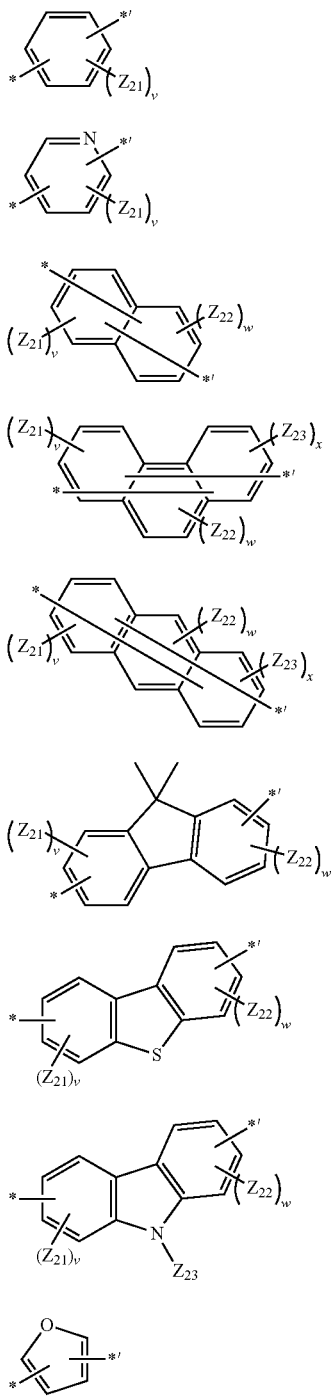

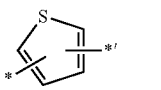

Formula 6J

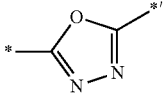

Formula 6K

In Formulae 6A through 6K, $Z_{21}$, $Z_{22}$, and $Z_{23}$ may be each independently selected from the group consisting of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, and a substituted or unsubstituted pyridinyl group. A plurality of $Z_{21}$, $Z_{22}$, and $Z_{23}$ groups may be each independently the same as or different from each other, v, w, and x may be each independently an integer of 1 to 4, and * and *' indicate binding sites.

For example, each of A and B may be independently one of the groups represented by Formulae 7A through 7N below:

Formula 7A

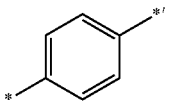

Formula 7B

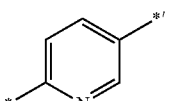

Formula 7C

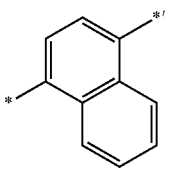

Formula 7D

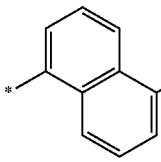

Formula 7E

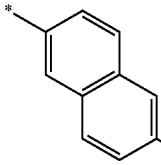

Formula 7F

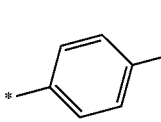

Formula 7G
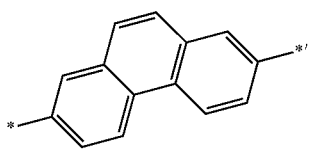
Formula 7H
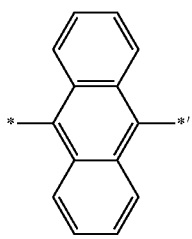
Formula 7I
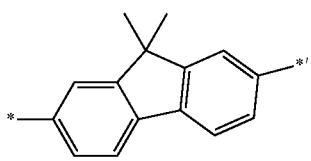
Formula 7J
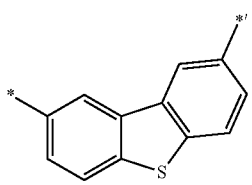
Formula 7K
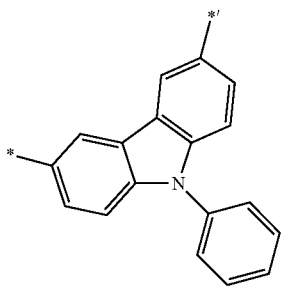
Formula 7L
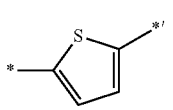
Formula 7M
Formula 7N
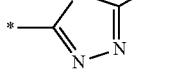
In Formulae 7A through 7N above, * and *' indicate binding sites.
The heterocyclic compound represented by Formula I may be one of Compounds 1 through 80 below, but is not limited thereto:
1
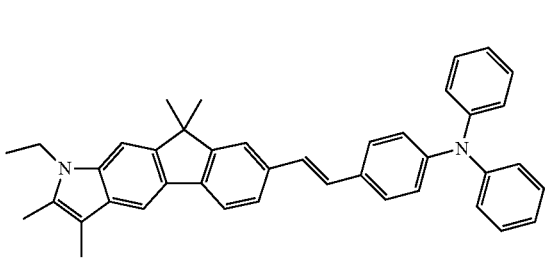
2
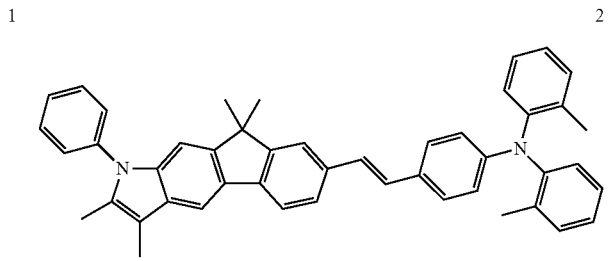
3
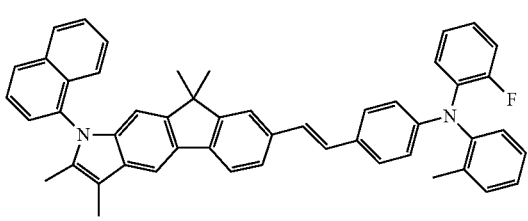
4
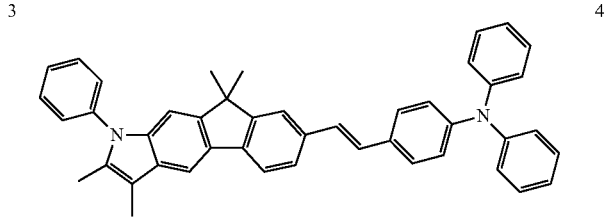
5
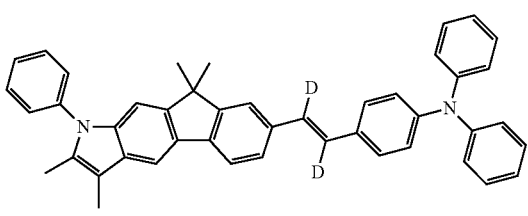
6
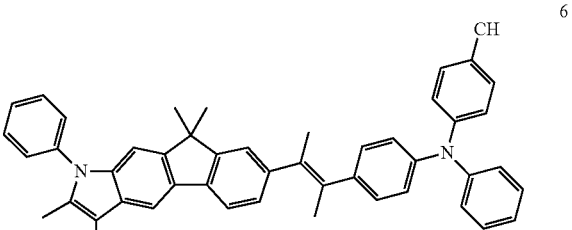

-continued
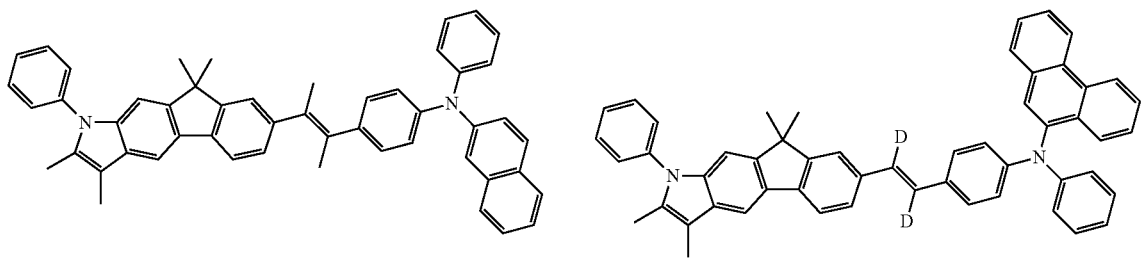
7
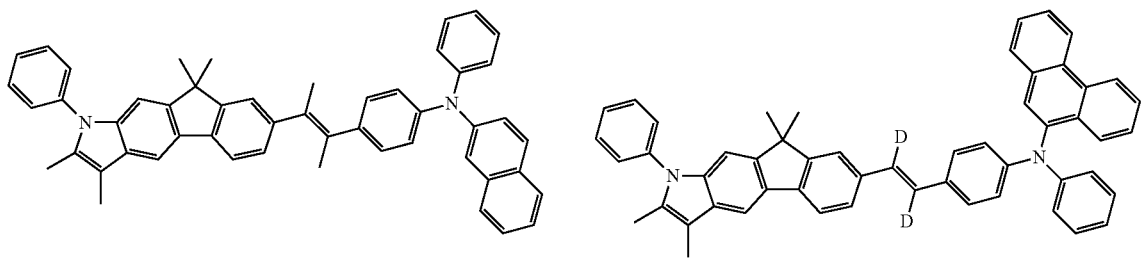
8
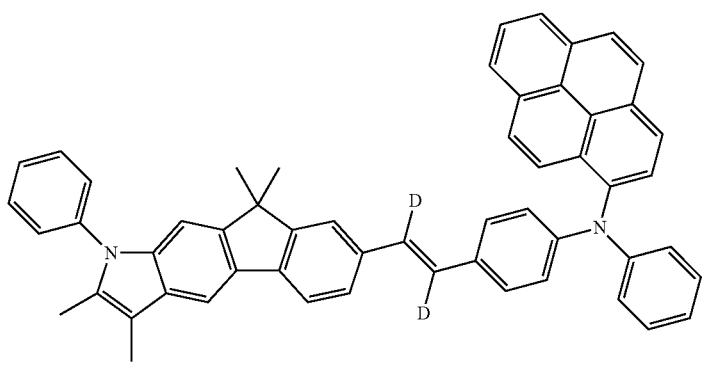
9
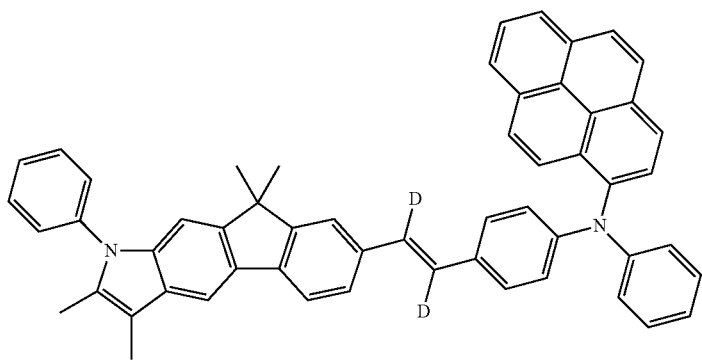
9
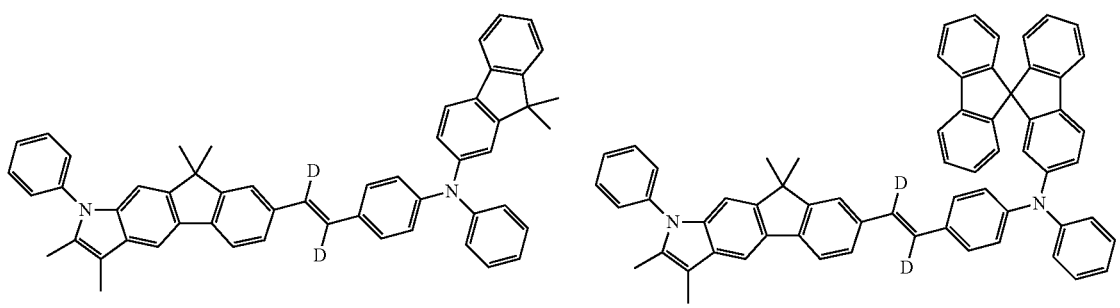
10
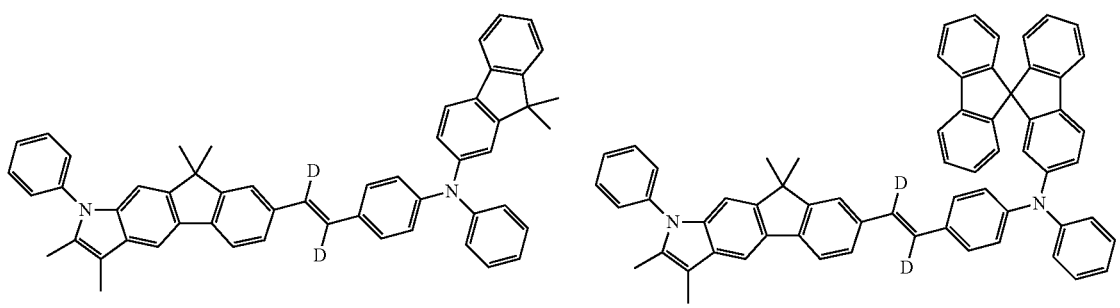
11

-continued
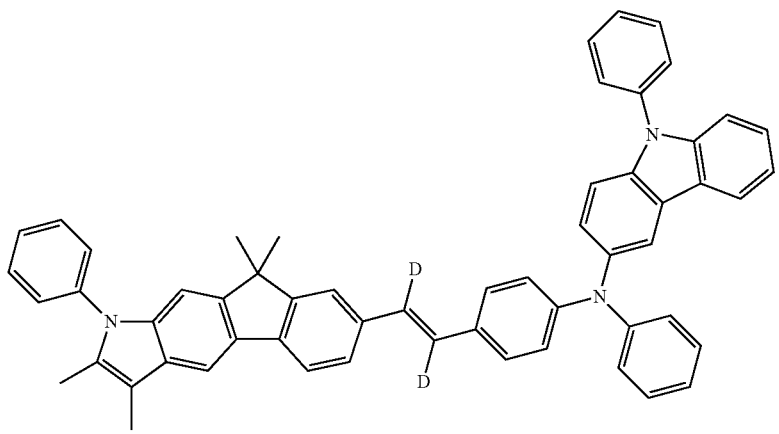
12
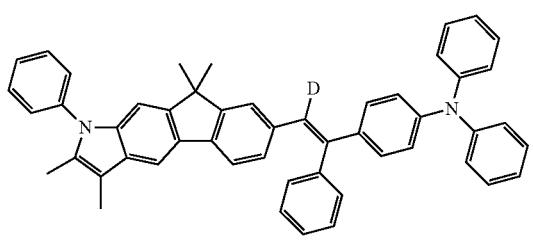
13
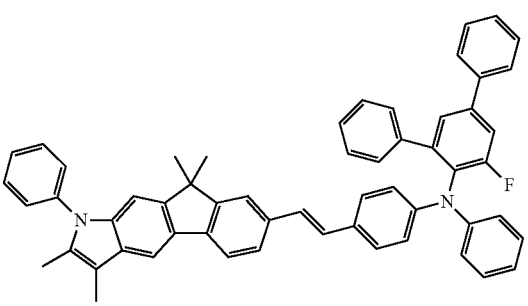
14
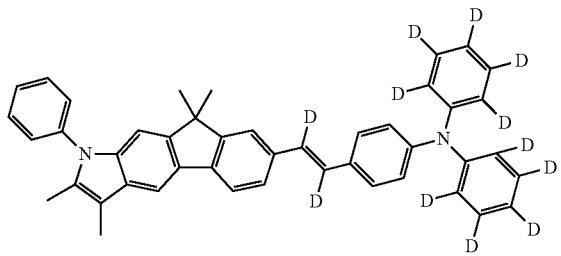
15
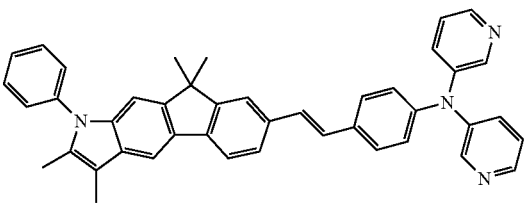
16
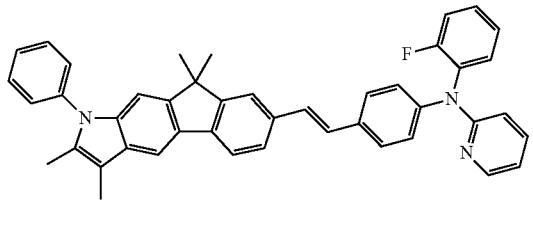
17
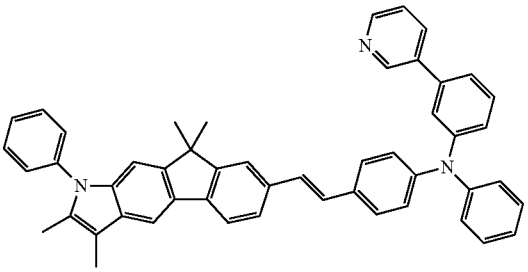
18
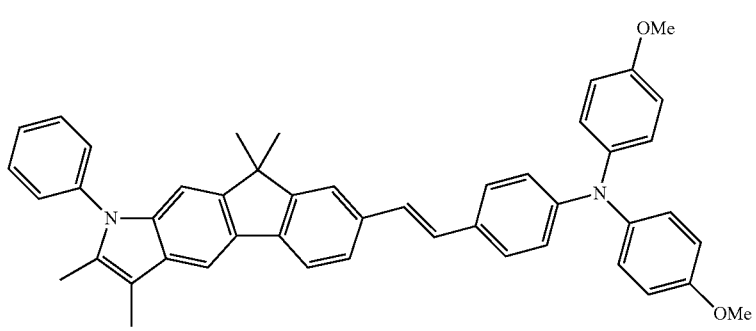
19

-continued
20
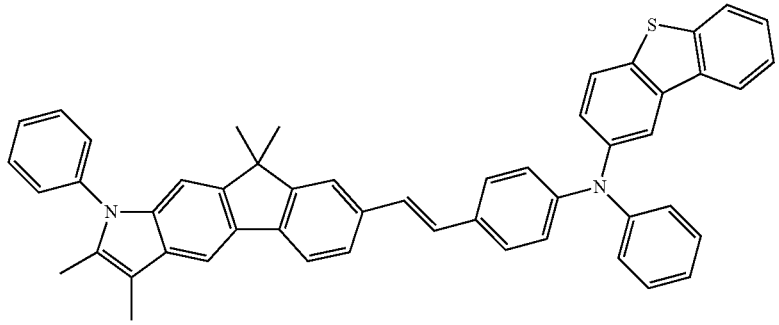
21
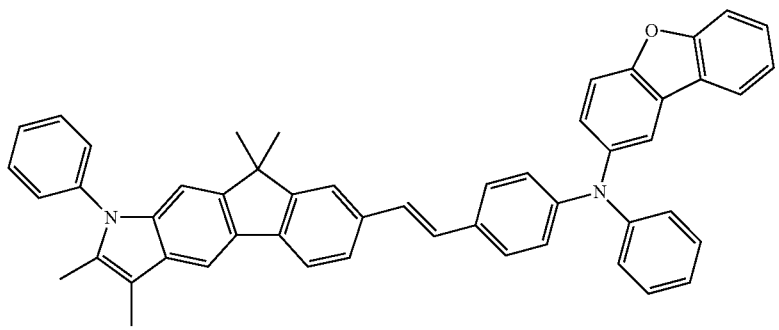
22
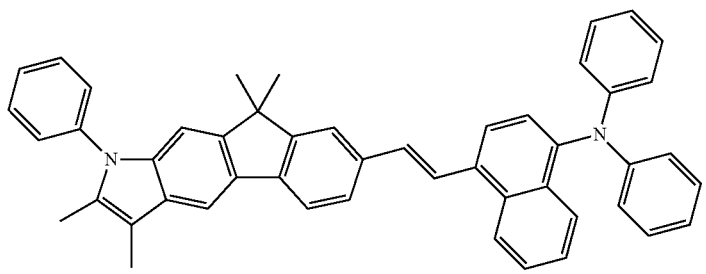
23
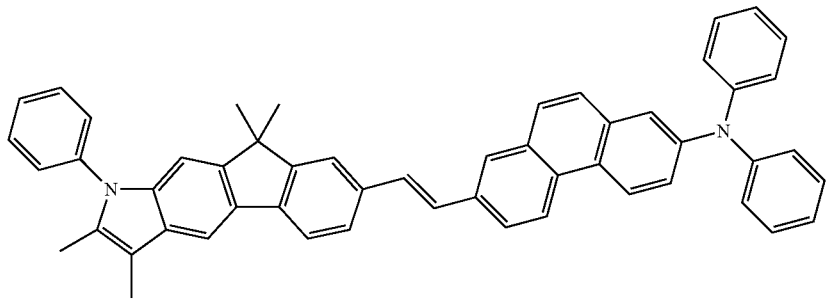
24
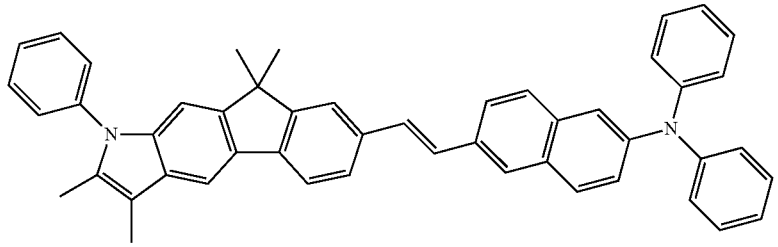

-continued
25
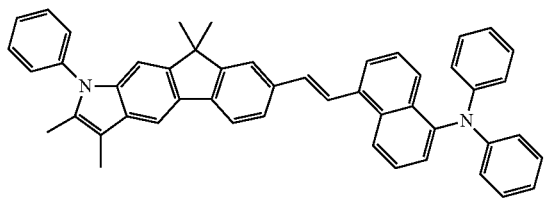
26
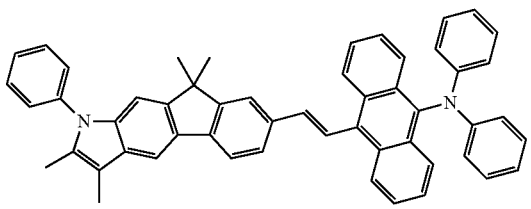
27
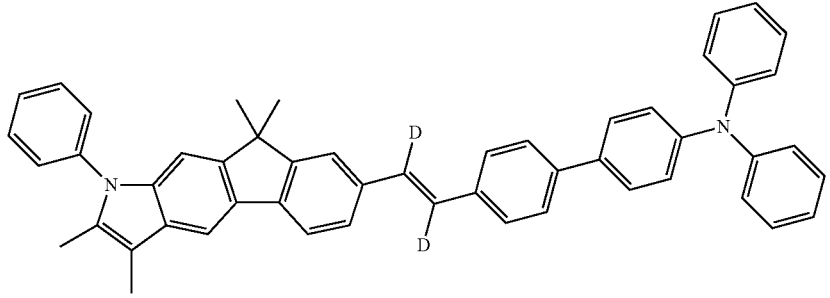
28
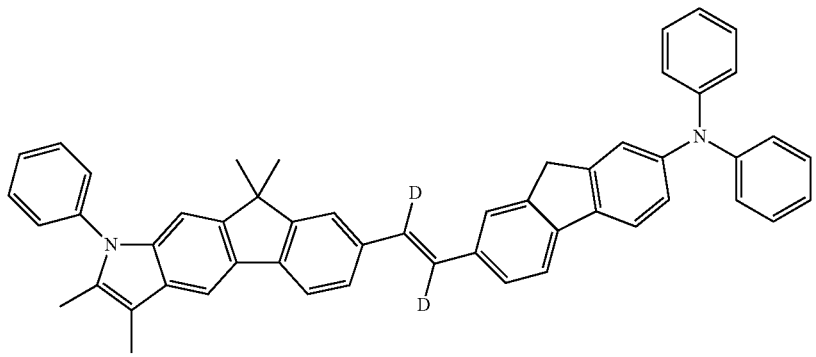
29
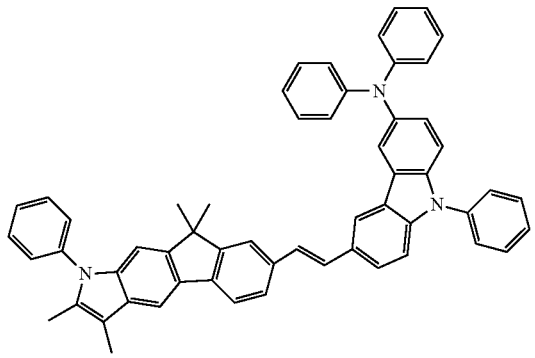
30
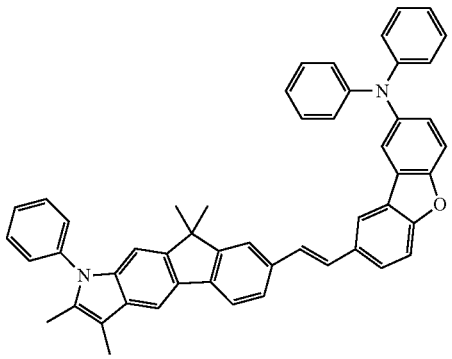
31
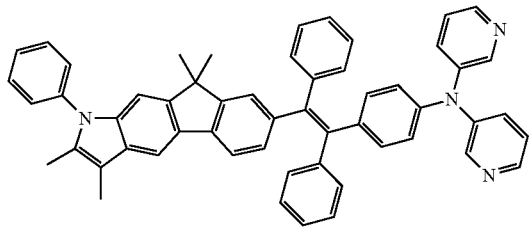
32
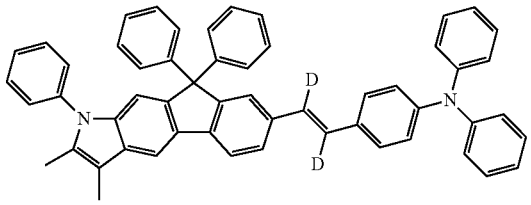

-continued
33
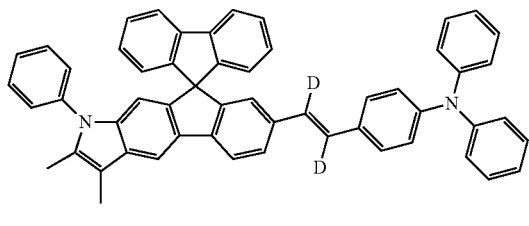
34
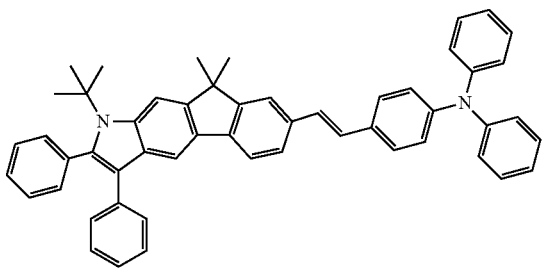
35
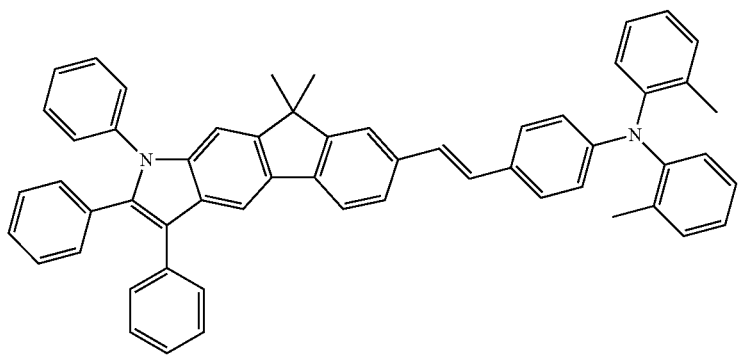
36
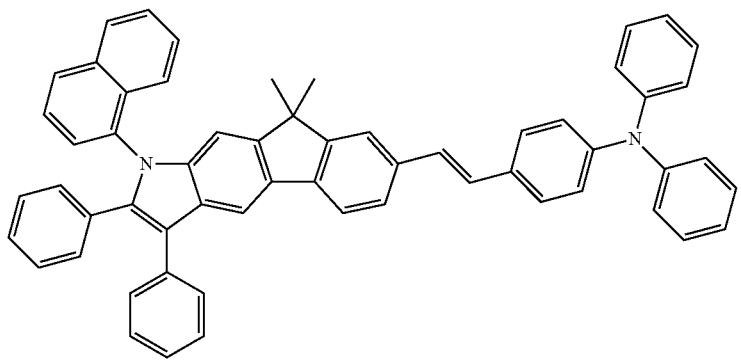
37
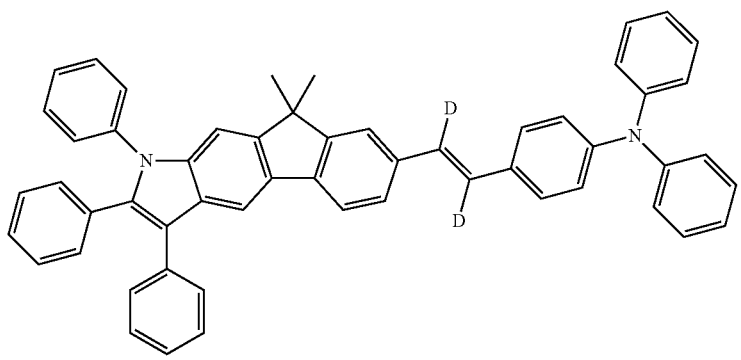

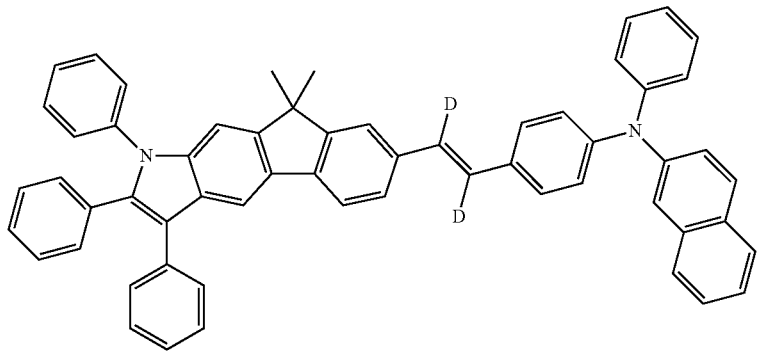
38
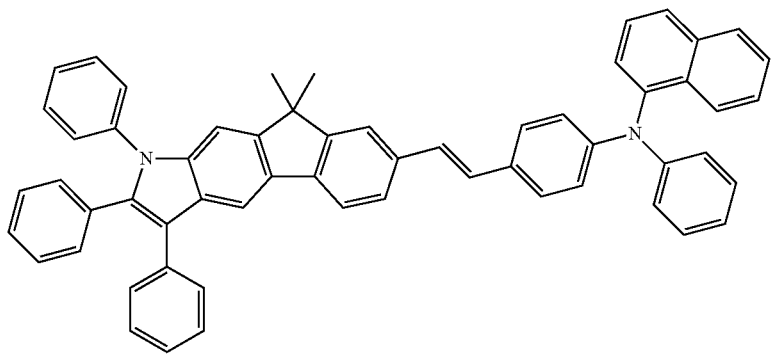
39
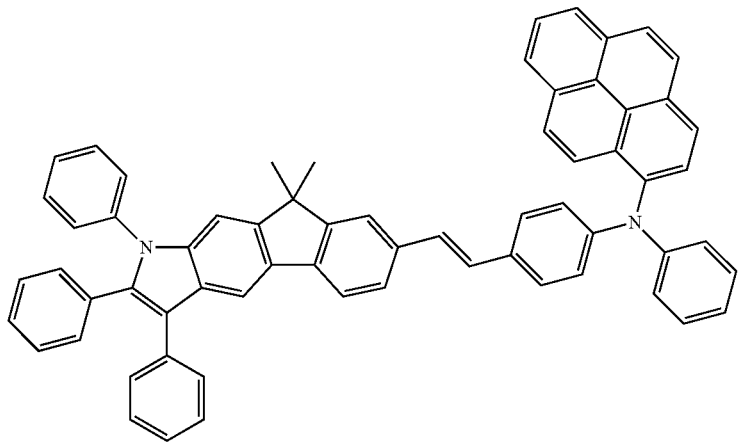
40
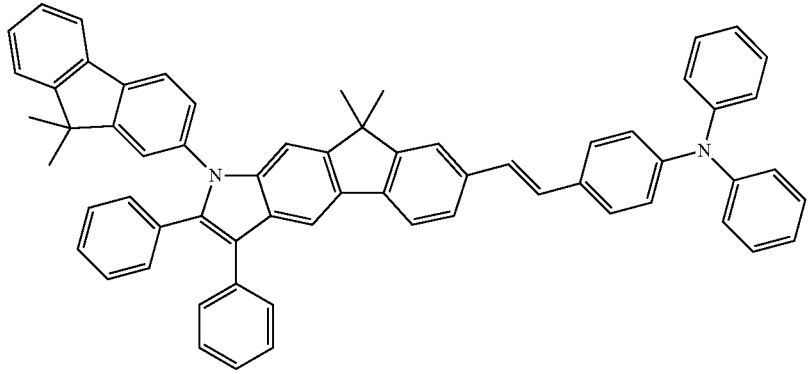
41

42
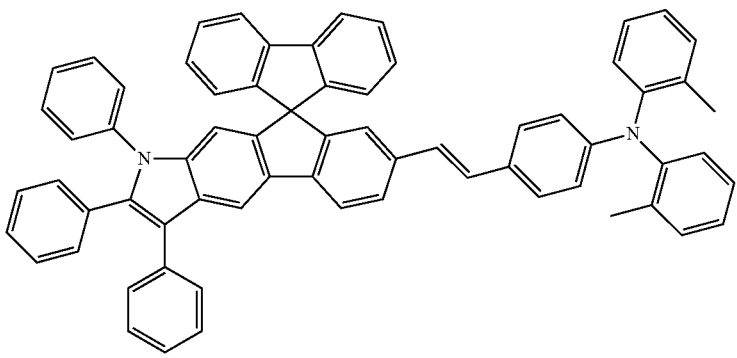
43
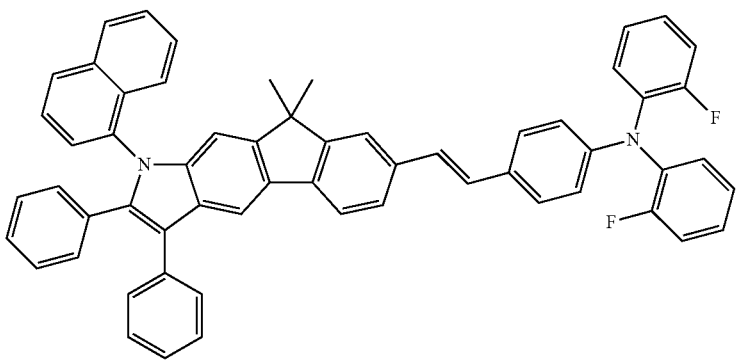
44
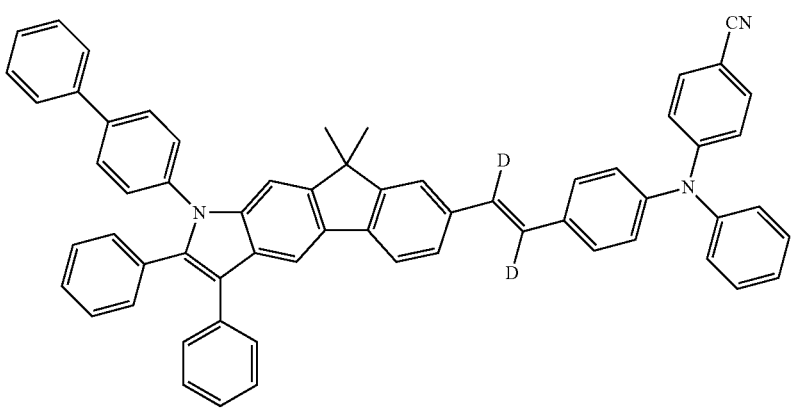
45
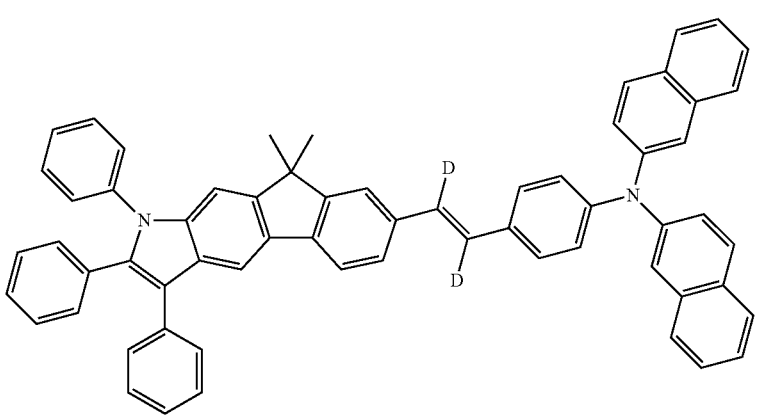

46
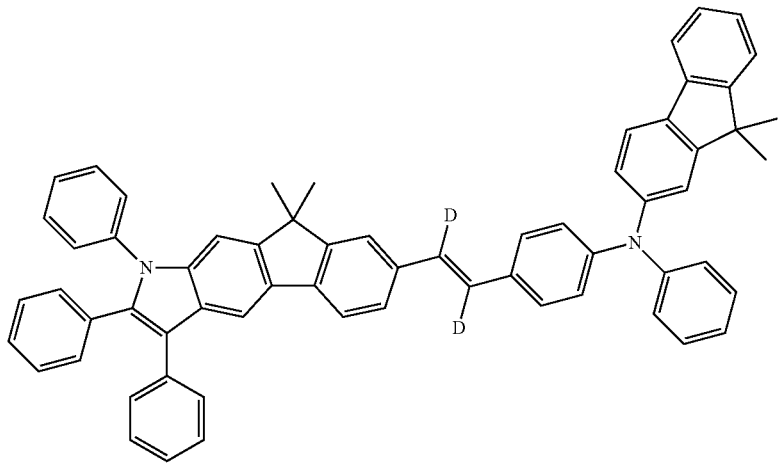
47
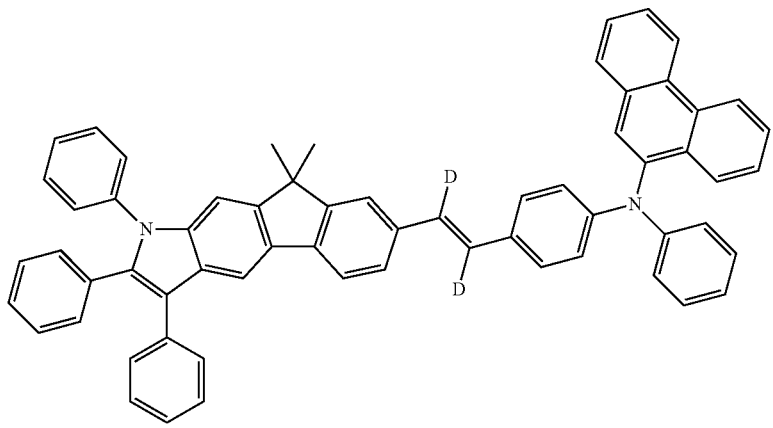
48
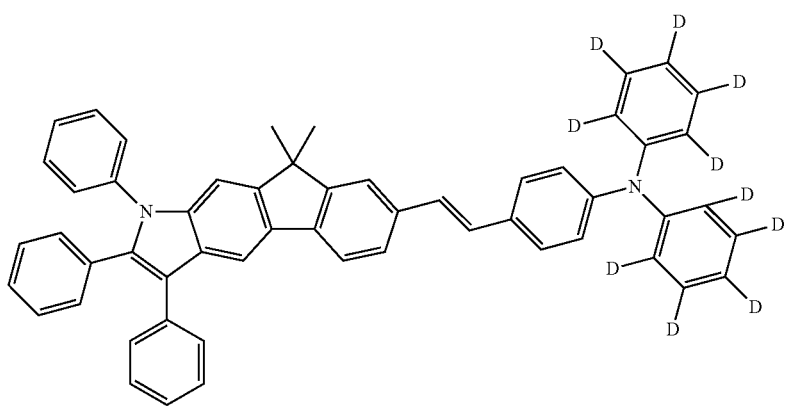

-continued
49
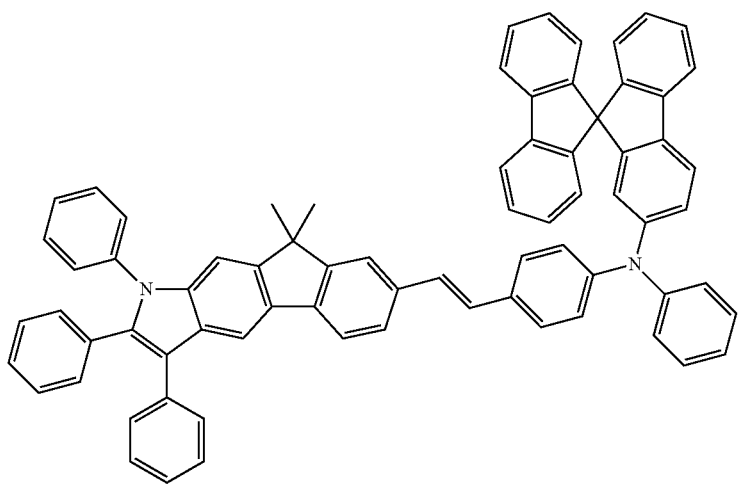
50
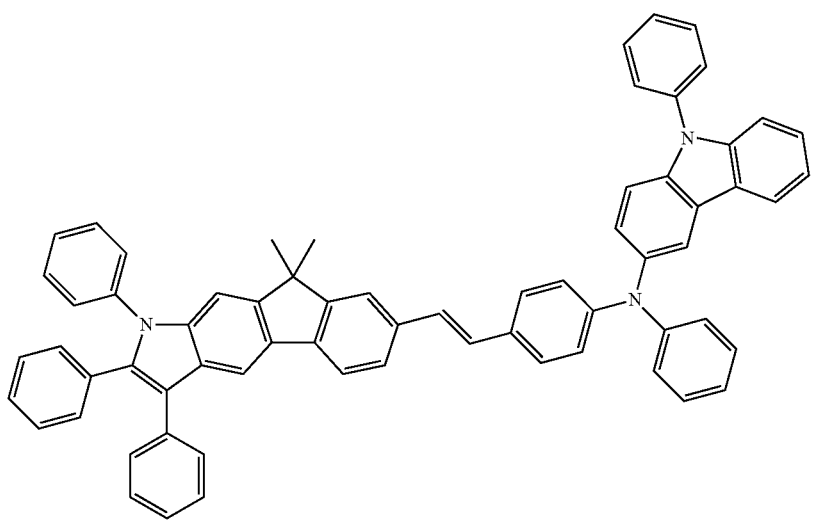
51
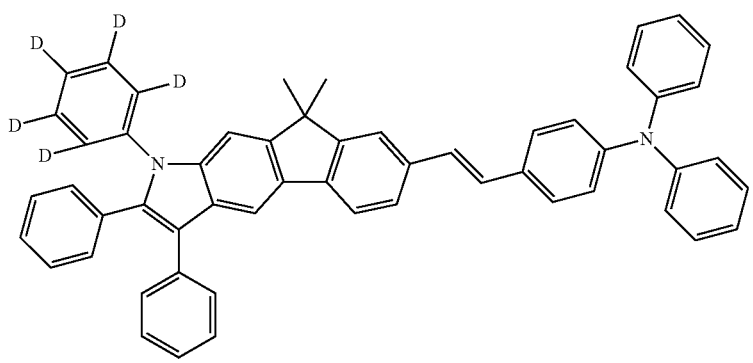

-continued
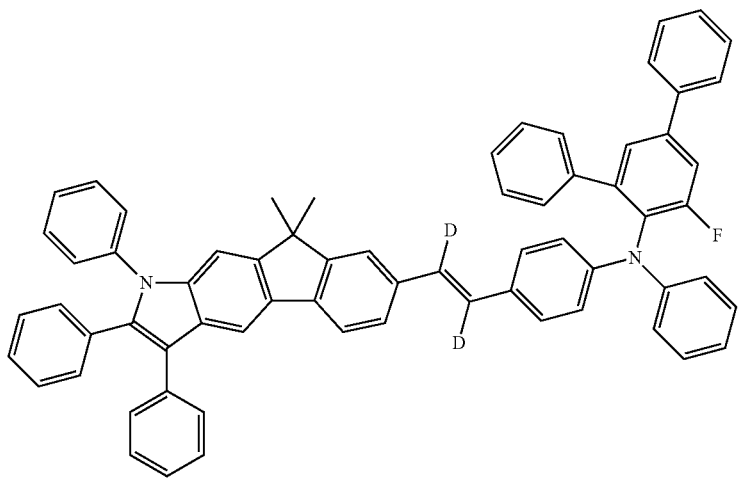
52
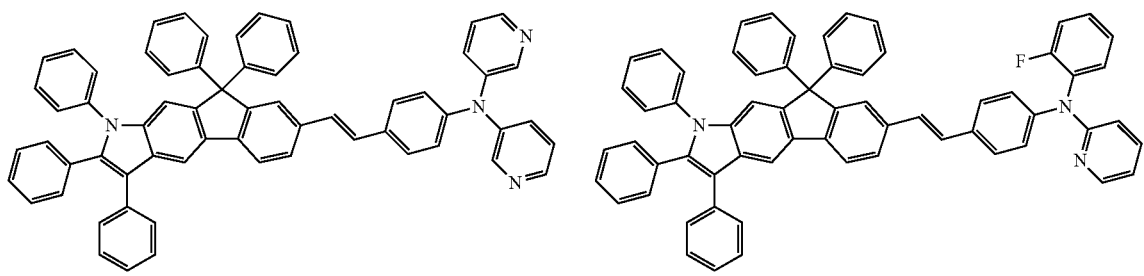
53 54
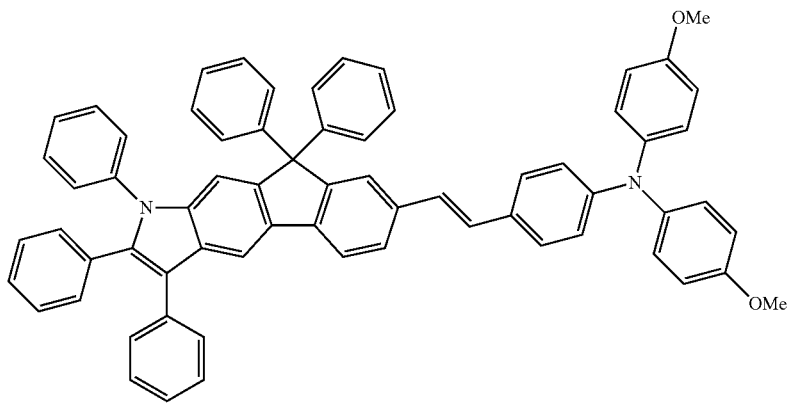
55
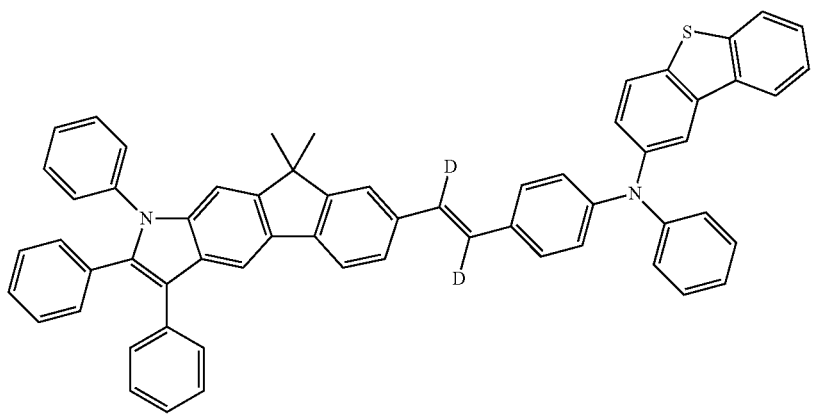
56

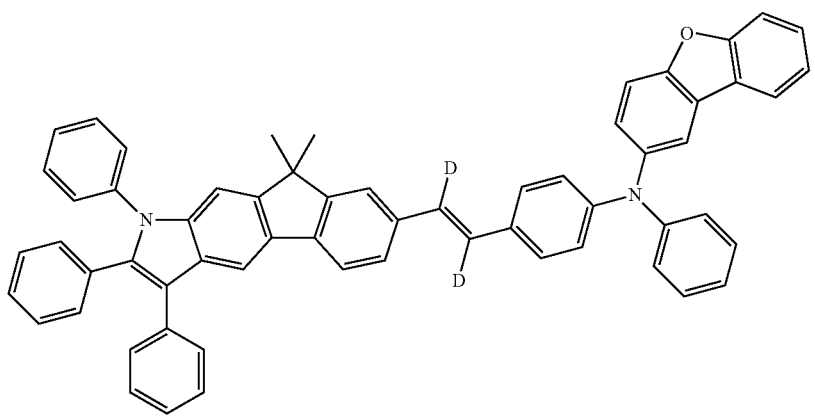
57
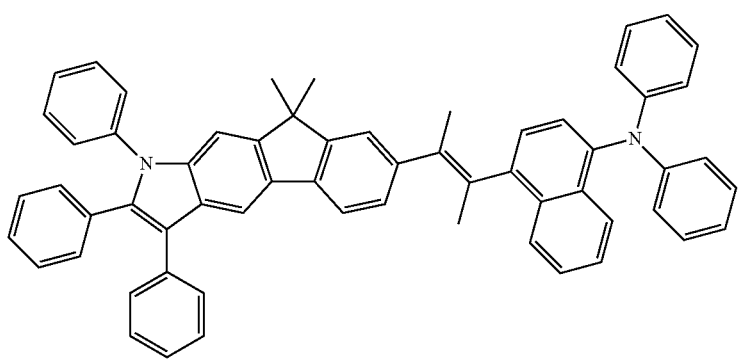
58
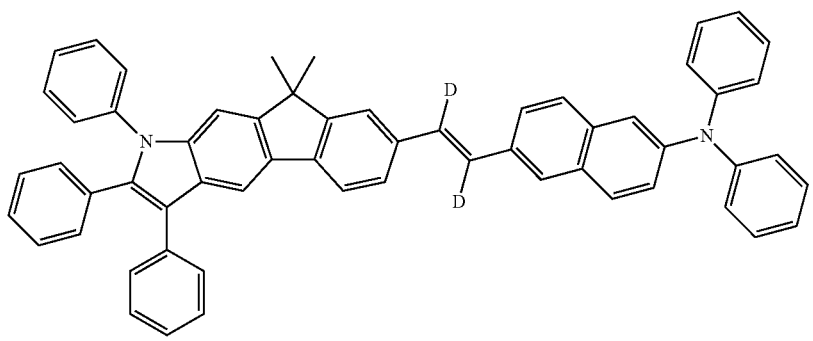
59
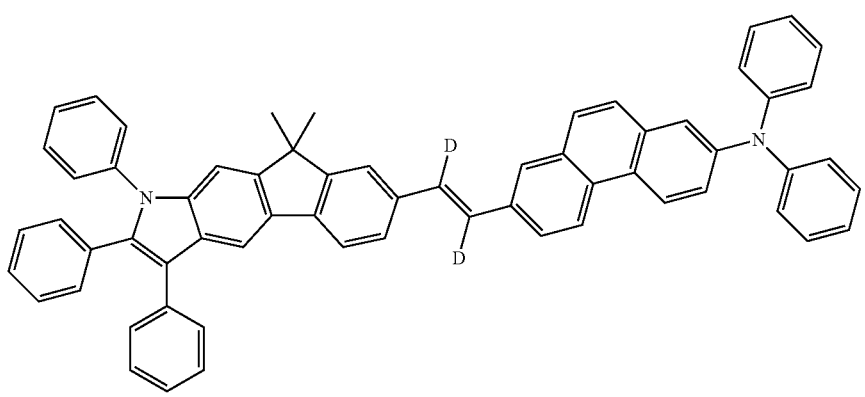
60

61
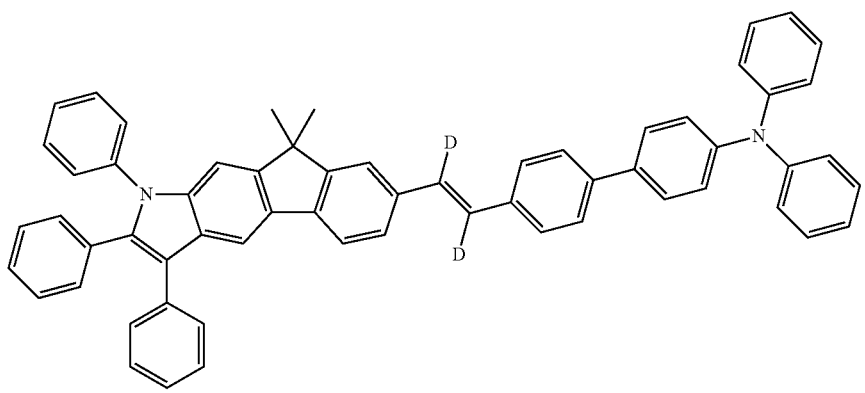
62
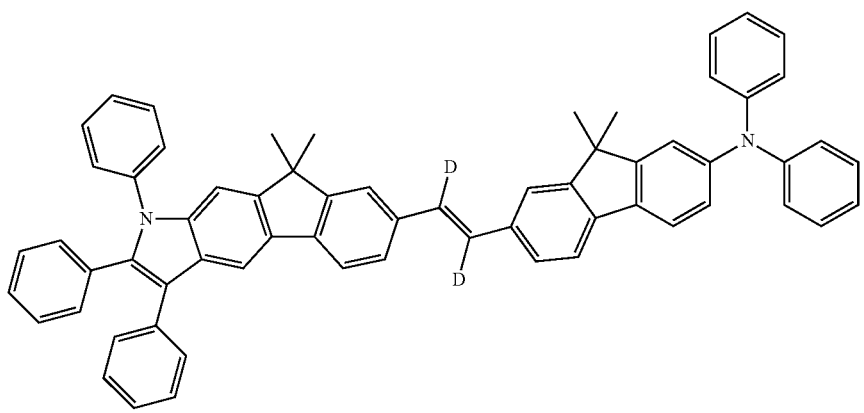
63
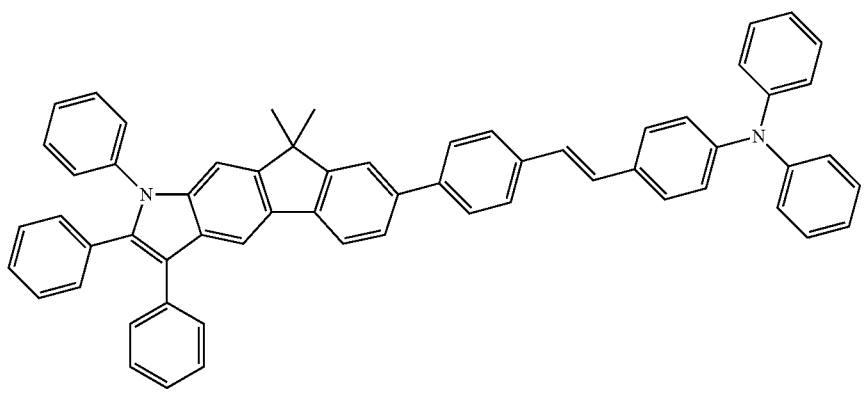
64
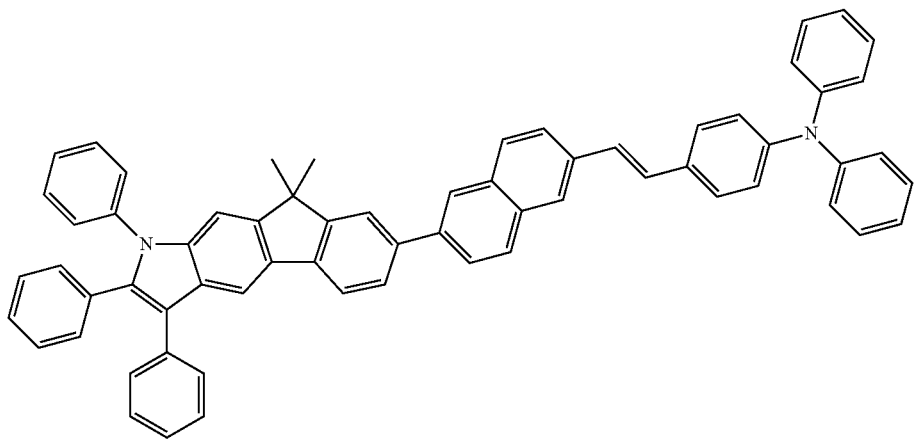

65
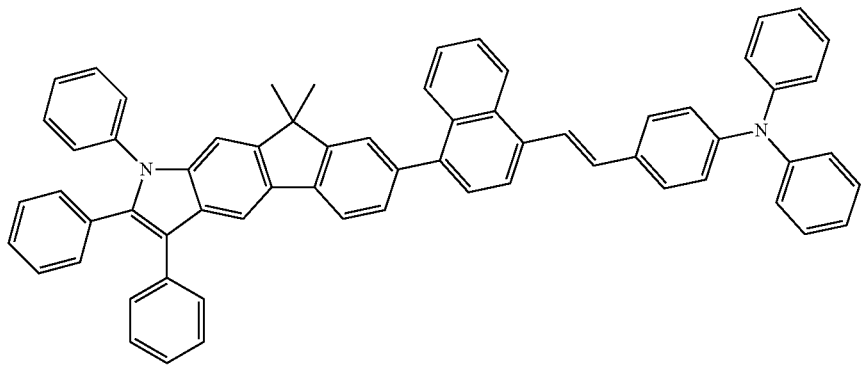
66
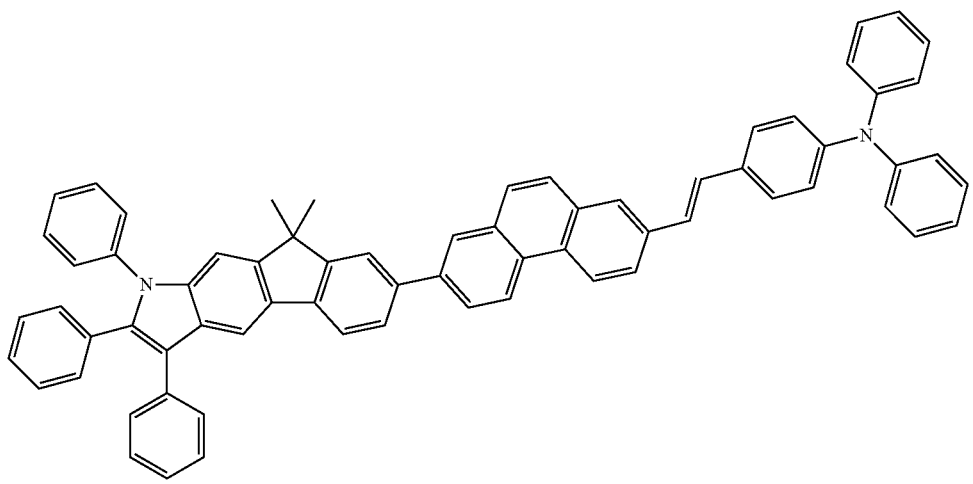
67
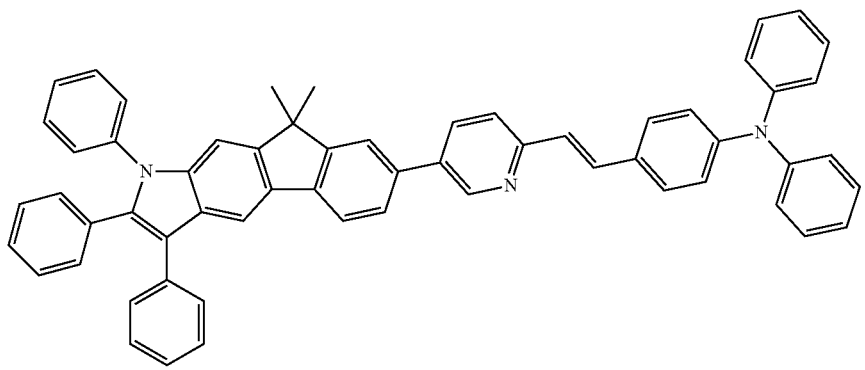
68
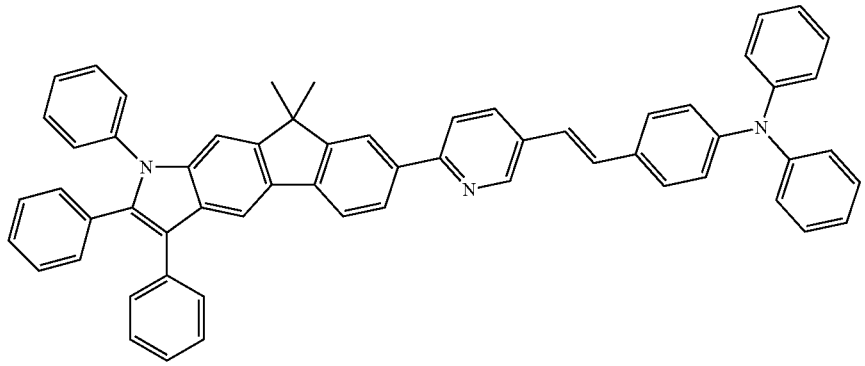

-continued
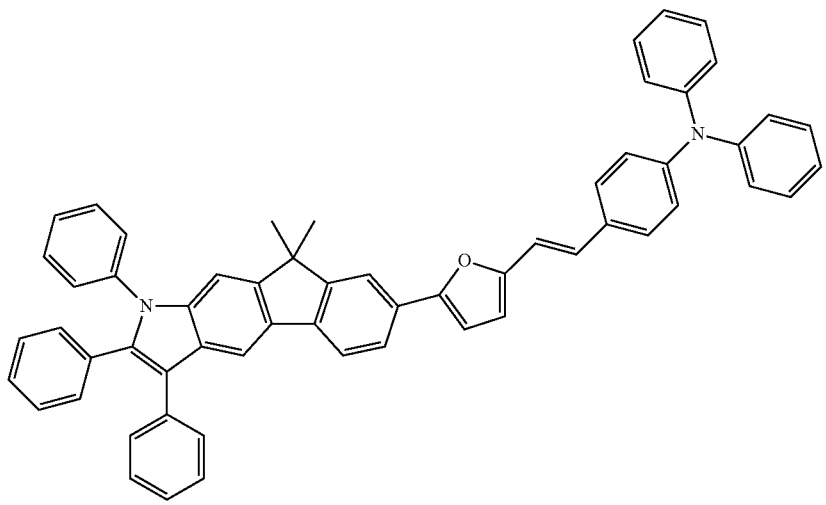
69
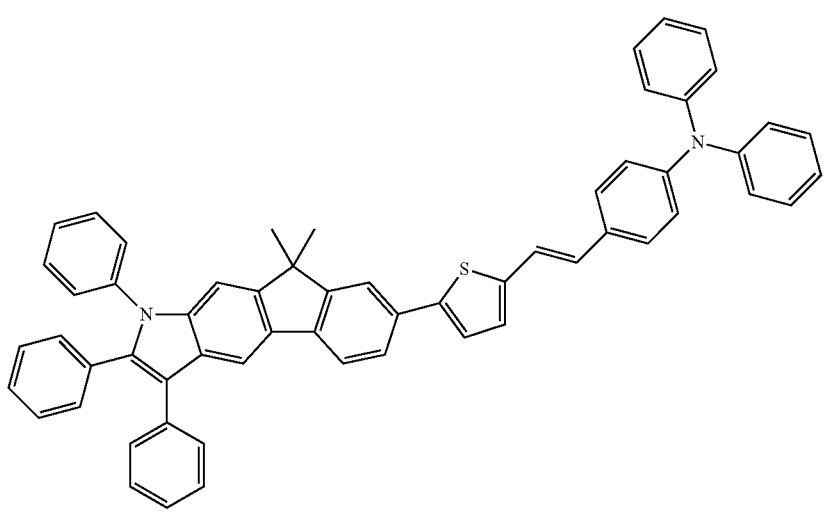
70
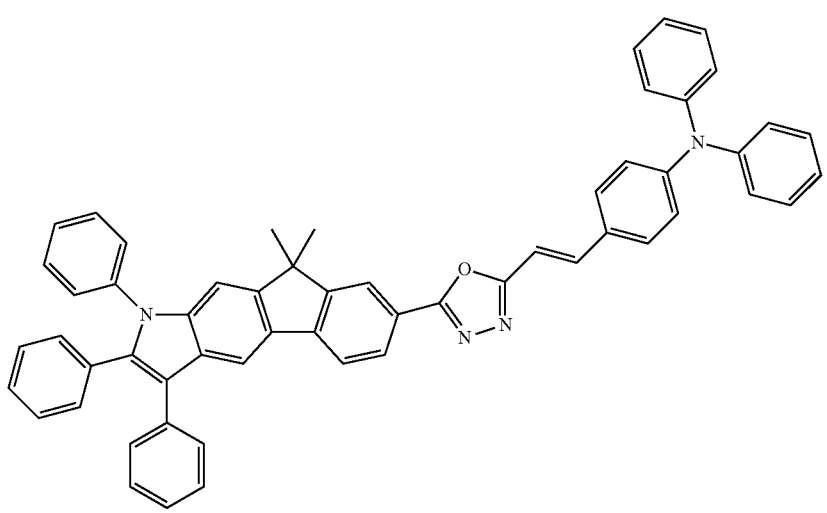
71

-continued
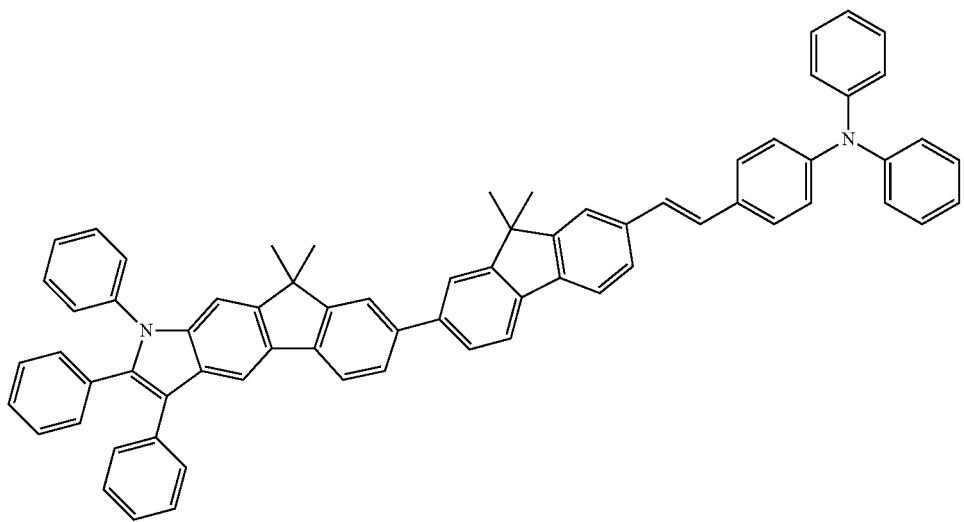
72
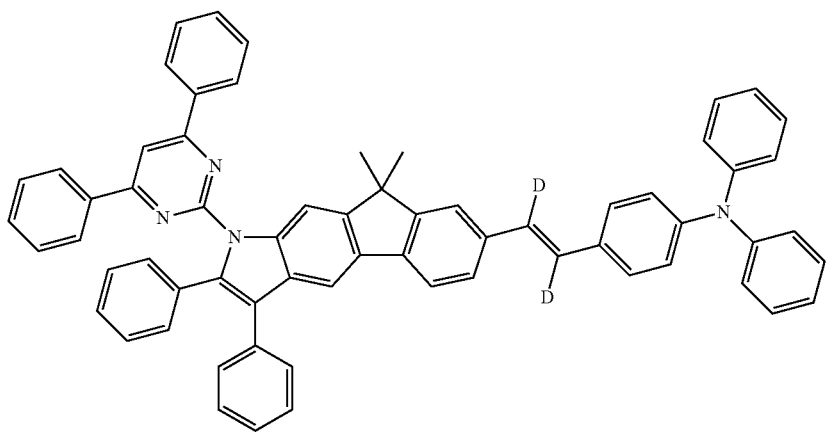
73
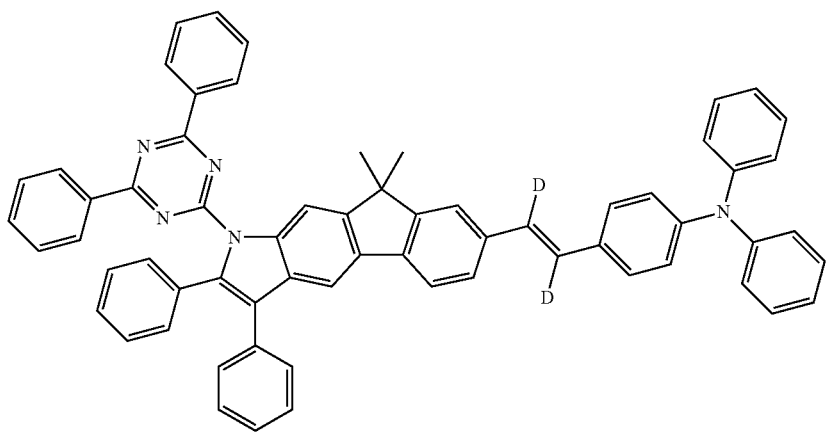
74

75
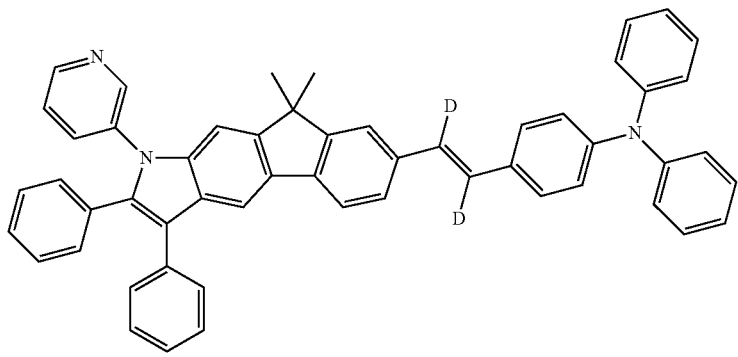
76
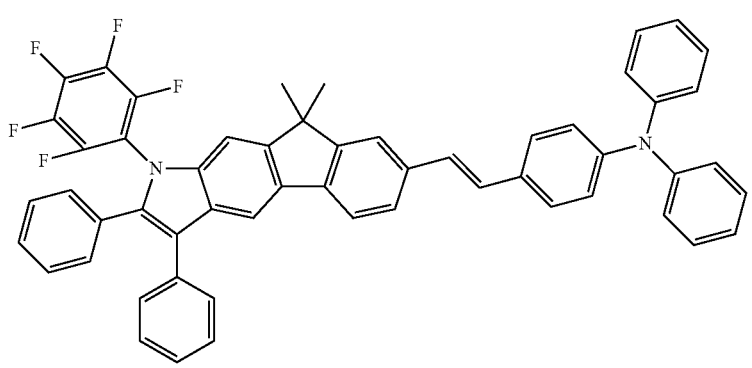
77
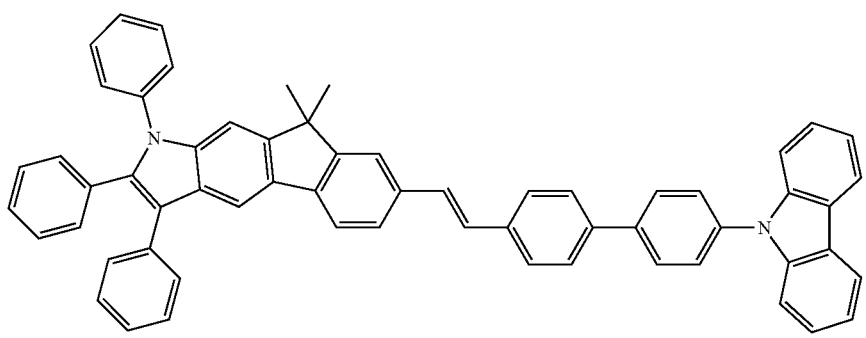
78
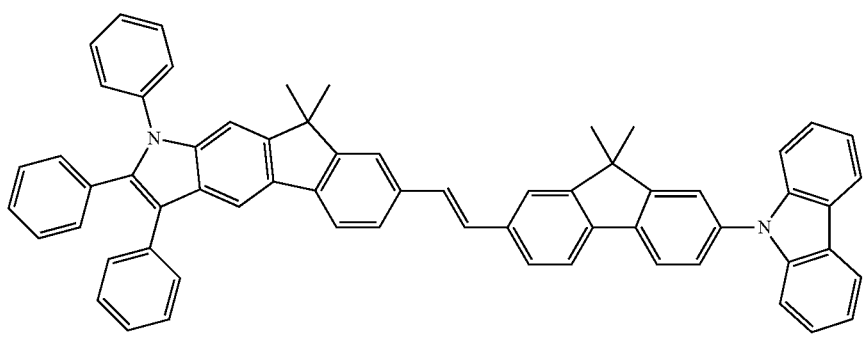

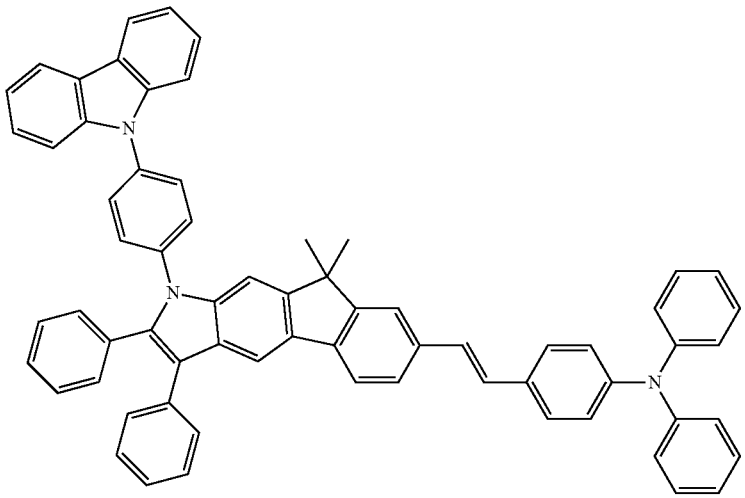

79

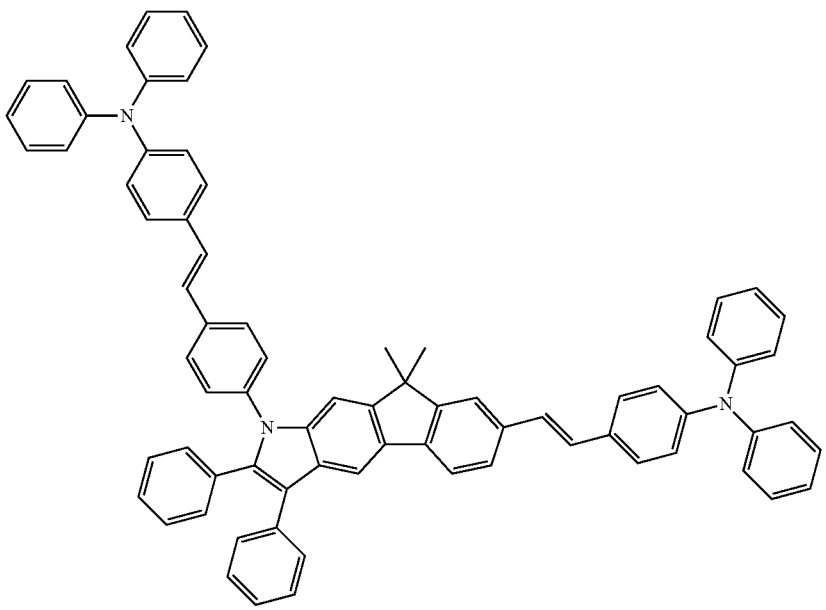

80

The heterocyclic compounds represented by Formula 1 may be used as at least one of an emitting material, a hole injecting material and hole transporting material for an OLED. In addition, the heterocyclic compounds of Formula 1 containing a heterocyclic group in molecules have a high glass transition temperature Tg and a high melting point thanks to the introduction of the heterocyclic group. Thus, during electroluminescence, heat resistance to Joule's heat produced inside organic layers, between organic layers, or between an organic layer and a metal electrode is increased, and resistance to high temperature environments is increased. In addition, when a substituent such as a fluorene group is introduced into the heterocyclic compound of Formula 1, the morphology of an organic layer including the heterocyclic compound of Formula 1 is improved so that an OLED including the organic layer may have enhanced characteristics.

The term "substituted A" in "substituted or unsubstituted A (A is a certain substituent)" used herein indicates that at least one hydrogen atom of A is substituted with one substituent selected from the group consisting of a deuterium atom, a halogen atom, a hydroxyl group, a cyano group, a nitro group, an amino group, hydrazine, hydrazone, a carboxyl group or a salt derivative thereof, a sulfonic acid group or a salt derivative thereof, a phosphoric acid group or a salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, a $C_3$-$C_{30}$ heteroaryl group, a group represented by $N(Q_{101})(Q_{102})$, and a group represented by $Si(Q_{103})(Q_{104})(Q_{105})$. In this regard, $Q_{101}$ through $Q_{105}$ may be each independently a hydrogen atom, a deuterium atom, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, or a $C_3$-$C_{30}$ heteroaryl group.

For example, the term "substituted A" used herein indicates that at least one hydrogen atom of A is substituted with one selected from the group consisting of a deuterium atom, a halogen atom, a hydroxyl group, a cyano group, a nitro group, a carboxyl group, a methyl group, an ethyl group, a propyl group, a butyl group, a pentyl group, a methoxy group, an ethoxy group, a phenyl group, a biphenyl group, a pentalenyl group, an indenyl group, a naphthyl group, an azulenyl group, a heptalenyl group, an indacenyl group, an acenaphtyl group, a fluorenyl group, a spiro-fluorenyl group, a phenalenyl group, a phenanthrenyl group, a It phenanthridinyl group, a phenanthrolinyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a benzoimidazolyl group, a pyrazolyl group, a pyridinyl group, a pyrazinyl group, a pyrimidinyl group, an imidapyrimidinyl group, a pyridazinyl group, an indolyl group, an isoindolyl group, a pyridoindolyl group, an indazolyl group, a purinyl group, a quinolinyl group, a benzoquinolinyl group, a phthalazinyl group, a naphthyridinyl group, a quinoxalinyl group, a quinazolinyl group, a carbazolyl group, a phenazinyl group, a furanyl group, a benzofuranyl group, a dibenzofuranyl group, a thiophenyl group, a benzothiophenyl group, a dibenzothiophenyl group, a thiazolyl group, an isothiazolyl group, a benzothiazolyl group, an oxazolyl group, a henzooxazolyl group, an isoxazolyl group, an oxadiazolyl group, a triazolyl group, a triazinyl group, a tetrazolyl group, a group represented by $N(Q_{101})(Q_{107})$, and a group represented by $Si(Q_{103})(Q_{104})(Q_{105})$.

The unsubstituted $C_1$-$C_{30}$ alkyl group denotes a saturated hydrocarbon group having a linear and branched structure in which one hydrogen atom is lacking in alkane. Examples of the unsubstituted $C_1$-$C_{30}$ alkyl group may include methyl, ethyl, propyl, isobutyl, sec-butyl, pentyl, iso-amyl, hexyl, and the like. A detailed description of a substituent of the substituted $C_1$-$C_{30}$ alkyl group is already provided in the description for the "substituted A."

The unsubstituted $C_2$-$C_{30}$ alkenyl group denotes a terminal group containing at least one carbon double bond at the middle or the end of the unsubstituted $C_2$-$C_{30}$ alkyl group. Examples of the unsubstituted $C_2$-$C_{30}$ alkenyl group may include ethenyl, prophenyl, butenyl, pentenyl, hexenyl, heptenyl, octenyl, propadienyl, isoprenyl, allyl, and the like. A detailed description of a substituent of the substituted $C_2$-$C_{30}$ alkenyl group is already provided in the description for the "substituted A."

The unsubstituted $C_2$-$C_{30}$ alkynyl group denotes a terminal group containing at least one carbon triple bond at the middle or the end of the unsubstituted $C_2$-$C_{60}$ alkyl group. Examples of the unsubstituted $C_2$-$C_{30}$ alkynyl group may include ethynyl, propynyl, acetylenyl, and the like. A detailed description of a substituent of the substituted $C_2$-$C_{30}$ alkynyl group is already provided in the description for the "substituted A."

The unsubstituted $C_1$-$C_{30}$ alkoxy group has a Formula of —OY (Y is the unsubstituted $C_1$-$C_{30}$ alkyl group) and may be, for example, a methoxy group, ethoxy group, isopropyloxy group, butoxy group, pentoxy group, and the like. A detailed description of a substituent of the substituted $C_1$-$C_{30}$ alkoxy group is already provided in the description for the "substituted A."

The unsubstituted $C_3$-$C_{30}$ cycloalkyl group denotes a ring-type saturated hydrocarbon group and may be, for example, cyclopropyl, cyclobutyl, cyclopentyl, cyclohexyl, cyclooctyl, and the like. A detailed description of a substituent of the substituted $C_3$-$C_{30}$ cycloalkyl group is already provided in the description for the "substituted A."

The unsubstituted $C_3$-$C_{30}$ cycloalkenyl group denotes a ring-type unsaturated hydrocarbon group which has at least one carbon double bond and is not an aromatic ring. Examples of the unsubstituted $C_3$-$C_{30}$ cycloalkenyl group may include cyclopropenyl, cyclobutenyl, cyclopentenyl, cyclohexenyl, cycloheptenyl, a 1,3-cyclohexadienyl group, a 1,4-cyclohexadienyl group, a 2,4-cycloheptadienyl group, a 1,5-cyclooctadienyl group, and the like. A detailed description of a substituent of the substituted $C_3$-$C_{60}$ cycloalkenyl group is already provided in the description for the "substituted A."

The unsubstituted $C_5$-$C_{30}$ aryl group denotes a monovalent group having a $C_5$-$C_{30}$ carbocyclic aromatic system, wherein the monovalent group may be a monocyclic or polycyclic group. In the polycyclic group, at least two rings included therein may be fused with each other. Examples of the unsubstituted $C_5$-$C_{30}$ aryl group may include phenyl, pentalenyl, indenyl, naphtyl, azulenyl, heptalenyl, indacenyl, acenaphtyl, fluorenyl, Spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, hexacenyl, and the like. A detailed description of a substituent of the substituted $C_5$-$C_{30}$ aryl group is already provided in the description for the "substituted A."

The unsubstituted $C_5$-$C_{30}$ aryloxy group denotes a monovalent group, to which carbon atoms of the $C_5$-$C_{30}$ aryl group are attached through an oxygen linking group (—O—). A detailed description of a substituent of the substituted $C_5$-$C_{30}$ aryloxy group is already provided in the description for the "substituted A."

The unsubstituted $C_5$-$C_{30}$ arylthio group denotes a monovalent group, to which carbon atoms of the $C_5$-$C_{30}$ aryl group are attached through a sulfur linking group (—S—). Examples of the unsubstituted $C_5$-$C_{30}$ arylthio group may include phenylthio, naphtylthio, indanylthio, and indenylthio. A detailed description of a substituent of the substituted $C_5$-$C_{30}$ arylthio group is already provided in the description for the "substituted A."

The unsubstituted $C_3$-$C_{30}$ heteroaryl group denotes a monovalent group including at least one ring containing at least one heteroatom selected from the group consisting of N, O, P, and S, wherein the monovalent group is a monocyclic or polycyclic group. In the polycyclic group, at least two rings included therein may be fused with each other. Examples of the unsubstituted $C_3$-$C_{30}$ heteroaryl group may include pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolyl, triazinyl, benzooxazolyl, and the like. A detailed description of a substituent of the substituted $C_3$-$C_{30}$ heteroaryl group is already provided in the description for the "substituted A."

The unsubstituted $C_1$-$C_{30}$ alkylene group denotes a divalent group having a linear and branched structure, in which two hydrogen atoms are lacking in alkane. Examples of the unsubstituted $C_1$-$C_{30}$ alkylene group are already provided in the description with regards to the unsubstituted $C_1$-$C_{30}$ alkyl group. A detailed description of a substituent of the substituted $C_1$-$C_{30}$ alkylene group is already provided in the description for the "substituted A."

The unsubstituted $C_5$-$C_{30}$ arylene group may denote a divalent group having a $C_5$-$C_{30}$ carbocyclic aromatic system, wherein the divalent group may be a monocyclic or polycyclic group. Examples of the unsubstituted $C_5$-$C_{30}$ arylene group are already provided in the description with regards to the unsubstituted $C_5$-$C_{30}$ aryl group. A detailed description of a substituent of the substituted $C_5$-$C_{30}$ arylene group is already provided in the description for the "substituted A."

The heterocyclic compound of Formula 1 may be synthesized using a known organic synthesis method. The synthesis of the heterocyclic compound may be easily understood by one of ordinary skill in the art with reference to Examples, which will be described later.

The heterocyclic compound of Formula 1 may be used in an organic light-emitting diode.

According to another embodiment of the present invention, there is provided an organic light-emitting diode (OLED) including a first electrode, a second electrode facing the first electrode, and an organic layer interposed between the first electrode and the second electrode. The organic layer includes at least one layer and at least one of the heterocyclic compounds of Formula 1 described above.

The term "organic layer" used herein is interpreted to include an organic compound and at least one layer. For example, the organic layer may include at least one layer selected from the group consisting of a hole injection layer (HIL), a hole transport layer (HTL), a hole injection and transport layer having hole injection and transport abilities, an electron blocking layer (EBL), an emission layer (EML), a hole blocking layer (HBL), an electron injection layer (EIL), an electron transport layer (ETL), and an electron injection and transport layer having electron injecting and transporting abilities. The organic layer is not composed of only an organic compound, but may include an inorganic compound or an inorganic material. In one embodiment of the present invention, the organic layer may include both an organic compound and an inorganic compound or an inorganic material in one layer. For example, the organic layer may include both an organic compound and an organometallic complex in one layer. Alternatively, the organic layer may include a layer formed of an organic compound and another layer formed of only an inorganic compound or an inorganic material.

The organic layer may include at least one of the heterocyclic compounds in one layer or in different layers. For example, the organic layer may include an EML including one of the heterocyclic compounds listed above as a dopant and a HTL including another one of the heterocyclic compounds listed above as a hole transporting material. For example, the organic layer may include an EML including one of the heterocyclic compounds listed above as a dopant and another one of the heterocyclic compounds listed above as a host. For example, the organic layer may include an EML including one of the heterocyclic compounds listed above as a dopant and another one of the heterocyclic compounds listed above as a host and a HTL including another one of the heterocyclic compounds listed above as a hole transporting material. The organic layer may include at least one of an EML, a HIL, a HTL, and a hole injection and transport layer having hole injection and transport abilities. In this regard, at least one of the EML, the HIL, the HTL, and the hole injection and transport layer may include the heterocyclic compound listed above.

For example, the OLED may have a first electrode/HIL/HTL/EML/ETL/EIL/second electrode structure. In this regard, one of the EML, the HTL, and the HIL may include the heterocyclic compound listed above. In other embodiments of the present invention, at least two of the EML, the HTL, and the HIL may include the heterocyclic compound listed above. In these cases, the heterocyclic compounds listed above used in these layers may be different from each other. As described above, at least two of the heterocyclic compounds listed above may be used in a mixed form in each layer, and other compounds as well as at least one of the heterocyclic compounds listed above may also be used in a mixed form in each layer.

For example, the organic layer includes an EML including a host and a dopant. The heterocyclic compound may be used as a fluorescent host, a phosphorescent host, or a fluorescent dopant of the EML.

In some embodiments of the present invention, the organic layer may include an EML, the EML may further include an anthracene compound, an arylamine compound, or a styryl compound. In this regard, the EML may include or may not include the heterocyclic compound.

In addition, the organic layer may include an EML, and the EML may include a host and a dopant and further include a phosphorescent dopant. For example, the phosphorescent dopant may be, but is not limited to, an organometallic complex including at least one of iridium (Ir), platinum (Pt), osmium (Os), rhenium (Re), titanium (Ti), zirconium (Zr), hafnium (Hf), or a combination of at least two of these elements. In this regard, the EML may include or may not include the heterocyclic compound.

At least one of the En, the HTL, and the hole injection and transport layer may further include a charge-generating material. The charge-generating material may be a p-type dopant. In this regard, the HIL, the HTL, and the hole injection and transport layer may include or may not include the heterocyclic compound.

The organic layer may further include an ETL, and the ETL may include an electron transporting organic compound and a metal-containing material. The metal-containing material may include a Li-complex. In this regard, the ETL may include or may not include the heterocyclic compound.

At least one of the organic layers interposed between the first electrode and the second electrode may be formed by deposition or using a wet process.

The term "wet process" used herein refers to a process for applying a mixture obtained by mixing a certain material and a certain solvent on a certain substrate, drying and/or heat treating the substrate so as to remove part of the solvent, thereby forming a film including the material on the substrate.

For example, the organic layer may be formed using a general vacuum deposition method. Alternatively, a mixture of the heterocyclic compound and a solvent is provided to a region for forming an organic layer by spin coating, spraying, inkjet printing, dipping, casting, gravure coating, bar coating, roll coating, wirebar coating, screen coating, flexo coating, offset coating, or laser transferring, and the mixture provided to the region for forming an organic layer is then dried and/or heat treated so as to remove part of the solvent, thereby forming the organic layer.

Alternatively, an organic layer may be formed on a base film by vacuum deposition or a wet process as described above, and the organic layer may be transferred to a region (for example, on a HTL) for forming an organic layer by laser transferring.

Hereinafter, a structure and manufacturing method of an OLED will be described in more detail with reference to FIG. 1. FIG. 1 is a schematic diagram illustrating a structure of an organic light-emitting diode 10 according to an embodiment of the present invention.

Referring to FIG. 1, the OLED 10 includes a first electrode 13, an organic layer 15, and a second electrode 17 that are sequentially formed on the substrate 11 in this order.

The substrate 11 may be a substrate used in a general OLED, and may be a glass substrate or a transparent plastic substrate having excellent mechanical strength, thermal stability, transparency, surface smoothness, ease of handling, and waterproofness.

The first electrode 13 may be formed by applying a first electrode material on the substrate 11 by deposition or sputtering. When the first electrode 13 is an anode, the first electrode material may be selected from materials having a high work function so as to facilitate hole injection. The first electrode 13 may be a reflective electrode or a transparent electrode. Examples of the first electrode material may include indium-tin oxide (ITO), indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 13 may be formed as a reflective electrode.

The organic layer 15 is formed on the first electrode 13. The term "organic layer" used herein refers to all the layers interposed between the first electrode 13 and the second electrode 17. The organic layer 15 may not necessarily be formed of only an organic compound, and may also include a metal complex.

The organic layer 15 may include a HIL, a HTL, an EML, an ETL, and an EIL.

The HIL may be formed on the first electrode 13 by using various methods such as vacuum deposition, spin coating, casting, or LB deposition.

When the HIL is formed by vacuum deposition, the deposition conditions may vary according to a compound used as a material for forming the HIL, a structure of a desired HIL, and thermal characteristics. For example, the deposition conditions may be, but are not limited to, a deposition temperature of about 100° C. to about 500° C., a degree of vacuum of about $10^{-8}$ to about $10^{-3}$ torr, and a deposition speed of about 0.01 to about 100 Å/sec.

When the HIL is formed by spin coating as a wet process, the deposition conditions may vary according to a compound used as a material for forming the HIL, a structure of a desired HIL, and thermal characteristics. For example, the deposition conditions may be, but are not limited to, a coating speed of about 2000 rpm to about 5000 rpm and a heat treatment temperature for removing a solvent after coating of about 80° C. to about 200° C.

The material for forming the HIL may be the heterocyclic compound of Formula 1 or a known hole injection material. Examples of the known hole injection material include, but are limited to, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4'4"-tris(N,N-diphenylamino)triphenylamine (TDATA), 4,4',4"-tris{N,-(2-naphthyl)-N-phenylamino}-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline/poly(4-styrenesulfonate) (PANI/PSS).

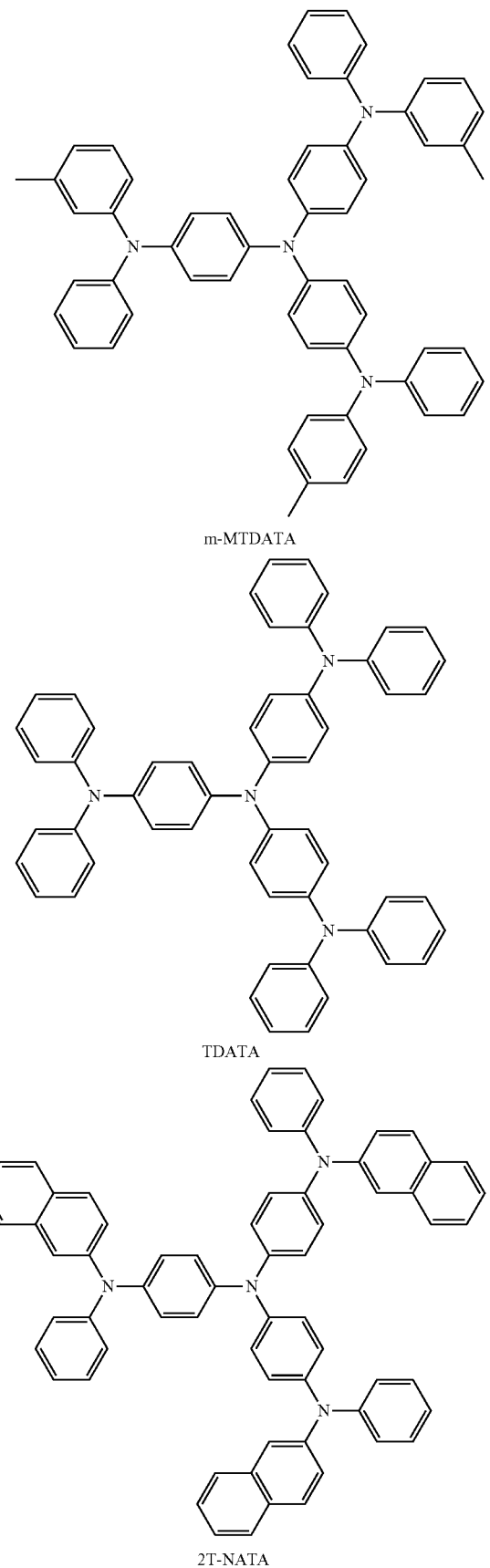

m-MTDATA

TDATA

2T-NATA

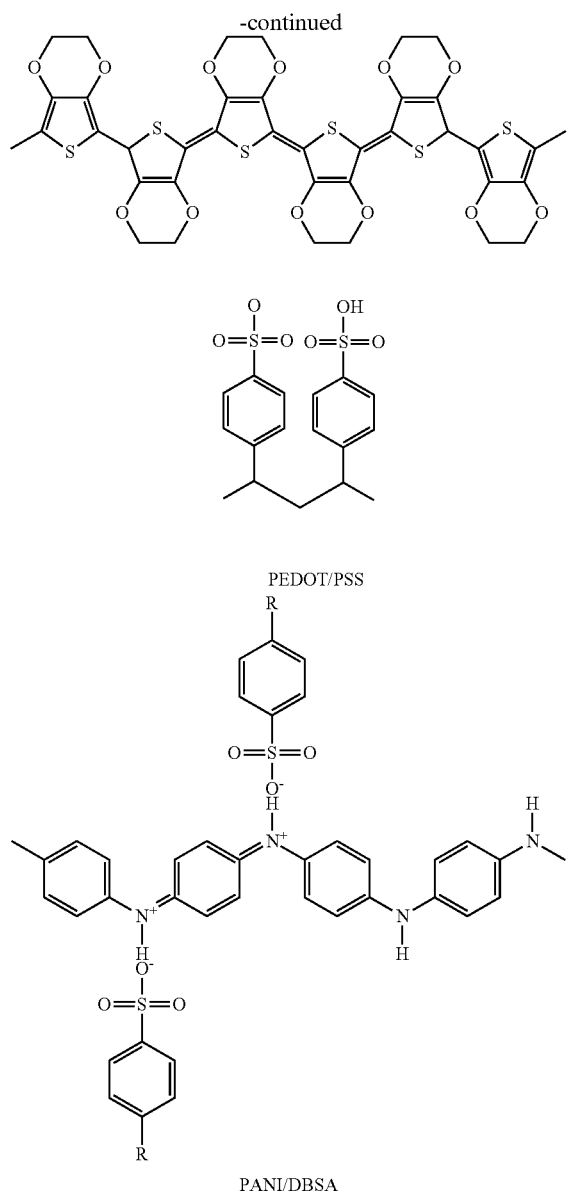

PEDOT/PSS

PANI/DBSA

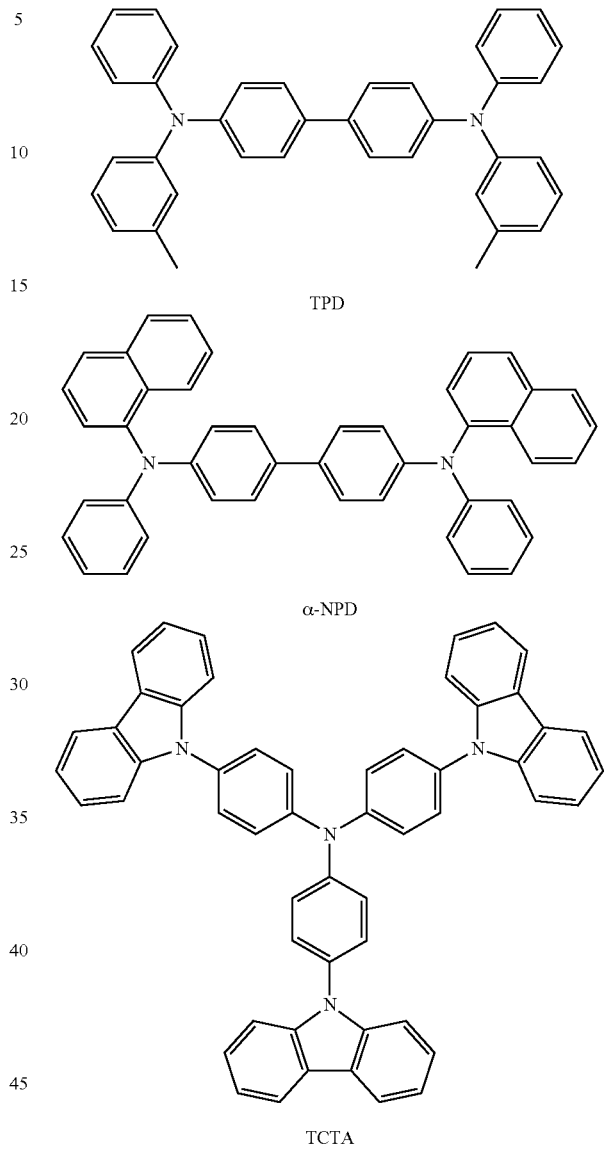

TPD

α-NPD

TCTA thyl)-N-phenylamino]biphenyl (α-NPD) and 4,4',4"-tris(N-carbazolyl)triphenylamine (TCTA), and the like.

The thickness of the HIL may be in the range of about 100 Å to about 10,000 Å, for example, in the range of about 100 Å to about 1,000 Å. When the thickness of the HIL is within this range, satisfactory hole injection properties may be obtained without a substantial increase in driving voltage.

Next, the HTL may be formed on the HIL by using various methods such as vacuum deposition, spin coating, casting, or LB deposition. When the HTL is formed by vacuum deposition or spin coating, the deposition and coating conditions vary according to a used compound. However, in general, the conditions may be almost the same as the conditions for forming the HIL.

A material for forming the HTL may be the heterocyclic compound of Formula 1 or a known hole transporting material. Examples of the known hole transporting material include carbazole derivatives such as N-phenylcarbazole; polyvinylcarbazole, and the like; triphenylamine-based materials such as N,N'-bis(3-methylphenyl)-N,N'-diphenyl-[1,1-biphenyl]-4,4'-diamine (TPD), and amine derivatives having aromatic condensed rings such as 4,4'-bis[N-(1-naph- The thickness of the HTL may be in the range of about 50 Å to about 1,000 Å, for example, in the range of about 100 Å to about 800 Å. When the thickness of the HTL is within this range, satisfactory hole transport properties may be obtained without a substantial increase in driving voltage.

In addition, the hole injection and transport layer having hole injection and transport abilities may be formed instead of the HIL and the HTL. A material for forming the hole injection and transport layer may be selected from the heterocyclic compound of Formula 1 and/or any known materials.

At least one of the HIL, the HTL, and the hole injection and transport layer may further include a charge-generating material so as to increase the conductivity of the layers, in addition to known hole injecting and hole transporting materials.

The charge-generating material may be, for example, a p-type dopant. Examples of the p-type dopant may include, but are not limited to, quinone derivatives such as tetra-cyanoquinodimethane (TCNQ) and 2,3,5,6-tetrafluoro-tetracyano-1,4-benzoquinodimethane (F4TCNQ), and the like; metal oxides such as an tungsten oxide and a molybdenum oxide, and the like; and cyano-containing compounds such as Compound 100 and the like.

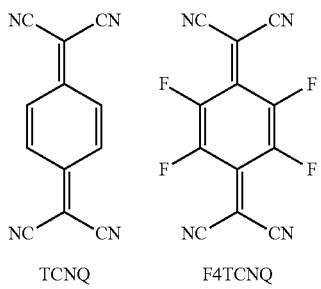

TCNQ       F4TCNQ

<Compound 100>

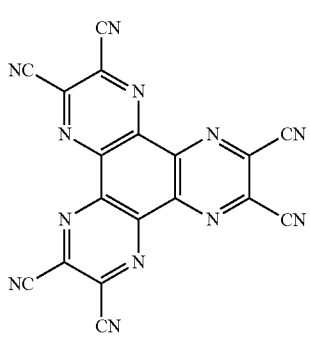

When the HIL, the HTL, or the hole injection and transport layer having hole injection and transport abilities further includes a charge-generating material, the charge-generating material may be homogeneously or inhomogeneously dispersed in these layers.

The EML may be formed on the HTL or the hole injection and transport layer having hole injection and hole transport abilities by vacuum deposition, spin coating, casting, or LB deposition. When the EML is formed by vacuum deposition or spin coating, the deposition and coating conditions vary according to a used compound. However, in general, the conditions may be almost the same as the conditions for forming the HIL.

A material thr forming the EML may be at least one of the heterocyclic compound of Formula 1 and a known luminescent material (including both a host and a dopant). When the EML includes the heterocyclic compound of Formula 1, the EML may further include a known phosphorescent host, a known fluorescent host, a known phosphorescent dopant, or a known fluorescent dopant. The heterocyclic compound of Formula 1 may act as a phosphorescent host; a fluorescent host, or a fluorescent dopant.

The heterocyclic compound of Formula 1 or a known host may be used as a host. Examples of the known host may include, but are not limited to, Tris(8-hydroxyquinolinato) aluminium (Alq$_3$), 4,4'-N,N'-dicabazole-biphenyl (CBP), poly(n-vinylcabazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), distyrylarylene (DSA), and E3.

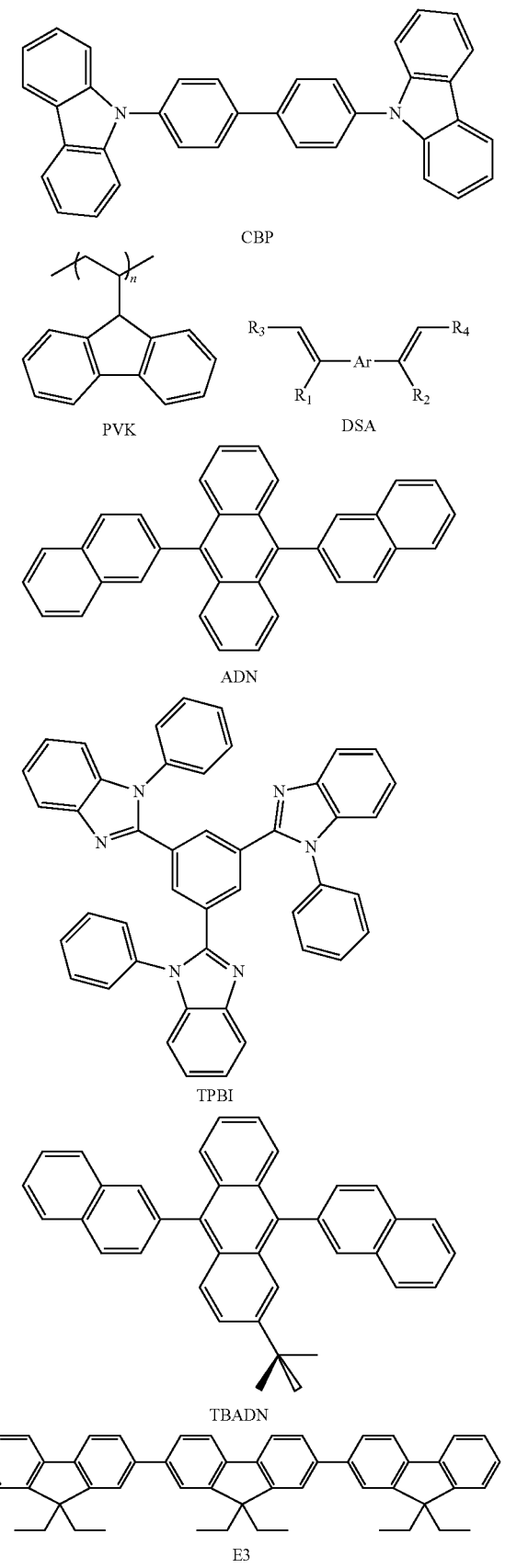

The heterocyclic compound of Formula 1 or a known dopant may be used as a dopant. The dopant may include at least one of a fluorescent dopant and a phosphorescent dopant. For example, the phosphorescent dopant may be, but is not limited to, an organometallic complex including at lease one selected from the group consisting of Ir, Pt, Os, Re, Ti, Zr, Hf, or a combination of at least two of these elements.

Examples of a known red dopants may include, are not limited to, Pt(II) Octaethylporphine (PtOEP), tris(2-phenyl-isoquinoline)iridium (Ir(piq)₃), and bis(2-(2'-benzothienyl)-pyridinato-N,C3')iridium(acetylacetonate) (Btp₂Ir(acac)).

and 10-(2-benzothiazolyl)-1,1,7,7-tetramethyl-2,3,6,7-tetrahydro-1H,5H,11H-[1]benzopyrano[6,7,8-ij]-quinolizin-11-one (C545T).

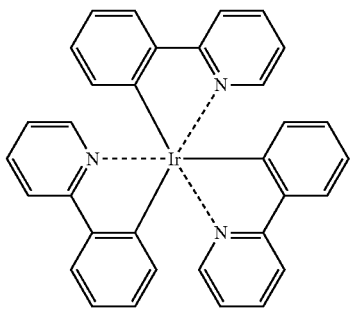

Ir(ppy)₃

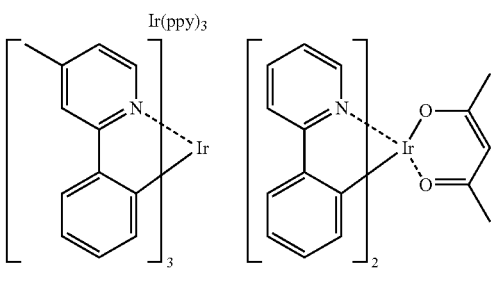

Ir(mppy)₃    Ir(ppy)₂(acac)

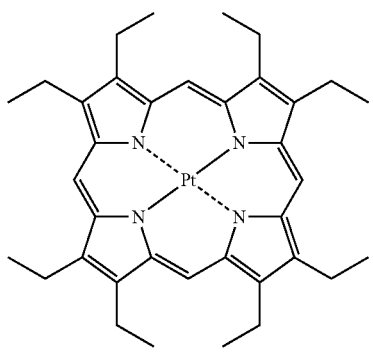

PtOEP

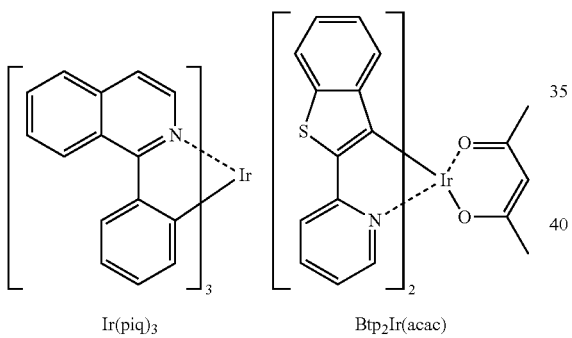

Ir(piq)₃    Btp₂Ir(acac)

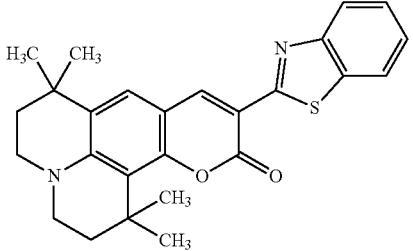

C545T

Examples of a known green dopants may include, are not limited to, tris(2-phenylpyridine) iridium (Ir(ppy)₃), bis(2-phenylpyridine)(acetylacetonato)iridium(III) (Ir(ppy)₂(acac)), tris(2-(4-tolyl)phenylpiridine)iridium (Ir(mppy)₃), Examples of a blue dopants may include, are not limited to, Bis[3,5-difluoro-2-(2-pyridyl)phenyl](picolinato)iridium (III) (F₂Irpic), (F₂ppy)₂Ir(tmd), Ir(dfppz)₃, 4,4'-bis(2,2'-diphenylethen-1-yl)biphenyl (DPVBi), 4,4'-bis(4-diphenylaminosteril)biphenyl (DPAVBi), and 2,5,8,11-tetra-tert-butylpherylene (TBPe).

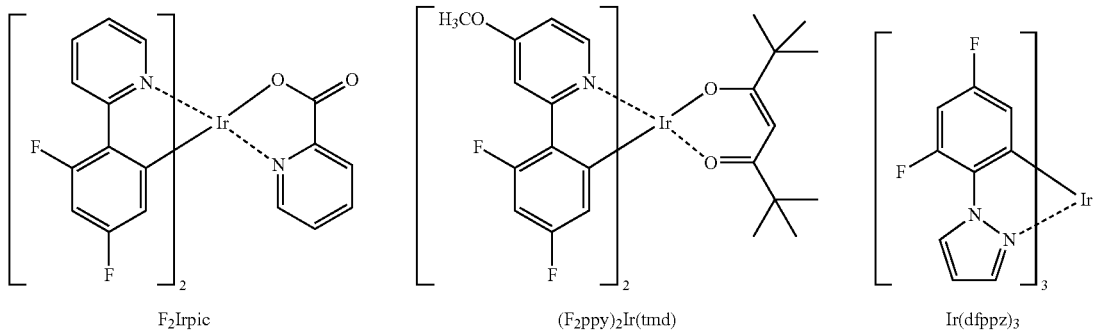

F₂Irpic    (F₂ppy)₂Ir(tmd)    Ir(dfppz)₃

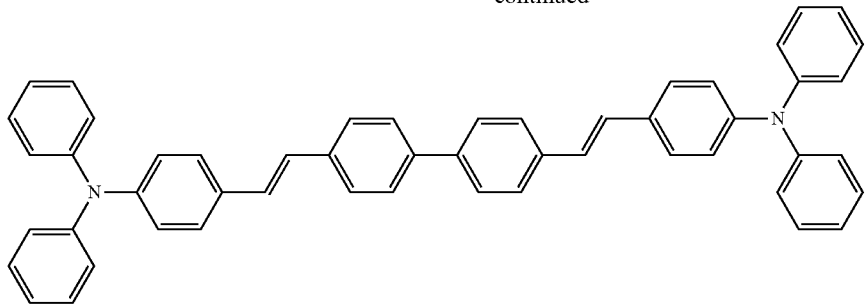

DPAVBi

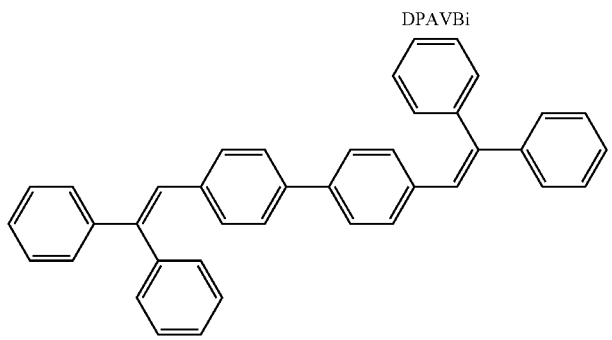

DPVBi

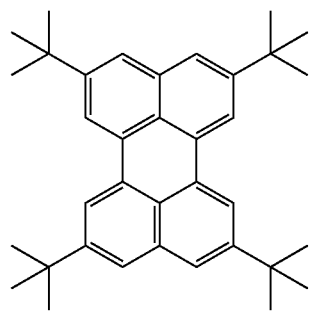

TBPe

When the EML includes a host and a dopant, the amount of the dopant may be generally in the range of about 0.01 to about 15 parts by weight based on 100 parts by weight of the host; however, it is not limited thereto.

The thickness of the EML may be in the range of about 100 Å to about 1,000 Å, for example, in the range of about 200 Å to about 600 Å. When the thickness of the EML is within this range, excellent luminescent properties may be obtained without a substantial increase in driving voltage.

When the phosphorescent dopant is included in the EML, a HBL may be formed between the ETL and the EML by vacuum deposition, spin coating, casting or LB deposition so as to prevent triplet excitons or holes from being diffused to the ETL. When the HBL is formed by vacuum deposition or spin coating, the conditions thereof may vary according to a used compound. However, in general, the conditions may be almost the same as the conditions for forming the HIL. The HBL may include a well-known hole blocking material. Examples of the well-known hole blocking materials may include an oxadiazole deriative, a triazole derivative, and a phenanthroline derivative. For example, 2,9-dimethyl-4,7-diphenyl-1,10-phenanthroline (BCP) may be used as a hole blocking material.

The thickness of the HBL may be in the range of about 50 Å to about 1,000 Å, for example, in the range of about 100 Å to about 300 Å. When the thickness of the HBL is within this range, excellent hole blocking properties may be obtained without a substantial increase in driving voltage.

Next, the ETL may be formed on the HBL or EML using various methods such as vacuum deposition, spin coating, or casting. When the ETL is formed by vacuum deposition or spin coating, the deposition and coating conditions vary according to a used compound. However, in general, the conditions may be almost the same as the conditions for forming the HIL.

A material for forming the ETL may be a known electron transporting material. Examples of the known electron transporting materials may include, but are not limited to, a quinoline derivative such as tris(8-quinolinolate)aluminum ($Alq_3$), 2,9-dimethyl-4,7-diphenyl-1,10-phenanthroline (BCP), 4,7-diphenyl-1,10-phenanthroline (Bphen), 3-(4-Biphenylyl)-4-phenyl-5-tert-butylphenyl-1,2,4-triazole (TAZ),4-(naphtha-len-1-yl)-3,5-diphenyl-4H-1,2,4-triazole (NTAZ), 2-(4-biphenylyl)-5-(4-tert-butylphenyl)-1,3,4-oxadiazole (tBu-PBD), BAlq (refer to Formula below), beryllium bis (benzoquinolin-10-olate) ($Bebq_2$), 9,10-di(naphthalene-2-yl) anthrascene (ADN), and known materials such as Compound 101 and Compound 102 below.

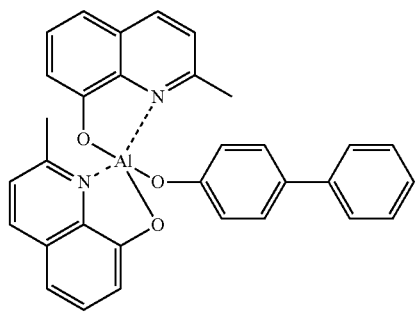

BAlq

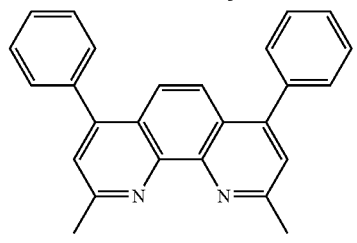

BCP

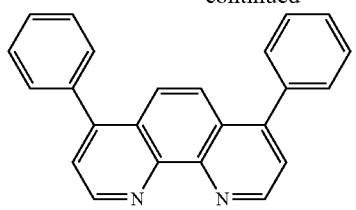

Bphen

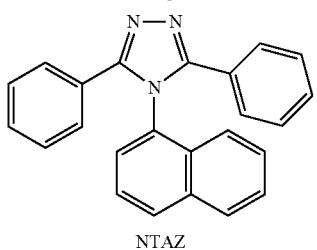

NTAZ

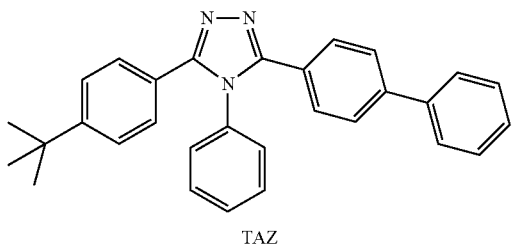

TAZ

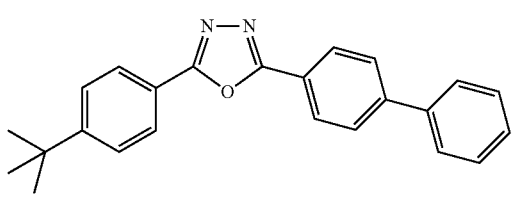

tBu-PBD

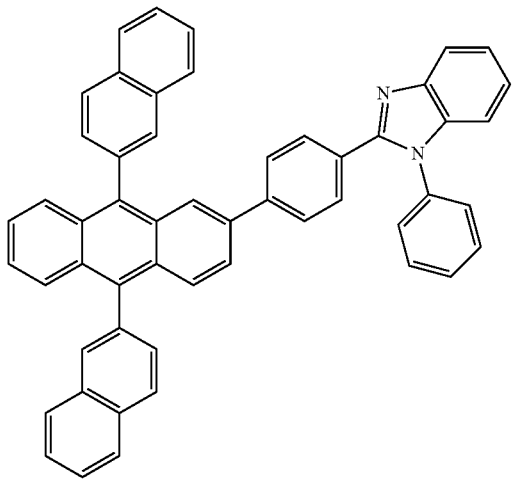

<Compound 101>

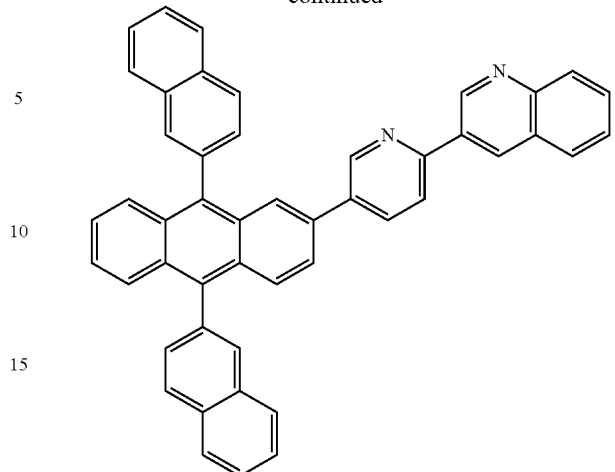

<Compound 102>

The thickness of the ETL may be in the range of about 100 Å to about 1,000 Å, for example, in the range of about 150 Å to about 500 Å. When the thickness of the ETL is within this range, satisfactory electron transport properties may be obtained without a substantial increase in driving voltage.

In addition, the ETL may include an electron-transporting organic compound and a metal-containing material. The metal-containing material may include a Li-complex. Examples of the Li-complex may include lithium quinolate (LiQ) and Compound 103 below:

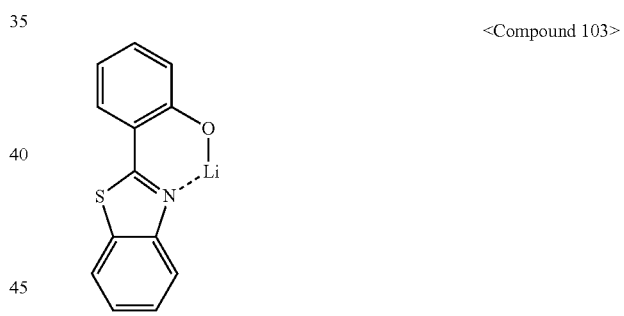

<Compound 103>

Also, the EIL, which facilitates electron injection from a cathode, may be formed on the ETL, and a material for forming the EIL is not particularly limited.

The material for forming the EIL may include a well-known material for forming an EIL, such as LiF, NaCl, CsF, $Li_2O$, or BaO. The deposition conditions of the EIL may vary according a used compound. However, in general, the conditions may be almost the same as the conditions for forming the HIL.

The thickness of the EIL may be in the range of about 1 Å to about 100 Å, for example, in the range of about 3 Å to about 90 Å. When the thickness of the EIL is within this range, satisfactory electron injection properties may be obtained without a substantial increase in driving voltage.

The second electrode 17 is formed on the organic layer 15. The second electrode 17 may be a cathode, which is an electron injection electrode. Here, a material for forming the second electrode 17 may include a material having a low work function, such as metal, an alloy, an electric conducting compound, or a mixture thereof. In particular, the second electrode 17 may be formed as a thin film by using lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type organic light-emitting diode, the second electrode 17 may be formed as a transparent electrode by using ITO or IZO.

An OLED according to an embodiment of the present invention will now be described in more detail with reference to the following Examples. These Examples are for illustrative purposes only and are not intended to limit the scope of the present invention.

EXAMPLES

Synthesis Example 1

Synthesis of Intermediate I-4 (Synthesis Scheme 1)

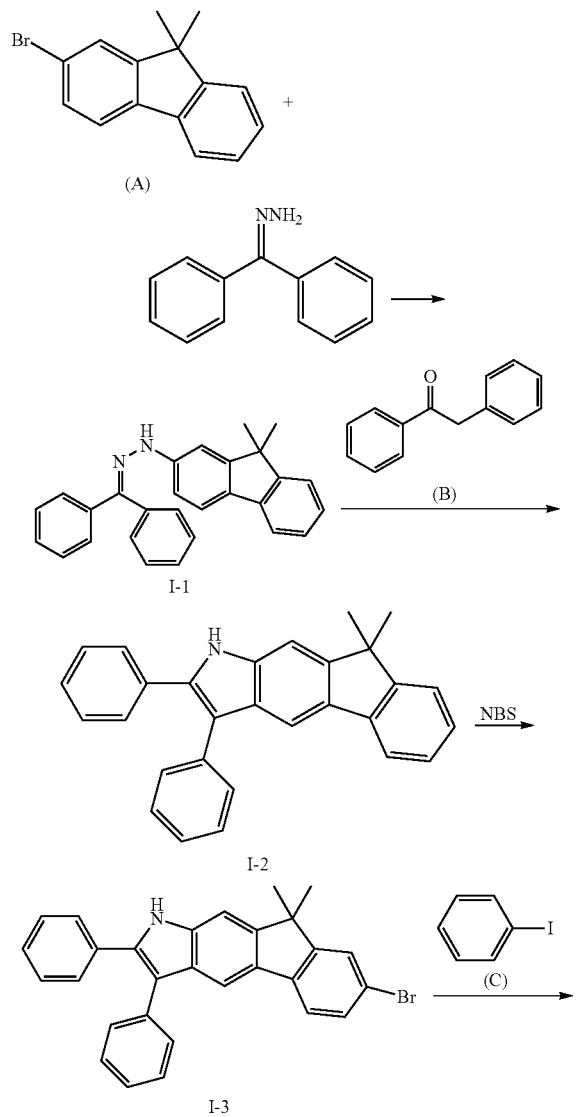

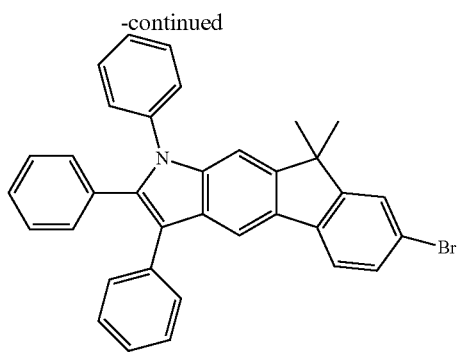

I-4

Synthesis of Intermediate I-1

10.926 g (40 mmol) of 2-bromo-9,9-dimethylfluorene (A), 8.635 g (44 mmol) of benzophenonehydrazone, 0.328 g (0.8 mmol) of 2-dicyclohexylphosphino-T,6'-dimethoxybiphenyl, 0.179 g (0.8 mmol) of Pd(OAc)$_2$, and 5.767 g (60 mmol) of NaOtBu were dissolved in 300 ml of toluene, and the mixture was stirred at 100° C. for 24 hours. The reaction solution was cooled down to room temperature and then extracted three times with 200 ml of water and 200 ml of diethylether. The obtained organic layer was dried with magnesium sulfate, and a solvent was evaporated therefrom to obtain a crude product. The crude product was purified with silicagel column chromatography to obtain 11.75 g (30.4 mmol) of intermediate I-1 (yield 75.6%). The obtained compound was confirmed by MS/FAB (calculated value: 388.50, measured value: 388.19).

Synthesis of Intermediate I-2

11.75 g (30.4 mmol) of Intermediate I-1, 11.77 g (60 mmol) of benzylphenylketone (B), and 11.41 g (60 mmol) of p-toluenesulfonic acid (p-TsOH) were dissolved in 200 ml of a toluene/ethanol solvent mixture (at a volume ratio of 4:1), and the resultant mixture was stirred at 100° C. for 24 hours. The reaction solution was cooled down to room temperature, a solvent was removed therefrom, and the resultant product was extracted three times with 100 ml of water and 100 ml of diethylether. The obtained organic layer was dried with magnesium sulfate, and a solvent was evaporated therefrom to obtain a crude product. The crude product was purified with silicagel column chromatography to obtain 8.59 g (22.2 mmol) of Intermediate I-2 (yield is 74.2%). The obtained compound was confirmed by MS/FAB (calculated value: 385.50, measured value: 386.18).

Synthesis of Intermediate I-3

To a solution obtained by dissolving 8.59 g (22.2 mmol) of Intermediate I-2 in 100 ml of methylenechloride was added a solution obtained by dissolving 3.933 g (22.2 mmol) of N-bromosuccinimide (NBS) in 100 ml of methylenechloride, and the mixed solution was stirred at room temperature for 2 hours. The solvent was removed therefrom and the resultant mixture was purified with column chromatography to obtain 9.75 g (21 mmol) of Intermediate I-3 (yield 94.5%). The obtained compound was confirmed by MS/FAB (calculated value: 464.40, measured value: 465.80).

Synthesis of Intermediate I-4

9.75 g (21 mmol) of Intermediate I-3, 6.42 g (31.5 mmol) of iodobenzene (C), 0.385 g (0.42 mmol) of tris(dibenzylideneacetone)dipalladium (Pd$_2$(dba)$_3$), 0.084 g (0.42 mmol) of PtBu$_3$, and 3.027 g (31.5 mmol) of KOtBu were dissolved in 200 ml of toluene, and the mixture was stirred at 85° C. for 4 hours. The reaction solution was cooled down to room temperature and the resultant product was extracted three times with 100 ml of water and 100 ml of diethylether. The obtained organic layer was dried with magnesium sulfate, and the solvent was evaporated therefrom to obtain a crude product. The crude product was purified with silicagel column chromatography to obtain 9.188 g (17 mmol) of intermediate I-4 (yield 79%). The obtained compound was confirmed by MS/FAB (calculated value: 540.49, measured value: 541.80).

Synthesis Example 2

Synthesis of Intermediate I-5 (Synthesis Scheme 2)

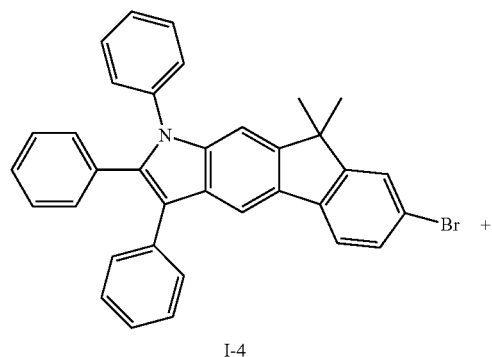

I-4

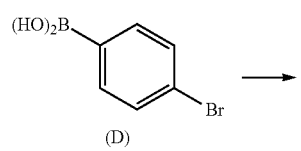

(D)

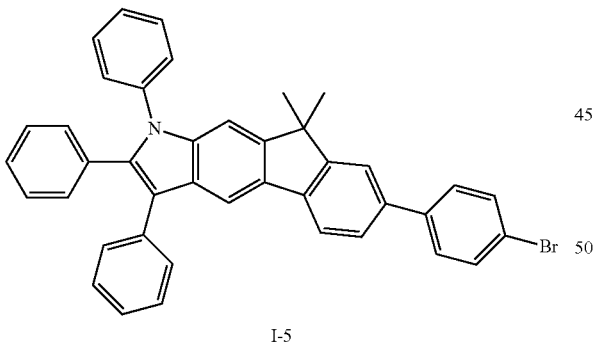

I-5

3.242 g (66 mmol) of Intermediate I-4, 1.204 g (6 mmol) of 4-bromophenylboronic acid (D), 0.346 g (0.3 mmol) of Pd(PPh$_3$)$_4$, and 1.658 g (12 mmol) of K$_2$CO$_3$ were dissolved in 40 ml of a mixed solution of THF/H$_2$O (at a volume ratio of 2:1), and the mixture was stirred at 80° C. for 5 hours. The reaction solution was cooled down to room temperature, 40 ml of water was added thereto, and the resultant solution was extracted three times with 50 ml of ethylether. The obtained organic layer was dried with magnesium sulfate, and the solvent was evaporated therefrom to obtain a crude product. The crude product was purified with silicagel column chromatography to obtain 2.086 g (3.38 mmol) of Intermediate I-5 (yield 56.3° A). The obtained compound was confirmed by MS/FAB (calculated value: 616.59, measured value: 617.40).

Synthesis Example 3

Synthesis of Intermediate I-6 (Synthesis Scheme 3)

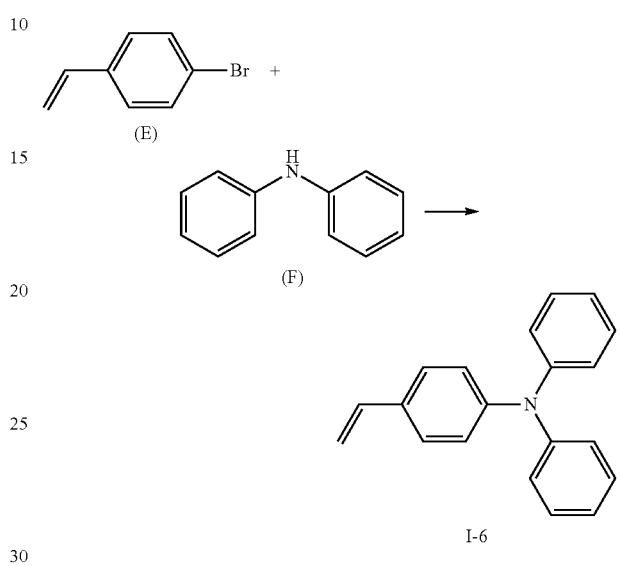

10.983 g (60 mmol) of 4-bromostyrene (E), 8.461 g (50 mmol) of diphenylamine (F), 0.915 g (1 mmol) of Pd$_2$(dba)$_3$, 0.202 g (1 mmol) of PtBu$_3$, and 69.611 g (100 mmol) of KOtBu were dissolved in 150 ml of toluene, and the mixture was stirred at 85° C. for 4 hours. The reaction solution was cooled down to room temperature and the resultant solution was extracted three times with 100 ml of water and 100 ml of diethylether. The obtained organic layer was dried with magnesium sulfate, and the solvent was evaporated therefrom to obtain a crude product. The crude product was purified with silicagel column chromatography to obtain 7.326 g (27 mmol) of Intermediate I-6 (yield 54%). The obtained compound was confirmed by MS/FAB (calculated value: 271.36, measured value: 271.36).

Synthesis Example 4

Synthesis of Intermediate I-7 (Synthesis Scheme 4)

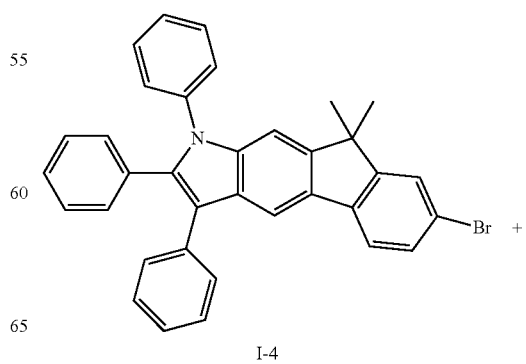

I-4

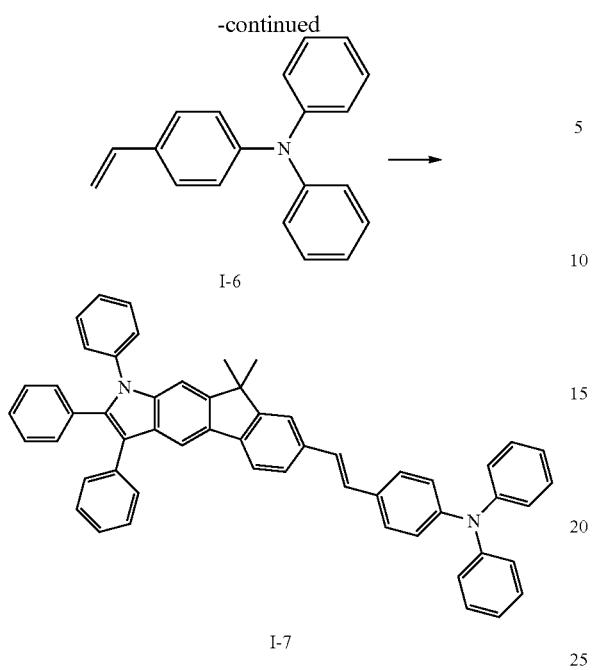

2.702 g (5 mmol) of Intermediate I-4, 1.356 g (5 mmol) of Intermediate I-6, 0.056 g (0.25 mmol) of Pd(OAc)$_2$, 0.76 g (0.25 mmol) of (p-toly)$_3$P, and 1.019 (10 mmol) of Et$_3$N were dissolved in 30 ml of dimethylacetamide (DMAc), and the mixture was stirred at 85° C. for 4 hours. The reaction solution was cooled down to room temperature and the resultant solution was extracted three times with 30 ml of water and 30 ml of diethylether. The obtained organic layer was dried with magnesium sulfate, and the solvent was evaporated therefrom to obtain a crude product. The crude product was purified with silicagel column chromatography to obtain 2.046 g (2.8 mmol) of Intermediate I-7 (yield 56%). The obtained compound was confirmed by It MS/FAB (calculated value: 730.94, measured value: 732.05).

Synthesis Example 5

Synthesis of Compound 37 (Synthesis Scheme 5)

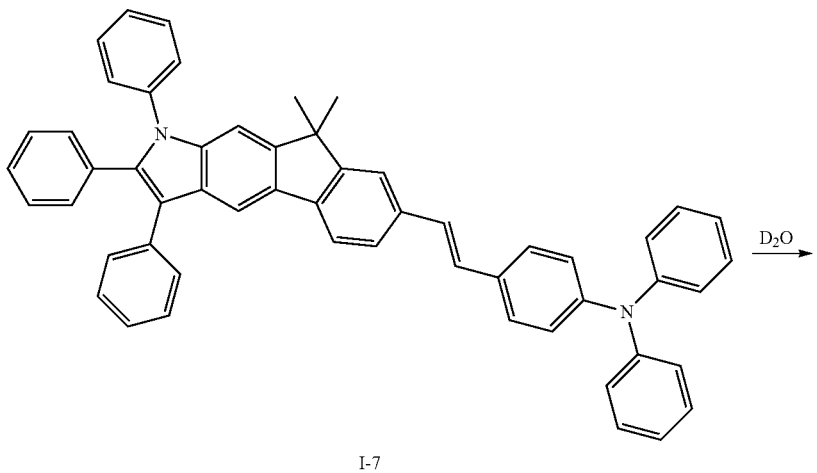

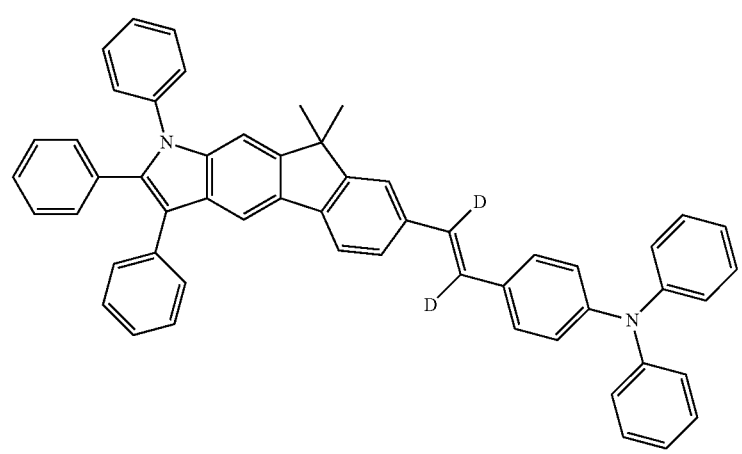

37

2.046 g (2.8 mmol) of Intermediate I-7, 0.081 g (0.08 mmol) of carbonylchlorohydridotris(triphenylphosphin)ruthenium (II) ((Ph$_3$)PbRu(CO)(Cl)H), and 0.56 g (28.0 mmol) of D$_2$O were dissolved in 30 ml of 1,4-dioxane, and the mixture was stirred at 80° C. for 12 hours. The reaction Solution was cooled down to room temperature, the solvent was removed therefrom, and the resultant solution was extracted three times with 50 ml of water and 50 ml of dichloromethane. The obtained organic layer was dried with magnesium sulfate, and the solvent was evaporated therefrom to obtain a crude product. The crude product was purified with silicagel column chromatography to obtain 1.557 g (2.12 mmol) of Compound 37 (yield 76%). The obtained compound was confirmed by MS/FAB.

Synthesis Example 6

Synthesis of Compound 63 (Synthesis Scheme 4)

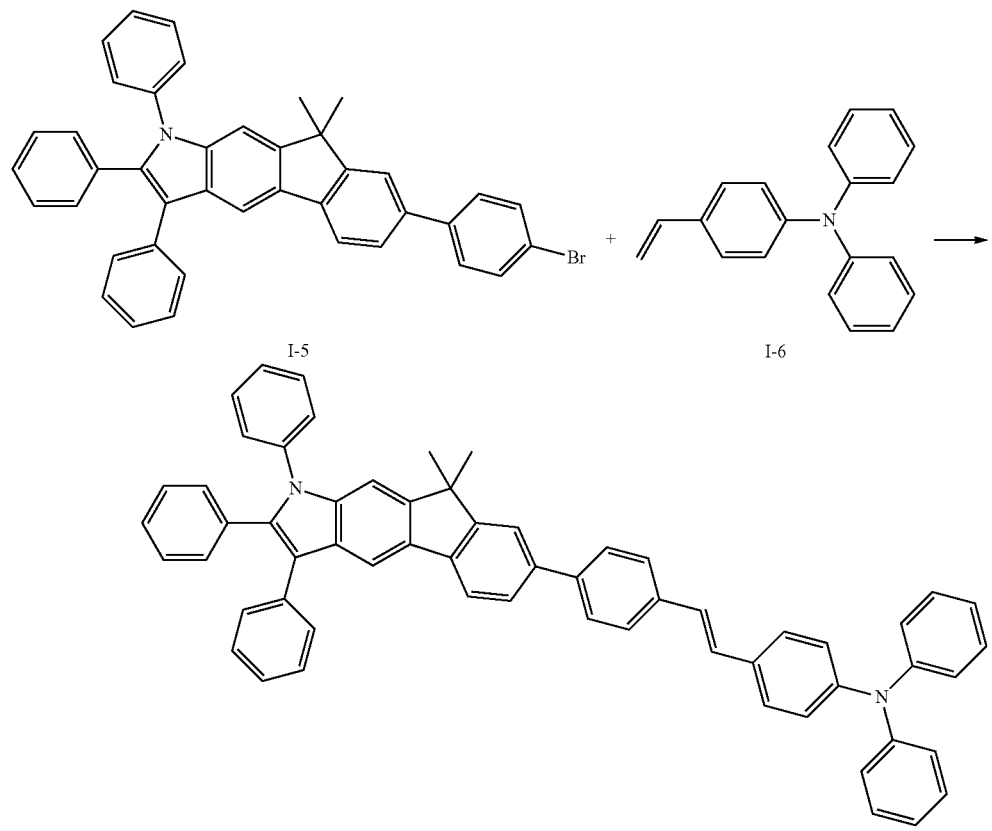

1.694 g (2.8 mmol) of Compound 63 (42%) was obtained in the same manner as in the synthesis of Intermediate I-7 (Synthesis Scheme 4), except that Intermediate I-5 was used instead of Intermediate I-4. The obtained compound was confirmed by MS/FAB.

Compounds 1, 2, 4-6, 8, 10, 14, 16, 18, 21, 22, 24, 25, 27, 32-34, 36-38, 41, 43-46, 51-53, 57, 59-61, 63, 64, 67-69, 74-79 were synthesized according to Synthesis Scheme 4 or 5 and using appropriate raw materials, and 1H NMR and MS/FAB of the synthesized compounds are shown in Table 1 below. In addition, the Synthesis Scheme used in preparation of each compound and raw materials other than the materials used in the Synthesis Scheme are shown in Table 1 below.

For example, Compound 1 was synthesized in the same manner as in Synthesis Scheme 4, except that a material synthesized according to Synthesis Scheme 1 by using methylethylketone as a (B) material instead of benzylphenylketone and ethyl iodide as a (C) material instead of iodobenzene was used as Intermediate I-4 of Synthesis Scheme 4.

For example, Compound 2 was synthesized in the same manner as in Synthesis Scheme 4, except that a material synthesized according to Synthesis Scheme 1 by using methylethylketone as a (B) material instead of benzylphenylketone was used as Intermediate I-4 of Synthesis Scheme 4, and a material synthesized according to Synthesis Scheme 3 by using di-o-tolylamine as a (F) material instead of diphenylamine was used as Intermediate I-6 of Synthesis Scheme 4.

For example, Compound 5 was synthesized in the same manner as in Synthesis Scheme 5, except that a material synthesized by using as Intermediate I-4 of Synthesis Scheme 4 a material synthesized according to Synthesis Scheme 1 by using methylethylketone as a (B) material instead of benzylphenylketone was used as Intermediate I-7 of Synthesis Scheme 5.

For example, Compound 64 was synthesized in the same manner as in Synthesis Scheme 4, except that a material synthesized according to Synthesis Scheme 2 by using 6-bromo-2-naphthylboronic acid as a (D) material instead of 4-bromophenylboronic acid was used as Intermediate I-4 of Synthesis Scheme 4.

Synthesis methods of the other compounds shown in Table 2 may also be well understood by one of ordinary skill in the art with reference to the synthesis schemes and raw materials shown in Table 1 below:

TABLE 1

| Compound | Synthesis Scheme | Raw material used instead of original raw material used in Synthesis Scheme | $^1$H NMR (CDCl$_3$, 400 MHz) | MS/FAB found | calc. |
|---|---|---|---|---|---|
| 1 | 4 | (B), (C) | 7.99 (s, 1H), 7.90-7.82 (m, 2H), 7.70-7.60 (m, 5H), 7.45 (s, 1H), 7.42-7.36 (m, 5H), 7.20-7.05 (m, 4H), 6.60-6.54 (m, 3H), 4.01-3.97 (m, 2H), 2.17 (m, 3H), 2.11 (s, 3H), 1.63 (s, 6H), 1.36 (t, 3H) | 559.86 | 558.75 |
| 2 | 4 | (B), (F) | 7.98 (s, 1H), 7.89-7.82 (m, 2H), 7.70-7.58 (m, 10H), 7.30-7.22 (m, 5H), 7.16-7.12 (m, 2H), 6.98-6.88 (m, 4H), 2.26 (m, 3H), 2.19 (m, 3H), 1.87 (s, 6H), 1.62 (s, 6H) | 636.10 | 634.85 |
| 4 | 4 | (B) | 7.99 (s, 1H), 7.90-7.82 (m, 2H), 7.70-7.54 (m, 10H), 7.31-7.26 (m, 5H), 7.18-7.11 (m, 4H), 6.88-6.83 (m, 4H), 2.27 (m, 3H), 2.20 (m, 3H), 1.62 (m, 6H) | 308.01 | 306.81 |
| 5 | 5 | (B) | 7.99 (s, 1H), 7.90-7.83 (m, 2H), 7.69-7.56 (m, 9 H), 7.32-7.28 (m, 4H), 7.20-7.14 (m, 4H), 6.89-6.83 (m, 4H), 2.27 (m, 3H), 2.20 (m, 3H), 1.63(s, 6H) | 609.84 | 608.81 |
| 6 | 4 | (B), (F) | 7.98 (s, 1H), 7.91-7.78 (m, 3H), 7.72-7.66 (m, 10H), 7.41-7.37 (m, 2H), 7.08-7.00 (m, 1H), 6.96-6.92 (m, 2H), 6.68-6.64 (m, 2H), 6.58-6.56 (m, 2H), 2.26 (m, 3H), 2.19 (m, 3H), 2.09 (m, 3H), 2.00 (m, 3H), 1.63 (m, 6H) | 660.84 | 659.86 |

TABLE 1-continued
| Compound | Synthesis Scheme | Raw material used instead of original raw material used in Synthesis Scheme | $^1$H NMR (CDCl$_3$, 400 MHz) | MS/FAB found | MS/FAB calc. |
|---|---|---|---|---|---|
| 8 | 5 | 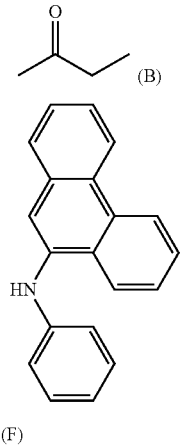 (B) 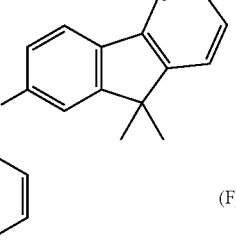 (F) | 8.33 (d, 1H), 8.09 (m, 1H), 7.99 (s, 1H), 7.94-7.90 (m, 2H), 7.84-7.76 (m, 5H), 7.70-7.58 (m, 10H), 7.28-7.24 (m, 3H), 7.00-6.96 (m, 3H), 6.52-6.49 (m, 2H), 2.26 (m, 3H), 2.19 (m, 3H), 1.62 (s, 6H) | 710.01 | 708.93 |
| 10 | 5 | 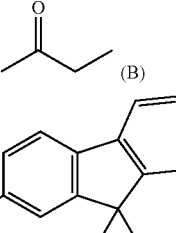 (B) 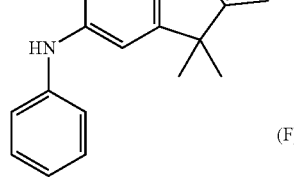 (F) | 7.99 (s, 1H), 7.90-7.84 (m, 2H), 7.80-7.76 (m, 2H), 7.72-7.50 (m, 10H), 7.34-7.24 (m, 4H), 6.98-6.88 (m, 4H), 6.69 (d, 1H), 6.60-6.56 (m, 2H), 2.27 (m, 3H), 2.20 (m, 3H), 1.62 (d, 12H). | 725.99 | 724.97 |
| 14 | 4 | 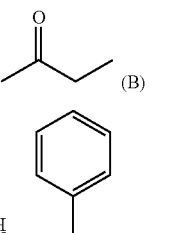 (B) 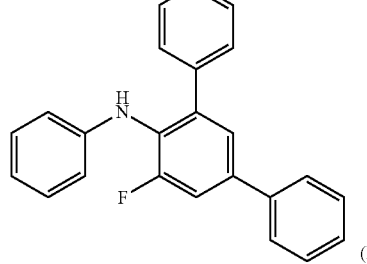 (F) | 7.99 (s, 1H), 7.90 (d, 1H), 7.84-7.78 (m, 6H), 7.74-7.71 (m, 5H), 7.65-7.48 (m, 11H), 7.33-7.23 (m, 4H), 6.98-6.90 (m, 3H), 6.54-6.52 (m, 2H), 2.26 (m, 3H), 2.20 (m, 3H), 1.63 (s, 6H) | 777.48 | 776.36 |
| 16 | 4 | 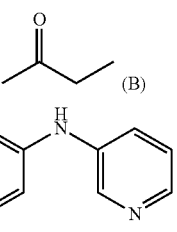 (B) 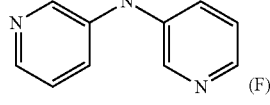 (F) | 8.33-8.30 (m, 2H), 8.12-8.10 (m, 3H), 8.02 (d, 1H), 7.72 (d, 1H), 7.65-7.48 (m, 12H), 7.38-7.30 (m, 2H), 7.16 (d, 1H), 7.08-7.02 (m, 2H), 2.28 (m, 3H), 2.21 (m, 3H), 1.63 (s, 6H) | 609.94 | 608.77 |

TABLE 1-continued

| Compound | Synthesis Scheme | Raw material used instead of original raw material used in Synthesis Scheme | $^1$H NMR (CDCl$_3$, 400 MHz) | MS/FAB found | MS/FAB calc. |
|---|---|---|---|---|---|
| 18 | 4 | (B) methyl ethyl ketone; (F) N-phenyl-3-(pyridin-3-yl)aniline | 8.43 (d, 1H), 8.27 (m, 1H), 8.00 (s, 1H), 7.94-7.90 (m, 2H), 7.84 (d, 1H), 7.78-7.68 (m, 11H), 7.60-7.54 (m, 2H), 7.48-7.40 (m, 4H), 7.20-7.16 (m, 2H), 7.08-7.00 (m, 1H), 6.64-6.60 (m, 2H), 6.56-6.52 (m, 1H), 2.28 (m, 3H), 2.20 (m, 3H), 1.63 (s, 6H) | 685.05 | 683.88 |
| 21 | 4 | (B) methyl ethyl ketone; (F) N-phenyldibenzofuran-2-amine | 7.98 (s, 1H), 7.90-7.82 (m, 3H), 7.76-7.48 (m, 15H), 7.18-7.12 (m, 3H), 7.00-6.94 (m, 3H), 6.72-6.70 (m, 1H), 6.56-6.54 (m, 2H), 2.27 (m, 3H), 2.20 (m, 3H), 1.63 (s, 6H) | 698.06 | 696.88 |
| 22 | 4 | (B) methyl ethyl ketone; (E) 1-vinylnaphthalene (Ha$_1$) | 7.98 (s, 1H), 7.92-7.88 (m, 2H), 7.80-7.70 (m, 3H), 7.64-7.58 (m, 7H), 7.33-7.26 (m, 4H), 7.20-7.12 (m, 4H), 7.08-7.04 (m, 1H), 6.82-6.78 (m, 1H), 6.70-6.64 (m, 2H), 6.34-6.30 (m, 3H), 2.27 (m, 3H), 2.20 (m, 3H), 1.63 (s, 6H) | 657.84 | 656.86 |
| 24 | 4 | (B) methyl ethyl ketone; (E) 2,6-divinylnaphthalene (Ha$_1$) | 7.99 (s, 1H), 7.96-7.90 (m, 3H), 7.84-7.80 (m, 4H), 7.68-7.56 (m, 7H), 7.38-7.28 (m, 6H), 7.24 (dd, 1H), 7.02-6.98 (m, 2H), 6.38-6.36 (m, 4H), 2.27 (m, 3H), 2.20 (m, 3H), 1.64 (s, 6H) | 660.89 | 659.86 |
| 25 | 4 | (B) methyl ethyl ketone; (E) 1,5-divinylnaphthalene (Ha$_1$) | 7.98 (s, 1H), 7.96-7.91 (m, 2H), 7.84-7.80 (m, 2H), 7.68-7.48 (m, 8H), 7.44-7.40 (m, 2H), 7.36-7.28 (m, 6H), 7.02-6.98 (m, 2H), 6.88-6.84 (m, 2H), 6.34-6.30 (m, 3H), 2.27 (m, 3H), 2.20 (m, 3H), 1.64 (s, 6H)/40 | 660.84 | 659.86 |

TABLE 1-continued

| Compound | Synthesis Scheme | Raw material used instead of original raw material used in Synthesis Scheme | ¹H NMR (CDCl₃, 400 MHz) | MS/FAB found | MS/FAB calc. |
|---|---|---|---|---|---|
| 27 | 4 | (structure: methyl ethyl ketone (B); 4'-vinyl-4-halo-biphenyl with Ha₁ (E)) | 7.99 (s, 1H), 7.90-7.82 (m, 2H), 7.68-7.50 (m, 13H), 7.28-7.22 (m, 6H), 7.05-7.01 (m, 4H), 6.56-6.53 (m, 4H), 2.27 (m, 3H), 2.19 (m, 3H), 1.83 (s, 6H) | 683.45 | 682.39 |
| 32 | 5 | (structure: 2-bromo-9,9-diphenylfluorene (A); methyl ethyl ketone (B)) | 7.95 (s, 1H), 7.73-7.71 (m, 1H), 7.68-7.55 (m, 12H), 7.36-7.21 (m, 10H), 7.11 (d, 1H), 6.95-6.90 (m, 1H), 6.78-6.70 (m, 4H), 6.50-6.47 (m, 4H), 2.26 (s, 3H), 2.22 (s, 3H) | 733.99 | 732.95 |
| 33 | 5 | (structure: 2-bromo-9,9'-spirobifluorene (A); methyl ethyl ketone (B)) | 7.96 (d, 2H), 7.88 (d, 2H), 7.78 (d, 1H), 7.60-7.45 (m, 10H), 7.40 (t, 2H), 7.35-7.28 (m, 4H), 7.20 (s, 1H), 7.08 (d, 2H), 7.00-6.94 (m, 4H), 6.58-6.50 (m, 4H), 2.27 (s, 3H), 2.22 (s, 3H) | 731.94 | 730.93 |
| 34 | 4 | (structure: tert-butyl halide with Ha₁ (C)) | 8.05 (s, 1H), 7.80-7.76 (m, 2H), 7.70-7.42 (m, 12H), 7.32 (s, 1H), 7.15-7.08 (m, 7H), 6.89-6.83 (m, 4H), 6.35-6.33 (m, 4H), 1.77 (s, 9H), 1.63 (s, 6H) | 712.05 | 710.95 |
| 36 | 4 | (structure: 1-halonaphthalene with Ha₁ (C)) | 8.05 (s, 1H), 7.90-7.85 (m, 2H), 7.78-7.38 (m, 20H), 7.18-7.14 (m, 7H), 6.89-6.83 (m, 4H), 6.36-6.34 (m, 4H), 1.63 (s, 6H) | 782.10 | 780.99 |
| 37 | 5 | | 8.06 (s, 1H), 7.89-7.82 (m, 2H), 7.72-7.42 (m, 17H), 7.20-7.16 (m, 4H), 7.09-7.02 (m, 2H), 6.92-6.86 (m, 4H), 6.36-6.33 (m, 4H), 1.82 (s, 6H) | 734.14 | 732.95 |

TABLE 1-continued
| Compound | Synthesis Scheme | Raw material used instead of original raw material used in Synthesis Scheme | $^1$H NMR (CDCl$_3$, 400 MHz) | MS/FAB found | calc. |
|---|---|---|---|---|---|
| 38 | 5 | 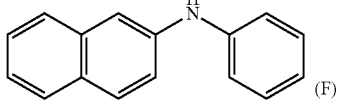 (F) | 8.06 (s, 1H), 7.89-7.72 (m, 4H), 7.69-7.42 (m, 21H), 7.22-7.18 (m, 3H), 7.09-7.02 (m, 2H), 6.90-6.87 (m, 3H), 6.35-6.31 (m, 2H), 1.83 (s, 6H) | 784.05 | 783.01 |
| 41 | 4 | 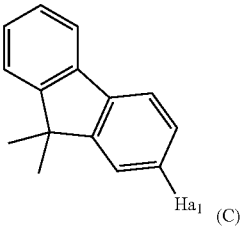 (C) | 8.07 (s, 1H), 7.95-7.85 (m, 4H), 7.75 (s, 1H), 7.68-7.40 (m, 13H), 7.35-7.33 (m, 1H), 7.28-7.20 (m, 7H), 7.09-7.02 (m, 3H), 6.88-6.85 (m, 4H), 6.38-6.34 (m, 4H), 1.85 (s, 6H), 1.83 (s, 6H) | 848.45 | 847.10 |
| 43 | 4 | 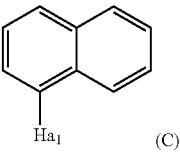 (C) 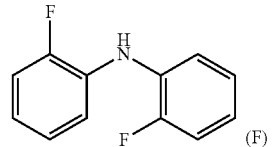 (F) | 8.06 (s, 1H), 7.99-7.95 (m, 2H), 7.78-7.66 (m, 6H), 7.62-7.40 (m, 14H), 7.32-7.26 (m, 3H), 7.22-7.16 (m, 6H), 6.89-6.82 (m, 4H), 1.83 (s, 6H) | 818.11 | 816.97 |
| 44 | 5 | 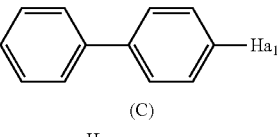 (C) 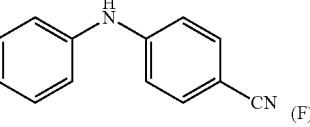 (F) | 8.07 (s, 1H), 7.86-7.80 (m, 4H), 7.75-7.51 (m, 21H), 7.30-7.26 (m, 2H), 7.08-6.90 (m, 7H), 6.52-6.50 (m, 2H), 1.83 (s, 6H) | 835.12 | 834.05 |
| 45 | 5 | 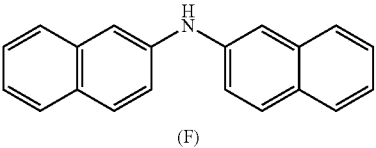 (F) | 8.06 (s, 1H), 7.88-7.70 (m, 6), 7.65-7.40 (m, 25H), 7.35-7.29 (m, 2H), 7.06-6.96 (m, 4H), 6.52-6.50 (m, 2H), 1.82 (s, 6H) | 834.25 | 833.07 |
| 46 | 5 | 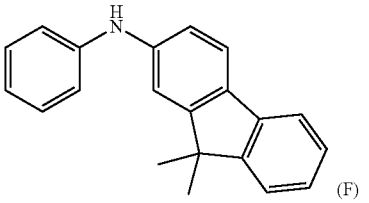 (F) | 8.06 (s, 1H), 7.98-7.90 (m, 3H), 7.84-7.52 (m, 19H), 7.32-7.22 (m, 4H), 7.10-7.02 (m, 2H), 6.86-6.80 (m, 4H), 6.56-6.50 (m, 3H), 1.83 (s, 6H), 1.81 (s, 6H) | 850.88 | 849.11 |

TABLE 1-continued

| Compound | Synthesis Scheme | Raw material used instead of original raw material used in Synthesis Scheme | $^1$H NMR (CDCl$_3$, 400 MHz) | MS/FAB found | calc. |
|---|---|---|---|---|---|
| 51 | 4 | (C) | 8.06 (s, 1H), 7.86-7.82 (m, 2), 7.76-7.52 (m, 13H), 7.32-7.28 (m, 5H), 7.12-7.08 (m, 2H), 6.99-6.93 (m, 4H), 6.42-6.36 (m, 3H), 1.83 (s, 6H) | 737.06 | 735.97 |
| 52 | 5 | (F) | 8.07 (s, 1H), 7.99-7.89 (m, 7H), 7.84-7.60 (m, 23H), 7.50-7.44 (m, 3H), 7.06-7.02 (m, 2H), 6.89-6.82 (m, 3H), 6.34-6.32 (m, 2H), 1.82 (s, 6H) | 904.44 | 903.13 |
| 53 | 4 | (A) (F) | 8.28 (m, 2H), 8.07 (s, 1H), 7.98 (m, 2H), 7.88 (d, 1H), 7.76-7.48 (m, 22H), 7.42-7.30 (m, 11H), 7.18-7.06 (m, 5H) | 858.26 | 857.09 |
| 57 | 5 | (F) | 8.06 (s, 1H), 7.96-7.88 (m, 3H), 7.84-7.48 (m, 22), 7.26-7.22 (m, 2H), 7.10-7.04 (m, 5H), 6.86-6.63 (m, 1H), 6.63-6.61 (m, 2H), 1.83 (s, 6H) | 823.41 | 823.03 |
| 59 | 5 | (E) | 8.06 (s, 1H), 7.98 (d, 1H), 7.94-7.86 (m, 4H), 7.84 (d, 2H), 7.70-7.46 (m, 15H), 7.30-7.24 (m, 4H), 7.10-7.04 (m, 3H), 6.88-6.82 (m, 2H), 6.36-6.62 (m, 4H), 1.82 (s, 6H) | 783.05 | 782.01 |
| 60 | 5 | (E) | 8.28 (m, 2H), 8.07 (s, 1H), 8.01 (s, 1H), 7.98-7.92 (m, 6H), 7.86-7.56 (m, 15H), 7.27-7.22 (m, 4H), 7.08-6.92 (m, 5H), 6.61-6.56 (m, 4H), 1.82 (s, 6H) | 834.12 | 833.07 |

TABLE 1-continued
| Compound | Synthesis Scheme | Raw material used instead of original raw material used in Synthesis Scheme | ¹H NMR (CDCl₃, 400 MHz) | MS/FAB found | MS/FAB calc. |
|---|---|---|---|---|---|
| 61 | 5 | 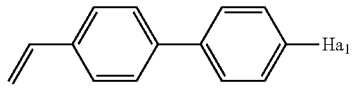 (E) | 8.06 (s, 1H), 7.97-7.82 (m, 4H), 7.78-7.40 (m, 19H), 7.26-7.22 (m, 4H), 7.16-7.12 (m, 4H), 6.88-6.84 (m, 2H), 6.46-6.42 (m, 4H), 1.82 (s, 6H) | 810.19 | 809.04 |
| 63 | 4 | | 8.06 (s, 1H), 7.96-7.86 (m, 2H), 7.76-7.52 (m, 22), 7.30-7.26 (m, 4H), 7.24-7.20 (m, 3H), 6.98-6.94 (m, 4H), 6.42-6.40 (m, 4H), 1.83 (s, 6H) | 808.21 | 807.03 |
| 64 | 4 | 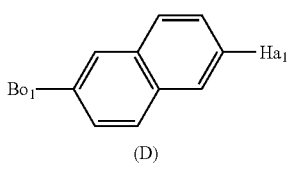 (D) | 8.06 (s, 1H), 8.00-7.92 (m, 4H), 7.90-7.80 (m, 4H), 7.72-7.52 (m, 17H), 7.46-7.30 (m, 6H), 7.12-7.10 (m, 2H), 7.08-6.98 (m, 4H), 6.41-6.36 (m, 4H), 1.83 (s, 6H) | 858.25 | 857.09 |
| 67 | 4 | 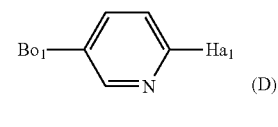 (D) | 8.56 (s, 1H), 8.07 (s, 1H), 7.98-7.92 (m, 4H), 7.84-7.48 (m, 19H), 7.23-7.10 (m, 8H), 6.90-9.82 (m, 2H), 6.36-6.32 (m, 4H), 1.83 (s, 6H) | 809.08 | 808.02 |
| 68 | 4 | 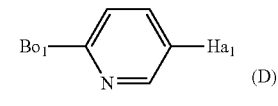 (D) | 8.56 (s, 1H), 8.07 (s, 1H), 7.98-7.88 (m, 5H), 7.80-7.58 (m, 17H), 7.28-7.12 (m, 6H), 6.94-9.90 (m, 4H), 6.36-6.32 (m, 4H), 1.82 (s, 6H) | 809.10 | 808.02 |
| 69 | 4 | 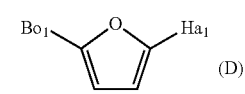 (D) | 8.06 (s, 1H), 7.98 (d, 1H), 7.78-7.42 (m, 19H), 7.28-7.20 (m, 5H), 7.16-7.12 (m, 3H), 6.92-6.88 (m, 5H), 6.33-6.30 (m, 4H), 1.83 (s, 6H) | 798.01 | 796.99 |
| 74 | 5 | 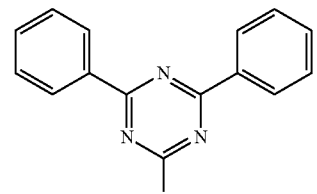 (C) | 8.54 (m, 4H), 8.32 (s, 1H), 7.98-7.76 (m, 11H), 7.68-7.56 (m, 11H), 7.28-7.24 (m, 4H), 6.96-6.90 (m, 4H), 6.36-6.32 (m, 4H), 1.83 (s, 6H) | 889.35 | 888.10 |
| 75 | 5 | 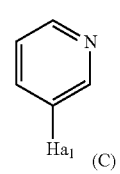 (C) | 8.26-8.16 (m, 2H), 8.05 (s, 1H), 7.98-7.94 (m, 1H), 7.86-7.48 (m, 15H), 7.28-7.10 (m, 6H), 6.95-6.90 (m, 4H), 6.36-6.32 (m, 4H), 1.82 (s, 6H) | 734.98 | 733.94 |

TABLE 1-continued

| Compound | Synthesis Scheme | Raw material used instead of original raw material used in Synthesis Scheme | ¹H NMR (CDCl₃, 400 MHz) | MS/FAB found | calc. |
|---|---|---|---|---|---|
| 76 | 4 | (structure with pentafluorophenyl–Ha₁) (C) | 8.06 (s, 1H), 7.86-7.82 (m, 4H), 7.78 (s, 1H), 7.72-7.57 (m, 10H), 7.40-7.28 (m, 7H), 6.98-6.92 (m, 4H), 6.40-6.36 (m, 4H), 1.83 (s, 6H) | 822.01 | 820.89 |
| 77 | 4 | carbazole (F); 4-vinyl-4'-Ha₁-biphenyl (E) | 8.06 (s, 1H), 7.99 (d, 2H), 7.94-7.50 (m, 31H), 7.36-7.32 (m, 2H), 7.08-7.02 (m, 2H), 1.82 (s, 6H) | 806.36 | 805.02 |
| 78 | 4 | carbazole (F); 9,9-dimethyl-2-vinyl-7-Ha₁-fluorene (E) | 8.06 (s, 1H), 7.99 (dd, 2H), 7.94-7.80 (m, 5H), 7.76 (s, 1H), 7.72-7.50 (m, 21H), 7.42-7.40 (m, 1H), 7.10-7.04 (m, 5H), 1.83 (s, 6H), 1.82 (s, 6H)/48 | 846.21 | 845.05 |
| 79 | 4 | 9-(4-Ha₁-phenyl)carbazole (C) | 8.06 (s, 1H), 8.01 (d, 2H), 7.92-7.88 (m, 2H), 7.82 (s, 1H), 7.78-7.48 (m, 20H), 7.42-7.40 (m, 7H), 7.12-7.08 (m, 2H), 6.89-6.83 (m, 4H), 6.36-6.32 (m, 4H), 1.83 (s, 6H) | 897.10 | 896.13 |

In Table 1 above, Ha₁ and Ha₂ are each independently iodine (I) or bromine (Br), and Bo1 is —B(OH)₂ or

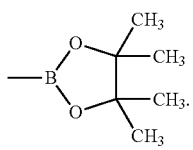

Example 1

As an anode, a 15 Ω/cm² (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. 2-TNATA was vacuum deposited on the ITO glass substrate to form a HIL having a thickness of 600 Å. Then, 4,4'-bis[N-(1-naphthyl)-N-phenylamino]biphenyl (NPB) was vacuum deposited on the HIL to form a HTL having a thickness of 300 Å. Next, 98 wt % of ADN used as a bule fluorescent host and 2 wt % of Compound 4 used as a blue fluorescent dopant were vacuum deposited on the HTL to form an EML having a thickness of 300 Å. Alg$_a$ was vacuum deposited on the EML to form an to ETL having a thickness of 300 Å. Then. LiF was vacuum deposited on the ETL to form an EIL having a thickness of 10 Å. Then, Al was vacuum deposited on the EIL to form a cathode having a thickness of 3000 Å, thereby completing the manufacture of an OLED.

Example 2

An OLED was manufactured in the same manner as in Example 1, except that Compound 37 was used as a dopant in forming the EML instead of Compound 4.

Example 3

An OLED was manufactured in the same manner as in Example 1, except that Compound 46 was used as a dopant in forming the EML instead of Compound 4.

Example 4

An OLED was manufactured in the same manner as in Example 1, except that Compound 52 was used as a dopant in forming the EML instead of Compound 4.

Example 5

An OLED was manufactured in the same manner as in Example 1, except that Compound 63 was used as a dopant in forming the EML instead of Compound 4.

Example 6

An OLED was manufactured in the same manner as in Example 1, except that Compound 74 was used as a dopant in forming the EML instead of Compound 4.

Comparative Example 1

An OLED was manufactured in the same manner as in Example 1, except that DPAVBi was used as a dopant in forming the EML instead of Compound 4.

Evaluation Example

Driving voltage, current density, brightness, efficiency, emission color, and half lifetime of each of the OLEDs of Examples 1 through 6 and Comparative Example 1 were evaluated using PR650 Spectroscan Source Measurement Unit (available from PhotoResearch), and the results are shown in Table 2 below:

TABLE 2

| | EML host | EML dopant | Driving voltage (V) | Current density (mA/cm$^2$) | Brightness (cd/m$^2$) | Efficiency (cd/A) | Emission color | Half lifetime (hr)[1] |
|---|---|---|---|---|---|---|---|---|
| Example 1 | ADN | Com. 4 | 6.25 | 50 | 2,965 | 5.93 | blue | 248 |
| Example 2 | ADN | Com. 37 | 6.23 | 50 | 3,025 | 6.05 | blue | 306 |
| Example 3 | ADN | Com. 46 | 6.13 | 50 | 3,060 | 6.12 | blue | 293 |
| Example 4 | ADN | Com. 52 | 6.26 | 50 | 3,080 | 6.16 | blue | 229 |
| Example 5 | ADN | Com. 63 | 6.25 | 50 | 2,985 | 5.97 | blue | 287 |
| Example 6 | ADN | Com. 74 | 5.46 | 50 | 1,175 | 2.35 | blue-green | 123 |
| Comparative Example 1 | ADN | DPAVBi | 7.35 | 50 | 2,065 | 4.13 | blue | 145 |

[1]Reference current density of half lifetime: 100 mA/cm$^2$

From the results shown in Table 2, it is confirmed that the Examples 1 through 0.6 of the OLEDs exhibit lower driving voltage, higher brightness and efficiency, and longer lifetime, as compared to the OLED of Comparative Example 1.

As described above, according to the one or more embodiments of the present invention, an OLED including an organic layer including the heterocyclic compound may have excellent performance, for example, low driving voltage, high brightness, high efficiency, and long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

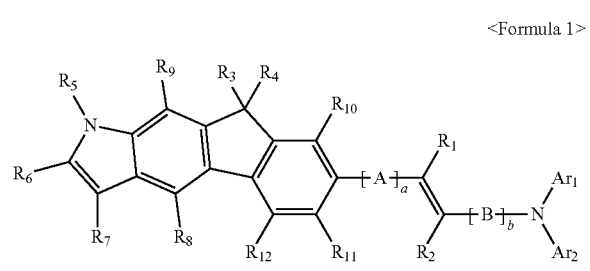

<Formula 1> wherein $R_1$ through $R_{12}$ are each independently selected from the group consisting of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl gruop, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, and an amino group substituted with a substituted or unsubstituted $C_5$-$C_{30}$ aryl group or a substituted or unsubstituted $C_3$-$C_{30}$ heteroaryl group;

$Ar_1$ and $Ar_2$ are each independently a substituted or unsubstituted $C_5$-$C_{30}$ aryl group and a substituted or unsubstituted $C_3$-$C_{30}$ heteroaryl group;

A and B are divalent linking groups, and each independently a substituted or unsubstituted $C_5$-$C_{30}$ arylene group or a substituted or unsubstituted $C_3$-$C_{30}$ heteroarylene group; and a is an integer of 0 to 3, wherein when a is 2 or greater, at least two of A groups are the same as or different from each other; and b is an integer of 0 to 3, wherein when b is 2 or greater, at least two of B groups are the same as or different from each other.

2. The heterocyclic compound of claim 1, wherein $R_3$ and $R_4$ are linked to form a substituted or unsubstituted $C_5$-$C_{30}$ aryl group; and $Ar_1$ and $Ar_2$ are linked to each other to form a ring, thereby forming a substituted or unsubstituted $C_3$-$C_{30}$ heteroaryl group.

3. The heterocyclic compound of claim 1, wherein $R_1$ through $R_{12}$ are each independently selected from the group consisting of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spiro-fluorenyl group, a substituted or unsubstituted carbozolyl group, a substituted or unsubstituted phenanthrenyl group, a substituted or unsubstituted pyranyl group, a substituted or unsubstituted pyridinyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolinyl group, a substituted or unsubstituted pyrazolyl group, a substituted or unsubstituted imidazopyridinyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolizinyl group, a substituted or unsubstituted pyridoindolizinyl group, a substituted or unsubstituted indazolyl group, a substituted or unsubstituted carbazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, and a substituted or unsubstituted tetrazolyl group.

4. The heterocyclic compound of claim 1, wherein $R_1$ through $R_{12}$ are each independently selected from the group consisting of a hydrogen atom, a deuterium atom, a halogen atom, a substituted or unsubstituted methyl group, a substituted or unsubstituted ethyl group, a substituted or unsubstituted propyl group, a substituted or unsubstituted butyl group, and groups represented by Formulae 2A through 2H below:

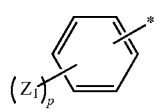

Formula 2A

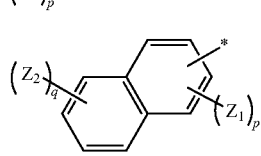

Formula 3B

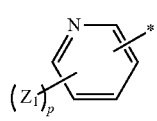

Formula 2C

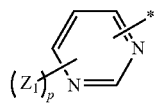

Formula 2D

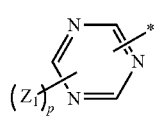

Formula 2E

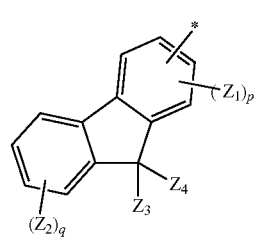

Formula 2F

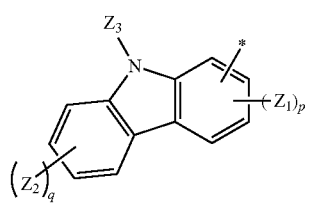

Formula 2G

-continued

Formula 2H

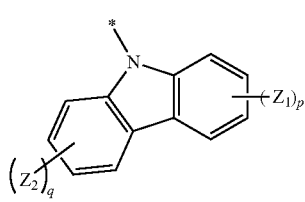

wherein $Z_1$, $Z_2$, $Z_3$, and $Z_4$ are each independently selected from the group consisting of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted carbazolyl group, and a substituted or unsubstituted quinolinyl group, a plurality of $Z_1$ and $Z_2$ groups are each independently the same as or different from each other;

p is an integer of 1 to 5;

q is an integer of 1 to 4; and

* indicates a binding site.

5. The heterocyclic compound of claim 1, wherein $R_1$ through $R_{12}$ are each independently selected from the group consisting of a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, and groups represented by Formulae 3A through 3K below:

Formula 3A

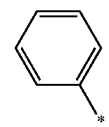

Formula 3B

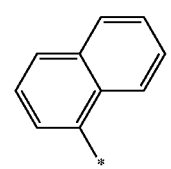

Formula 3C

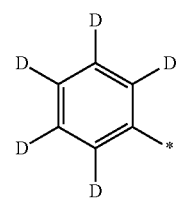

Formula 3D

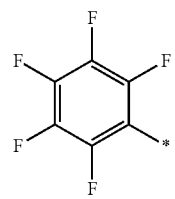

Formula 3E

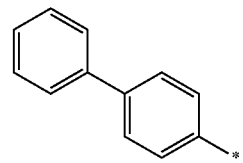

Formula 3F

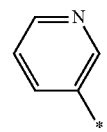

Formula 3G

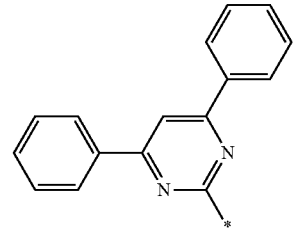

Formula 3H

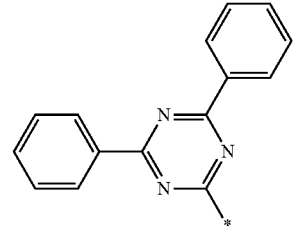

Formula 3I

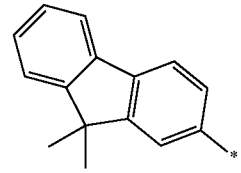

Formula 3J

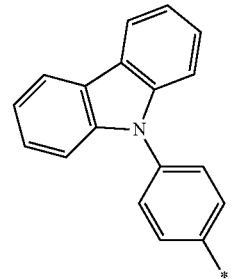

Formula 3K wherein * indicates a binding site and D is a deuterium atom.

6. The heterocyclic compound of claim 1, wherein $Ar_1$ and $Ar_2$ are each independently selected from the group consisting of a substituted or unsubstituted phenyl group, a substituted or unsubstituted terphenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spiro-fluorenyl group, a substituted or unsubstituted dibenzothiophenyl group, a substituted or unsubstituted dibenzofuranyl group, a substituted or unsubstituted carbazolyl group, a substituted or unsubstituted pyridinyl group, a substituted or unsubstituted pyrimidinyl group, a substituted or unsubstituted triazinyl group, a substituted or unsubstituted chrysenyl group, a substituted or unsubstituted perylenyl group, and a substituted or unsubstituted oxadiazole group.

7. The heterocyclic compound of claim 1, whererin each of $Ar_1$ and $Ar_2$ is independently one of the groups represented by Formulae 4A through 4I below:

Formula 4A

Formula 4B

Formula 4C

Formula 4D

Formula 4E

Formula 4F

Formula 4G

Formula 4H

Formula 4I wherein $Z_{11}$, $Z_{12}$, $Z_{13}$, and $Z_{14}$ are each independently selected from the group consisting of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolinyl group, a plurality of $Z_{11}$, $Z_{12}$, $Z_{13}$, and $Z_{14}$ groups are each independently the same as or different from each other;

r and s are each independently an integer of 1 to 5;

t is an integer of 1 to 4;

u is an integer of 1 or 2; and

* indicates a binding site.

8. The heterocyclic compound of claim 1, wherein each of $Ar_1$ and $Ar_2$ is independently one of the groups represented by Formulae 5A through 5Q below:

Formula 5A 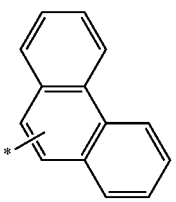

Formula 5B 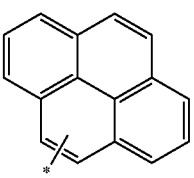

Formula 5C 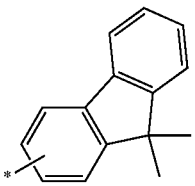

Formula 5D 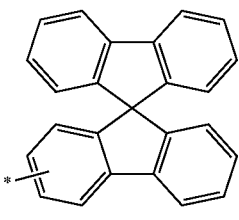

Formula 5E 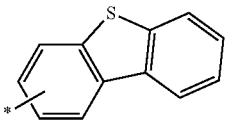

Formula 5F 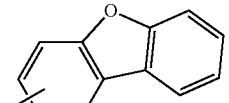

Formula 5G 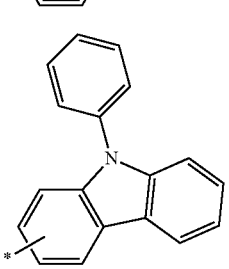

Formula 5H

Formula 5I

Formula 5J

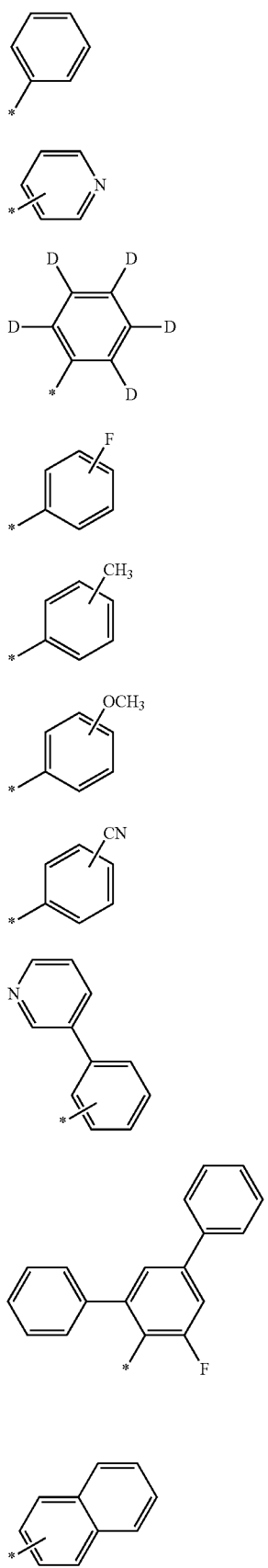

Formula 5K

Formula 5L

Formula 5M

Formula 5N

Formula 5O

Formula 5P

Formula 5Q wherein * and *' indicate binding sites and D is a deuterium atom.

9. The heterocyclic compound of claim 1, wherein A and B are each independently selected from the group consisting of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group.

10. The heterocyclic compound of claim 9, wherein each of A and B is independently one of the groups represented by Formulae 6A through 6K below:

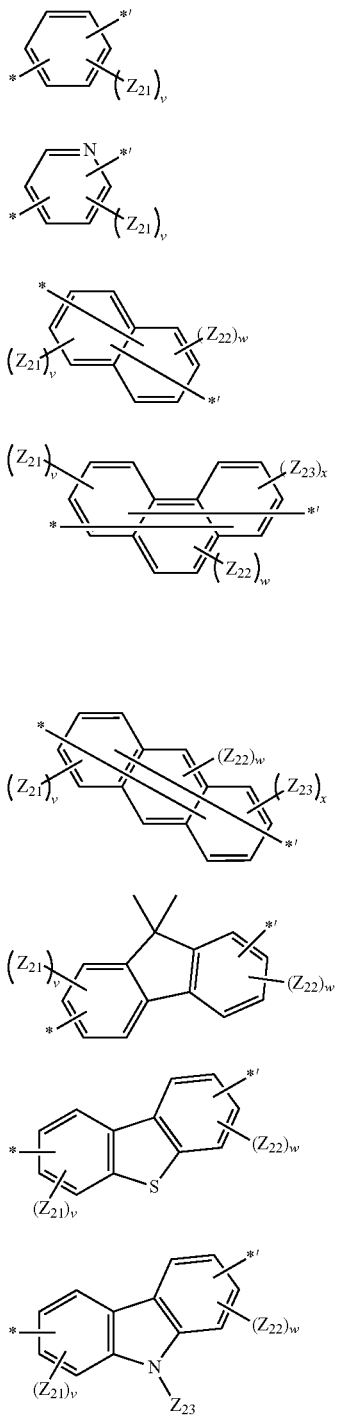

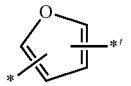

Formula 6I

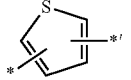

Formula 6J

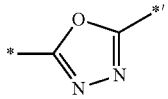

Formula 6K wherein $Z_{21}$, $Z_{22}$, and $Z_{23}$ are each independently selected from the group consisting of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, and a substituted or unsubstituted pyridinyl group, a plurality of $Z_{21}$, $Z_{22}$, and $Z_{23}$ groups are each independently the same as or different from each other;

v, w, and x are each independently an integer of 1 to 4; and

* and *' indicate binding sites.

11. The heterocyclic compound of claim 10, wherein each of A and B is independently one of the groups represented by Formulae 7A through 7N below:

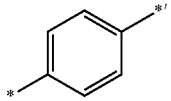

Formula 7A

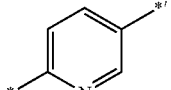

Formula 7B

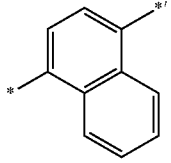

Formula 7C

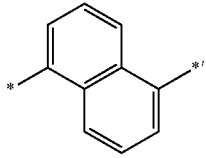

Formula 7D

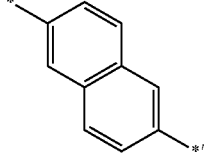

Formula 7E

Formula 7F
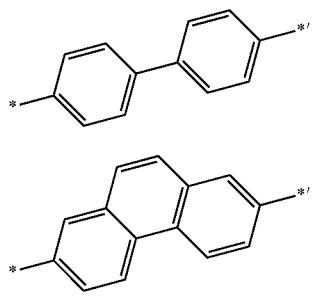
Formula 7G
Formula 7H
Formula 7I
Formula 7J
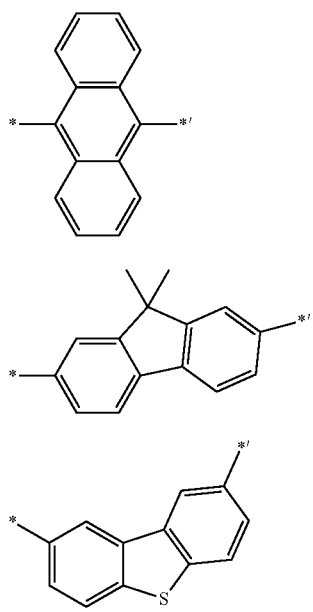
Formula 7K
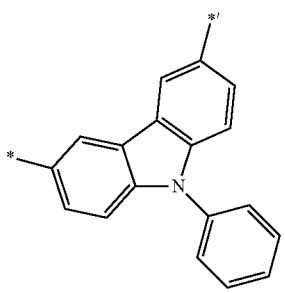
Formula 7L
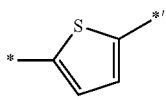
Formula 7M
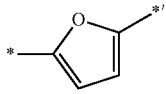
Formula 7N
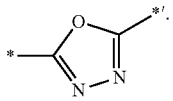
12. The heterocyclic compound of claim 1, wherein the heterocyclic compound represented by Formula 1 is one of Compounds 4, 37, 46, 52, 63, and 74:
Compound 4
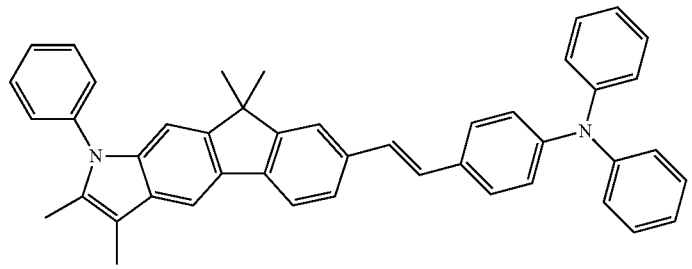
Compound 37
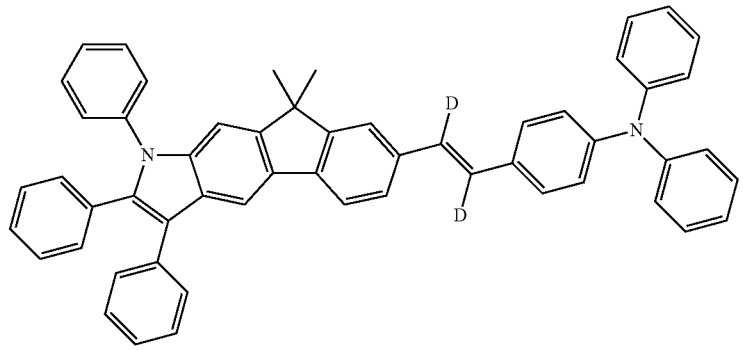

Compound 46
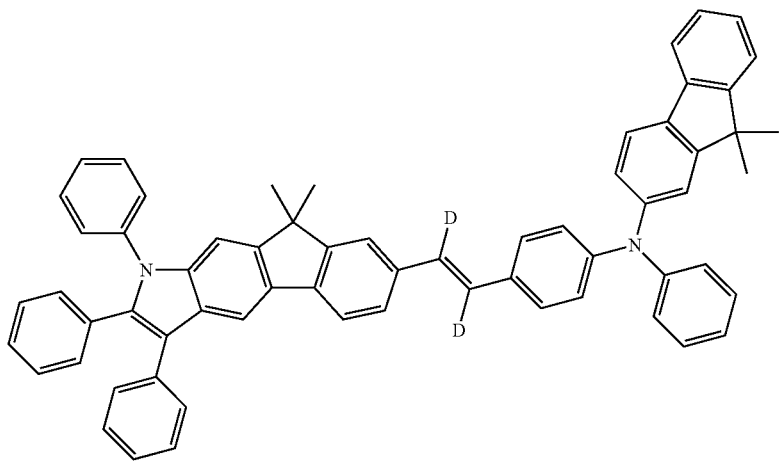
Compound 52
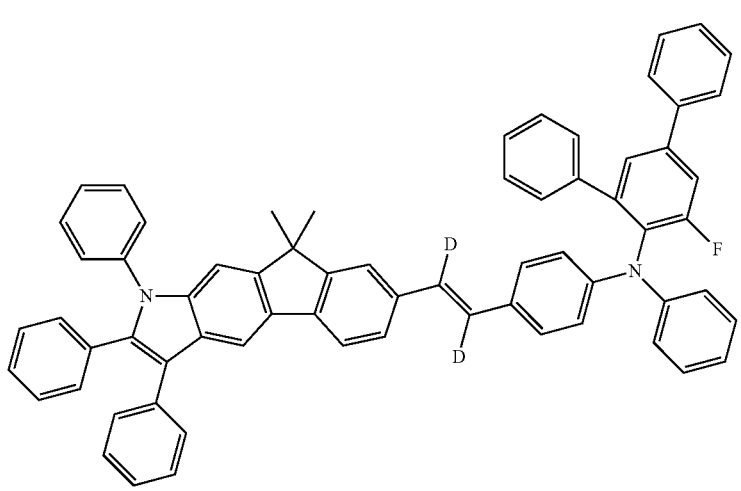
Compound 63
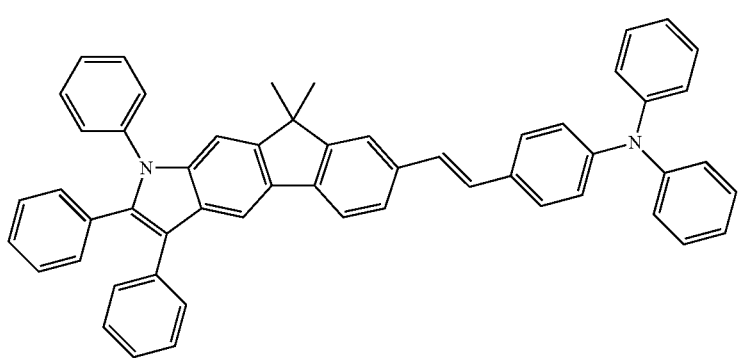

Compound 74

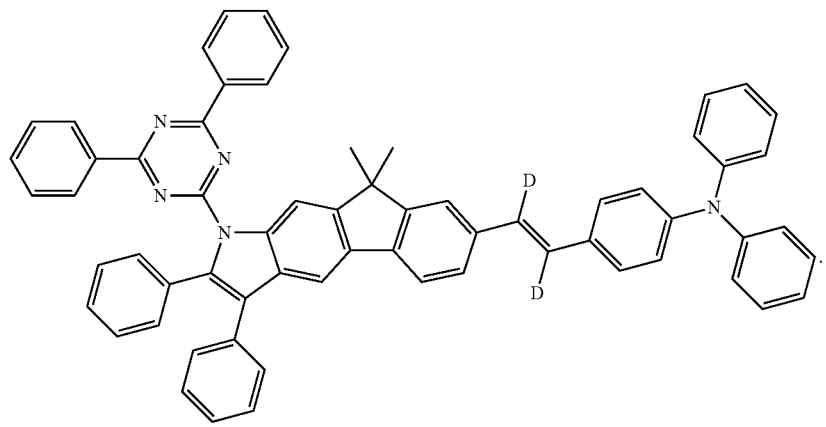

13. An organic light-emitting diode comprising:
a first electrode;
a second electrode facing the first electrode; and
an organic layer interposed between the first electrode and the second electrode,
wherein the organic layer comprises at least one layer and at least one of the heterocyclic compounds represented by Formula 1 according to claim 1.

14. The organic light-emitting diode of claim 13, wherein the organic layer comprises at least one layer selected from the group consisting of an emission layer, a hole injection layer, a hole transport layer, and a hole injection and transport layer having hole injection and transport abilities, wherein at least one layer of the emission layer, the hole injection layer, the hole transport layer, and the hole injection and transport layer comprises at least one of the heterocyclic compounds represented by Formula 1.

15. The organic light-emitting diode of claim 14, wherein the organic layer comprises an emission layer, wherein the emission layer comprises a host and a dopant and the heterocyclic compound is a fluorescent host, a phosphorescent host, or a fluorescent dopant of the emission layer.

16. The organic light-emitting diode of claim 14, wherein the organic layer comprises an emission layer, wherein the emission layer comprises a host and a dopant and further comprises a phosphorescent dopant.

17. The organic light-emitting diode of claim 14, wherein at least one layer of the hole injection layer, the hole transport layer, and the hole injection and transport layer further comprises a charge-generating material, in addition to the heterocyclic compound.

18. The organic light-emitting diode of claim 14, wherein the organic layer further comprises an electron transport layer, wherein the electron transport layer comprises an electron transporting organic compound and a metal-containing material.

19. The organic light-emitting diode of claim 18, wherein the metal-containing material comprises a Li complex.

20. The organic light-emitting diode of claim 13, wherein at least one layer in the organic layers is formed by a wet process.

* * * * *